(12) United States Patent
Sheehan

(10) Patent No.: US 11,253,402 B2
(45) Date of Patent: Feb. 22, 2022

(54) ORTHOSIS APPARATUS AND METHOD OF USE

(71) Applicant: FastForm Research Ltd., Waterford (IE)

(72) Inventor: David Sheehan, Dunmore East (IE)

(73) Assignee: FastForm Research Ltd., Waterford (IE)

( * ) Notice: Subject to any disclaimer, the term of this patent is extended or adjusted under 35 U.S.C. 154(b) by 323 days.

(21) Appl. No.: 16/261,059

(22) Filed: Jan. 29, 2019

(65) Prior Publication Data

US 2019/0269558 A1 Sep. 5, 2019

Related U.S. Application Data

(60) Provisional application No. 62/638,107, filed on Mar. 3, 2018.

(51) Int. Cl.
*A61F 13/04* (2006.01)
*A61F 5/01* (2006.01)
(Continued)

(52) U.S. Cl.
CPC ............ *A61F 13/048* (2013.01); *A61F 5/019* (2013.01); *A61F 5/0111* (2013.01);
(Continued)

(58) Field of Classification Search
CPC .... A61F 13/048; A61F 5/0195; A61F 5/0111; A61F 5/022; A61F 5/05; A61F 5/019; A61F 5/0118; A61F 13/046; A61F 5/01; A61F 5/0104; A61F 5/0102; A61F 13/066; A61F 13/04; A61F 5/0113; A61F 5/0106; A61F 5/0109; A61F 5/058; A61F 5/05841; A61F 5/0585; A61F 5/05858; A61F 5/05866; A61F 5/05875; A61F 5/05883;
(Continued)

(56) References Cited

U.S. PATENT DOCUMENTS 2,494,770 A * 1/1950 Maclaughlin .......... A43C 11/12
36/103
3,351,055 A 11/1967 Gottfried
(Continued)

FOREIGN PATENT DOCUMENTS

CA 2701622 A1 12/2008
CA 2701622 C 12/2008
(Continued)

OTHER PUBLICATIONS

International Search Report and the Written Opinion of the International Searching Authority PCT/EP2019/054462 dated Jun. 5, 2019.
(Continued)

*Primary Examiner* — Rachael E Bredefeld
*Assistant Examiner* — William T Kao
(74) *Attorney, Agent, or Firm* — Lodestone Legal Group; Jeromye V. Sartain

(57) ABSTRACT

An improved orthosis apparatus for being selectively formed and applied and removed having offset zipper closures on two shell members for improved hinging and opening and access for initial application and forming when malleable and for removing and reinstalling when hardened.

16 Claims, 25 Drawing Sheets

(51) Int. Cl.
*A61F 5/02* (2006.01)
*A61F 5/05* (2006.01)
*A61F 13/02* (2006.01)
*A61L 15/07* (2006.01)

(52) U.S. Cl.
CPC .......... *A61F 5/0118* (2013.01); *A61F 5/0195* (2013.01); *A61F 5/022* (2013.01); *A61F 5/05* (2013.01); *A61F 13/046* (2013.01); *A61F 13/0273* (2013.01); *A61L 15/07* (2013.01)

(58) Field of Classification Search
CPC ..... A43B 11/00; A43B 23/081; A43B 23/082; A43B 23/085; A43B 23/086; A43B 23/087; A43C 11/12; A44B 19/382; A44B 19/02; A44B 19/04; A44B 19/06; A41D 13/08; A41D 13/055; A41D 2300/30; A41B 11/08
USPC ............... 602/6, 7, 12, 23, 27, 28, 29; 36/99
See application file for complete search history.

(56) References Cited

U.S. PATENT DOCUMENTS

| | | | | |
|---|---|---|---|---|
| 4,143,655 | A | | 3/1979 | Custer et al. |
| 4,217,706 | A | * | 8/1980 | Vartanian ............. A43C 11/008 36/110 |
| 4,442,834 | A | | 4/1984 | Tucker et al. |
| 4,821,432 | A | * | 4/1989 | Reiber ................. A43B 7/1465 36/110 |
| 5,730,498 | A | * | 3/1998 | Hanson .................. B60R 22/14 2/2.17 |
| 6,093,161 | A | | 7/2000 | Vlaeyen et al. |
| 7,985,192 | B2 | | 7/2011 | Sheehan |
| 8,118,762 | B2 | * | 2/2012 | Bort ...................... A61F 5/0109 602/23 |
| 8,303,527 | B2 | | 11/2012 | Joseph |
| 8,821,423 | B2 | | 9/2014 | Conlon et al. |
| 8,853,603 | B2 | | 10/2014 | Sheehan |
| 9,561,128 | B2 | | 2/2017 | Joseph |
| 2003/0226288 | A1 | * | 12/2003 | Brown .................. A43B 7/141 36/144 |
| 2006/0135899 | A1 | * | 6/2006 | Jerome ................ A61F 5/0111 602/23 |
| 2007/0100266 | A1 | | 5/2007 | Hargrave |
| 2007/0214681 | A1 | * | 9/2007 | Dezfouli ................ A43B 3/242 36/101 |
| 2008/0141565 | A1 | * | 6/2008 | Rini ..................... A61F 5/0195 36/77 R |
| 2008/0319362 | A1 | | 12/2008 | Joseph |
| 2009/0049710 | A1 | * | 2/2009 | Barnett .................. A41D 15/00 36/1.5 |
| 2009/0076428 | A1 | | 3/2009 | Kay |
| 2009/0204047 | A1 | | 8/2009 | MacArthur |
| 2012/0215144 | A1 | | 8/2012 | Rice |
| 2013/0102940 | A1 | | 4/2013 | Joseph |
| 2016/0074197 | A1 | * | 3/2016 | Jones .................... A61F 5/0106 602/23 |
| 2016/0235573 | A1 | * | 8/2016 | Walborn ............... A61B 5/1118 |
| 2017/0189241 | A1 | | 7/2017 | Joseph |
| 2019/0240057 | A1 | * | 8/2019 | Gunnsteinsson ..... A61F 5/0111 |

FOREIGN PATENT DOCUMENTS

| | | | | |
|---|---|---|---|---|
| CN | 205268361 | U | | 1/2016 |
| EP | 0401883 | B1 | | 8/1994 |
| EP | 0770369 | A1 | | 5/1997 |
| EP | 0639086 | B1 | | 8/2001 |
| GB | 2454943 | A | * | 5/2009 ......... A61B 17/3207 |
| JP | 09220245 | A | | 8/1997 |
| WO | 1993021967 | A1 | | 11/1993 |
| WO | 2008157738 | A1 | | 12/2008 |

OTHER PUBLICATIONS

Rolyan "Rolyan AquaForm Zippered Wrist and Thumb Spica Splint" web page content obtained Oct. 19, 2020 from https://www.performancehealth.com/rolyan-aquaform-zippered-wrist-and-thumb-spica-splint.
Image of volar forearm splint obtained Oct. 19, 2020 from http://www.routemed.co.za/uploadedImages/Hand/ManuZip%20Eco%20-%20112620.jpg.
Medical Expo Teyder "Tibia Splint Zipper 132RD" web page content obtained Oct. 19, 2020 from https://www.medicalexpo.com/prod/teyder/product-85023-670893.html.
Medical Expo Teyder "Wrist Splint Zipper 100MN" web page content obtained Oct. 19, 2020 from https://www.medicalexpo.com/prod/teyder/product-85023-670890.html.
StockxMedical "Wrist Splint Ortho zip + E" web page content obtained Oct. 19, 2020 from https://www.stockxmedical.com/en/wrist-splint-ortho-zip-e.html.
Blatchford "Aircast Boot (Diabetic Walker)" product literature obtained Sep. 12, 2018.
Ossur "Rebound Diabetic Walker" product literature obtained Sep. 12, 2018.
Ossur "Rebound Diabetic Walker" instructions for use obtained Sep. 12, 2018.
Ossur "Ossur DH Offloading Walker" web page content obtained Oct. 19, 2020 from https://www.dme-direct.com/ossur-dh-offloading-walker.

\* cited by examiner

ORTHOSIS APPARATUS AND METHOD OF USE

RELATED APPLICATIONS

This non-provisional patent application claims priority pursuant to 35 U.S.C. § 119(e) to and is entitled to the filing date of U.S. Provisional Patent Application Ser. No. 62/638,107 filed Mar. 3, 2018, and entitled "Orthosis Apparatus and Method of Use." The contents of the aforementioned application are incorporated herein by reference.

BACKGROUND

The subject of this patent application relates generally to medical immobilization or orthotic devices, and more particularly to an orthosis apparatus configured for being selectively formed and applied and removed.

The following description includes information that may be useful in understanding the present invention. It is not an admission that any of the information provided herein is prior art or relevant to the presently claimed invention, or that any publication specifically or implicitly referenced is prior art.

Applicant(s) hereby incorporate herein by reference any and all patents and published patent applications cited or referred to in this application, to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

By way of background, immobilization of fractured or injured joints or limbs typically involves the process of restraining the joint or limb in place with a splint, cast, or brace. This is done to prevent the fractured/injured area from moving or being disturbed during the healing process.

Traditionally Plaster of Paris on fabric or gauze bandage has been used to form casts for the immobilization of limbs. However, Plaster of Paris has a number of disadvantages associated with it. For example, Plaster of Paris is relatively heavy and bulky, has a slow setting time, cannot be reformed once set, possesses low impact resistance, and is susceptible to deterioration or damage once exposed to moisture thus making bathing and showering difficult. Additional concerns associated with the use of Plaster of Paris casting bandages are that they require a significant amount of time, usually 24 to 72 hours, to achieve their maximum strength, and that heat is generated from the exothermic setting reaction. Plaster of Paris also has poor radiopacity, which often prevents the continued monitoring of the limb during the healing process. In addition, Plaster of Paris is substantially impervious to transmission of water vapor, such as perspiration. Thus, Plaster of Paris traps moisture, which can result in significant skin maceration.

Similarly, more recently fiberglass casts have been introduced that are similar to Plaster of Paris casts in terms of being applied or wrapped on the affected limb over a sock or dressing of some kind but are relatively lighter weight and stronger as being formed from woven fiberglass typically coated with a polyurethane resin. Such fiberglass material is also known to set faster, in on the order of 30 minutes to 2 hours versus the 24 to 72 hours for Plaster of Paris casts. However, fiberglass casts are also not particularly breathable or waterproof and, like Plaster of Paris casts, cannot be reformed once set and so must instead be cut off in order to evaluate the limb or affected area and a new cast applied if further immobilization is deemed necessary by the clinician.

One partial solution to improve breathability is the use of a thermoplastic mesh as disclosed in U.S. Pat. No. 4,143,655 to Custer et al. A drawback with this method, however, is the necessity to apply multiple layers of mesh to achieve adequate strength to support and protect body areas. Another drawback of this method is that the mesh needs to be trimmed in order to fit different body areas and this results in sharp edges that are formed due to trimming. Another disadvantage of this method is that underlying bandages, padding, dressings, and gauzes can become wet because the material is usually heated using a hot water bath to soften the material to facilitate molding. Moist dressings promote bacteria growth and can lead to discomfort and further complications.

Other proposed solutions involve the use of thermoplastic materials. It is usually prescribed that thermoplastic mesh and thermoplastic sheets with perforations are heated using a water bath (see, e.g., U.S. Pat. No. 6,093,161). This will help to reduce the (unwanted) high tack characteristic associated with these materials, which makes it otherwise difficult for the user to handle. However, this means that these devices and materials are often wet when applied which can again in some instances sustain bacteria growth and MRSA or more generally just be unpleasant for the patient.

In the case of casts and splints it is important that such devices and materials also have sufficient strength to maintain correct alignment of fractured bones, or to restrict movement of a limb in order to promote healing, or to stabilize and help reduce swelling of injured limbs, or to protect a body area from impact and injury, or in some cases even support weight or be load-bearing. Specifically, in cases where devices or materials are used to protect body parts from impact and injury it is important that the devices or materials have sufficient strength to withstand an impact and also be capable of transmitting/dissipating the force of the impact onto and across underlying padding or shock absorbing materials to reduce or prevent injury to the underlying body part on humans and animals.

Those skilled in the art will recognize the importance of having breathable and open surfaces in devices and materials used for immobilization, bracing, casting, protection, or support of limbs and body parts on humans and animals in order to reduce skin maceration problems and clinical complications and to promote a reduction of healing times while still providing the aforementioned strength and workability and convenience in use.

In the context of ankle and foot orthoses ("AFO"), as with other limbs that may be treated, it is generally desirable to have a strong and lightweight, breathable cast or splint device that is relatively easy to use and form to the patient and thus to apply, preferably in a manner that allows for the removal and reapplication of the device rather than having to destroy it and form another. This would be particularly beneficial, for example, in the context of diabetic foot casting, a growing market segment where casts typically have to be replaced on a weekly basis to change wound dressings, which could lead to up to 10 or more casts per episode.

One of the main design challenges with AFO products and other orthotics is accommodating the large variances in limb sizes across populations, since such orthotic devices are pre-formed and so typically are of a relatively fixed size. Taking again the AFO example, dimensions such as overall foot length, ball of foot circumference, circumference at the malleoli, heel length to knee, and calf circumference all come into play, with other variations seen even on a single patient due to swelling increases or decreases over time. With a non-stretchable or somewhat rigid device, this would require several sizes and configurations to cover the population (e.g., 95 percentile).

Previous approaches to such sizing challenges for the pre-formed cast, splint or brace product involve two halves or shells or a single piece of formable material, either way with overlapping edges, which helps to reduce the number of sizes needed but results in having a product with excessive material, thus extra cost. Furthermore, those overlapping edges may cause a crease and be uncomfortable on the patient. In diabetic patients this can lead to ulceration of the underlying skin. One example of such a thermoformable product with overlapping edges is shown in U.S. Pat. No. 8,303,527 to Joseph (see, e.g., FIGS. 16, 21 and 22). In the case of walker boots, a large amount of padding is often used and/or an air bladder to accommodate the general population, and yet this still results in at least 5 sizes being needed in known applications.

The use of zippers to selectively join opposed edges in orthopedic devices rather than having such edges overlap is also generally known. For example, U.S. Pat. No. 6,093,161 to Vlaeyen et al. entitled "Thermoplastic Apparatus with Fastener" discloses a sheet of thermoplastic material that is pre-cut in a shape that generally conforms to and encircles a limb or other body part to be treated, with the fastener such as a zipper directly attached to the opposing edges of the thermoplastic material to allow such to be selectively removed from and put back on the treated area. However, such thermoplastic apparatus still suffers from a number of shortcomings in use. For one, there is difficulty in getting the apparatus on and off since there is only one zipper and otherwise there is no hinge region opposite the fastener to allow greater opening of the apparatus while still in its hardened or rigid condition, as it is undesirable to attempt to reheat such a thermoplastic orthopedic device while being worn for a number of reasons. Secondly, the Vlaeyen thermoplastic apparatus being pre-cut to a shape to encircle a particular area to be treated and being joined along a single non-overlapping edge while not being engineered or provided with features enabling larger scale stretch or sizing adjustment of the apparatus when moldable, it suffers from the drawbacks of other known pre-formed orthopedic devices in terms of the number of sizes of the device required to accommodate the large variances in limb sizes across populations.

What has been needed and heretofore unavailable is an orthosis apparatus configured for being selectively formed and applied and removed that is relatively easy to use in custom molding or forming when malleable and in removing and reapplying when hardened and that is comfortable and breathable when worn while providing the necessary structural support and proper anatomical fit to the treated area, all while being cost effective as by eliminating excess material and reducing the total number of sizes required to treat the majority of the target population.

Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing an improved orthosis apparatus for being selectively formed and applied and removed. In at least one embodiment, offset zipper closures on two shell members are provided for improved hinging and opening and access for initial application and forming when malleable and for removing and reinstalling when hardened.

According to a further aspect, the shell configuration (geometry and material) is designed for structural integrity of the zipper closures and of the overall apparatus while allowing for optimized stretch when malleable so as to reduce the number of sizes required to accommodate the majority of the target population.

According to a still further aspect, a selectively removable or hinged toe box is provided for protection of the toes and access to the toes for inspection without removal of the apparatus.

According to a still further aspect, selective insertion of a moldable or non-moldable insole with or without an optional rocker is provided for comfort and support and improved weight distribution in diabetic total contact cast applications.

And according to a still further aspect, selective insertion and use of an inflation bladder is provided to accommodate anatomical variances post-forming (once the apparatus is formed and hardened) such as due to increased or decreased swelling in the treated area.

And according to a still further aspect, selective insertion and use of a cold therapy pad is provided to cool the underlying joint or skin to reduce swelling and pain and promote recovery of the treated area post-forming (once the apparatus is formed and hardened).

Other objects, features, and advantages of aspects of the present invention will become more apparent from the following detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

Figure 1:
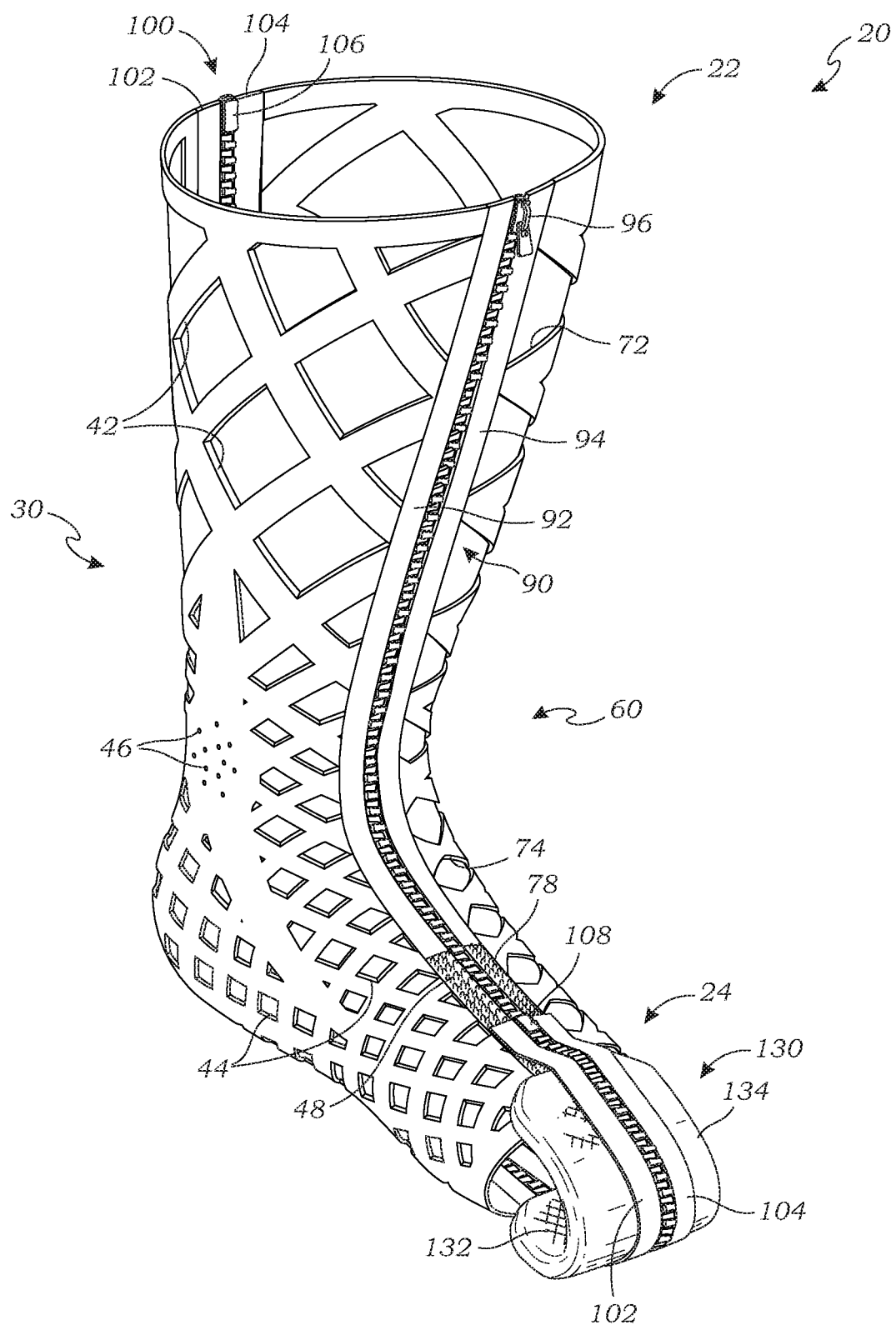
FIG. 1 is a perspective view of an exemplary orthosis apparatus, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments. More generally, those skilled in the art will appreciate that the drawings are schematic in nature and are not to be taken literally or to scale in terms of material configurations, sizes, thicknesses, and other attributes of an apparatus according to aspects of the present invention and its components or features unless specifically set forth herein.

DETAILED DESCRIPTION

The following discussion provides many exemplary embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

While the inventive subject matter is susceptible of various modifications and alternative embodiments, certain illustrated embodiments thereof are shown in the drawings and will be described below in detail. It should be understood, however, that there is no intention to limit the invention to any specific form disclosed, but on the contrary, the inventive subject matter is to cover all modifications, alternative embodiments, and equivalents falling within the scope of any appended claims.

Generally and by way of introduction, the present specification discloses an improved orthosis apparatus configured as an alternative to casting and having benefits and advantages over traditional casts for patients and clinicians. As plaster and fiberglass casts are made from rolls of these materials and formed directly on the patient, sizing is not an issue, at least as relating to any set dimensions, while such is an issue for pre-formed orthoses, though with other advantages. There is herein disclosed a somewhat symmetrically shaped two-half orthosis device with apertures and at least partially formed from re-moldable thermoplastic material that can be configured as a cast-type product for immobilization, bracing, casting, splinting, protection, or support of limbs and body parts on humans and animals. In the exemplary ankle and foot orthosis ("AFO") as shown, besides treating breaks, sprains and other injuries, a device according to aspects of the present invention may find application in treating such other diseases and conditions as diabetic foot ulcers ("DFU's"), for which a so-called "total contact cast" ("TCC") is often prescribed. The term "cast" employed herein generally refers to an embodiment of the device in one or more preformed sheets or shell portions used for limb immobilization, support, and/or protection but is to be understood more broadly as any such stabilization orthotic device in whatever form according to aspects of the present invention, and in any event all such illustrated embodiments herein are to be understood as exemplary and non-limiting. Particularly, while the exemplary context is an AFO, it will be appreciated that a device according to aspects of the present invention may find application in treating other injuries, diseases and conditions of various human and animal limbs and other body parts, including but not limited to the arm, wrist, and/or hand, the leg, the neck, and the back or torso.

Staying with the exemplary AFO context throughout for illustration, aspects of the orthosis apparatus relate to such a device configured for being selectively formed and applied and removed that is relatively easy to use in custom molding or forming when malleable and in removing and reapplying when hardened and that is comfortable and breathable when worn while providing the necessary structural support and proper anatomical fit to the treated area, all while being cost effective as by eliminating excess material and reducing the total number of sizes required to treat the majority of the target population. In regard to sizing, generally, it is expected that three sizes, nominally "small," "medium," and "large," of such an orthosis apparatus with no overlapping edges may be provided employing features and aspects of the present invention as ensuring that an anatomically sufficient, customized fit is achieved in length and circumference across a substantial portion of the target (e.g., adult) population (e.g., 95% conformity), more about which is said below in connection with FIGS. 1-3. For purposes of illustration, the apparatus shown and described and any dimensions disclosed herein are in connection with the "medium" sized AFO, again without limitation, unless expressly indicated otherwise, as those skilled in the art will of course appreciate that the apparatus can simply be scaled up or down in the AFO context, or scaled and reconfigured as needed for other contexts, without departing from the spirit and scope of the invention. At a high level, to overcome the design challenge of achieving anatomical conformity for the majority of a target population with a minimal number of sizes of the orthosis, such an apparatus has been devised with a particular geometry that is stretchable and/or compressible when in the pliable state to accommodate sizing. This is achieved by engineering the substrate in terms of geometry and material(s) to stretch in a certain range and/or direction. To assist in enabling the stretch function, one such exemplary thermoformable material and the means for its activation is as disclosed in commonly-owned U.S. Pat. No. 8,853,603 entitled "Thermo-Formable Support Products and Heating Means Therefor," incorporated herein by reference. Those skilled in the art will appreciate that all such material call-outs are illustrative of materials and properties that may be employed in conjunction with and according to aspects of the present invention, but not necessarily and so are expressly to be understood as non-limiting. By way of further illustration and not limitation, and as explained further below, any such thermoformable substrate may be coated on one or both sides or over its entire surface with a stretchable material (e.g., silicone with an elongation range). Furthermore, certain lateral areas of the apparatus are engineered not to stretch so as to maintain a minimum strength and rigidity value so that the apparatus will to some extent be load bearing in spite of other areas of the device being over-stretched on larger limbs and/or having relatively larger apertures or relatively greater "openness" so as to reduce the overall amount and weight of material and thus cost and improve breathability. Once again, it will be appreciated that such design objectives in various combinations and to various degrees may be accomplished, in whole or in part, in a variety of orthosis devices according to aspects of the present invention, such that the exemplary embodiment is to be understood as illustrative and non-limiting.

Turning now to FIG. 1, there is shown a perspective view of an exemplary embodiment of an orthosis apparatus 20 according to aspects of the present invention. The apparatus 20 comprises, in the exemplary embodiment, opposed first and second shell members 30, 60 that are selectively joined along common or adjacent edges, here as by opposed front and back zipper assemblies 90, 100, more about which is said further below, particularly in connection with FIG. 3. It will be appreciated as a threshold matter that the apparatus 20 as shown in FIG. 1 is in its formed and substantially rigid state after being molded or fitted to a patient, and thus in its malleable state being shaped and formed to substantially conform to such a patient's anatomy, again, here a lower leg, or ankle and foot area more particularly. In the detailed discussion below, there is described the method of forming such apparatus 20 into the "in use" condition shown in FIG. 1. There is again formed in each shell member 30, 60 a plurality of variable-shaped apertures to provide the desired degree and direction of stretch and by the same token improve breathability and weight-reduction characteristics of the apparatus 20. It will be appreciated that the attendant reduction in the total volume of material also translates to not only reduced cost but also reduced heating time when activating the apparatus 20 for forming or fitment during use. In a bit more detail, with reference to both FIGS. 1 and 2, in the exemplary embodiment each shell member 30, 60 is formed with at least three somewhat generally identifiable groups or regions of apertures: a leg or upper region of apertures 42, 72; a foot or lower region of apertures 44, 74; and an intermediate region of apertures 46, 76. While particular shapes and sizes of such apertures are shown, those skilled in the art will appreciate that such is merely illustrative and non-limiting and that a wide variety of shapes, sizes, and arrangements (locations, orientations, etc.) of such apertures is possible according to aspects of the present invention. It is also noted that such nomenclature is used interchangeably to identify individual apertures within a region or the region of apertures collectively. By way of further illustration and not limitation, the one or more shells 30, 60 and specifically the substrates 36, 66 thereof and the related aperture regions 42, 44, 46, 72, 74, 76 formed therein may be configured, in whole or in part, in any configuration or manner now known or later developed, including but not limited to any related disclosure in commonly owned U.S. Pat. No. 7,985,192 entitled "Geometrically Apertured Protective and/or Splint Device Comprising a Re-Mouldable Thermoplastic Material," incorporated herein by reference. Here, there is incorporated in each shell member 30, 60 a so-called "high stretch zone" as the respective first and second upper aperture region 42, 72 due to relatively large diamond-shaped apertures formed basically in the calf area of the respective first and second shells 30, 60 of the apparatus 20 down to the ankle. As will be appreciated, this provides a sizing solution wherein a relatively greater degree of stretch, particularly circumferentially, is made possible in the lower leg or calf area of the patient, where relatively greater anatomical variation across the population is typically seen, as will be further appreciated with reference to the below anatomic data presented in Table 2. By comparison, relatively smaller apertures 44, 46, 74, 76 are shown as being formed in the foot and ankle area of the apparatus 20, where relatively less anatomical variance is typically seen, for increased support and molding or shaping of the orthosis apparatus 20. More specifically, a further and different pattern or configuration of apertures is shown in the first and second lower aperture regions 44, 74 of the respective first and second shell members 30, 60, here shown as either smaller diamond- or square-shaped openings in the substrates 36, 66 and/or elongate somewhat rectangular openings. An optional first and second intermediate aperture region 46, 76 is further formed at the ankle area, here shown as a somewhat radial pattern of apertures configured and positioned to somewhat conform or correspond to the malleoli or ankle bone of the patient. Briefly, an optional toe box member 130 may be removably installed at the lower end 24 of the apparatus 20 to selectively cover and protect a patient's toes while providing selective access thereto, once again, more about which is said further below, particularly in connection with FIGS. 6 and 10 in connection with a first exemplary embodiment and with FIGS. 13, 17, and 18 in connection with a second exemplary embodiment.

Figure 2:
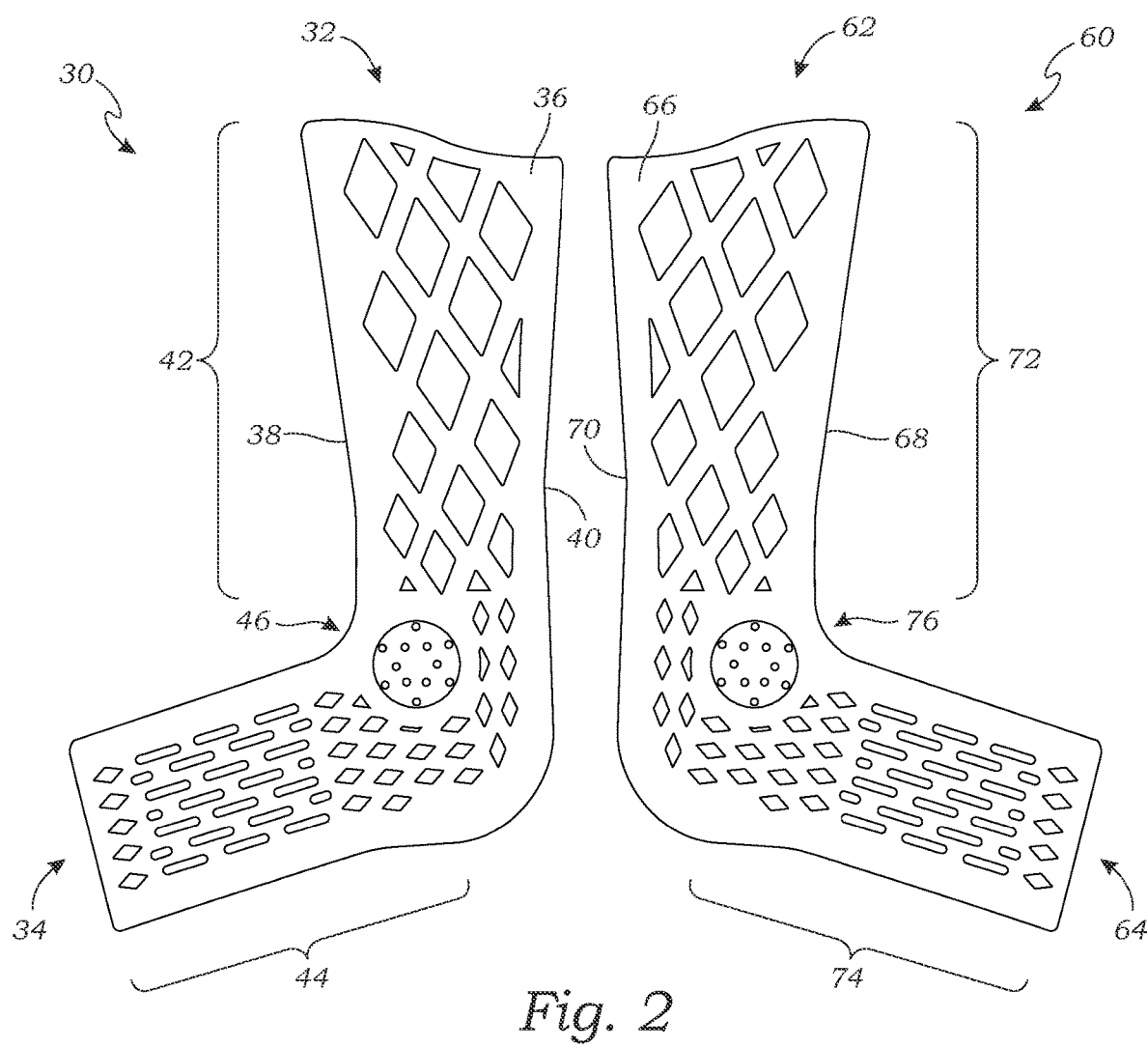
FIG. 2 is a side elevation view of opposed body members thereof in a pre-formed, unassembled state, in accordance with at least one embodiment.

With continued reference particularly to FIG. 2, there are shown side elevation or flat views of the first and second shell members 30, 60 in their flat or pre-formed state, as after manufacture but prior to use or even completed assembly of the exemplary orthosis apparatus 20. It will be appreciated that the shell members 30, 60 may be molded or formed into any desired shape, here again being substantially symmetrical, though such is not necessary, particularly in other contexts. In the illustrated AFO context, it will be further appreciated that by forming such shells 30, 60 effectively identically or as mirror images of one another, a single mold tool may be employed—of course, any appropriate manufacturing method now known or later developed may be employed instead of or in addition to such molding—and the resulting orthosis apparatus 20 having such symmetrical shells 30, 60 and being formable and customizable to the patient's anatomy may thus also be used on either a left or right limb, further reducing the number of such units in terms of size or configuration that would preferably be kept on hand or in stock. Those skilled in the art will note that the patterns of apertures 42, 44, 46, 72, 74, 76 depicted here varies slightly from those of FIG. 1, which may be attributable to the stretch and distortion the apertures may experience during shaping and forming for use of the apparatus 20 and is further representative of simply the variations such apertures can take consistent with aspects of the present invention. Accordingly, it will again be appreciated that the drawings are schematic in nature and are not to be taken literally or to scale in terms of material configurations, sizes, thicknesses, and other attributes of an apparatus 20 according to aspects of the present invention and its components or features unless specifically set forth herein. In the context of such molded or otherwise formed flat "blanks" of the first and second shell members 30, 60, the respective thermoformable substrate 36, 66 may be coated on one or both surfaces with a respective coating 56, 86 (FIGS. 21A-21C) such as silicone, polyurethane ("PU"), or any other such stretchable material now known or later developed. Those skilled in the art will appreciate that any such coating 56, 86 may be applied as by dipping (dip coating), spraying, over-molding, rolling, laminating, or any other such technique now known or later developed in the art so as to bond to, coat with, or otherwise install on the underlying substrate 36, 66 any such coating 56, 86. Relatedly, it will be appreciated that depending on the coating and the application technique, such may be on just one or both outwardly-facing side surfaces of the respective substrate or may completely cover the substrate, including the surfaces within the various apertures. Regardless, such coating would be applied as a relatively thin layer on the order of 80 microns in thickness. It is noted that a coating such as silicone or the like may serve to prevent sticking and to enable robust handling, heating, and application of the finished apparatus 20 in use. More particularly, those skilled in the art will appreciate that a thermoformable material such as may be employed as the substrate of each shell 30, 60 according to aspects of the present invention is typically like putty when heated and so would preferably have a material such as the proposed coating(s) on one or both sides to help maintain the overall shape and integrity of the shells 30, 60 even when heated and malleable.

In terms of the properties of the one or more shells 30, 60 forming an orthosis apparatus 20 according to aspects of the present invention, taking for example such a shell configuration comprising a thermoformable substrate 36, 66 such as made according to U.S. Pat. No. 7,985,192 having a silicone coating applied thereover as by dip-coating to a thickness of approximately 80 microns, the substrate itself having a nominal thickness of 5 mm, exemplary mechanical properties of such materials individually and collectively as an assembly as herein described are set forth below in Table 1.

TABLE 1

Mechanical properties of thermoformable substrate and/or coating material

| Property | Value Range | Optimum |
| --- | --- | --- |
| Elasticity range of coating material | 300% to 1300% | 500% |
| Modulus range of coating material @ 80° C. (force required to stretch a specified cross section in N/mm² by double (100% stretch)) | 0.17 n/mm2 to 5.6 N/mm2 | 2.5 N/mm2 |
| Operating temperature range of coating | −45° C. to 260° C. | −5° C.-130° C. |
| Thermal conductivity range of coating material | 0.0005 w/mk to 0.2 w/mk | 0.01 w/mk |
| Coating material thickness range (dry film) | 40 μm to 200 μm | 80 μm |
| Modulus range of substrate material @ 80° C. (force required to stretch a specified cross section in N/mm2 by double (100% stretch)) | 0.002 N/mm2 to 0.008 N/mm2 | 0.0029 N/mm2 |
| Modulus range of substrate and coating material together @ 80° C. (force required to stretch a specified cross section in N/mm2 by double (100% stretch)) | 0.003 N/mm2 to 0.1 N/mm2 | 0.055 N/mm2 |
| Activation temperature of the material/device (substrate and coating material together (e.g. 50° C. to 80° C.) | 50° C. to 80° C. | 70° C. |

Figure 3:
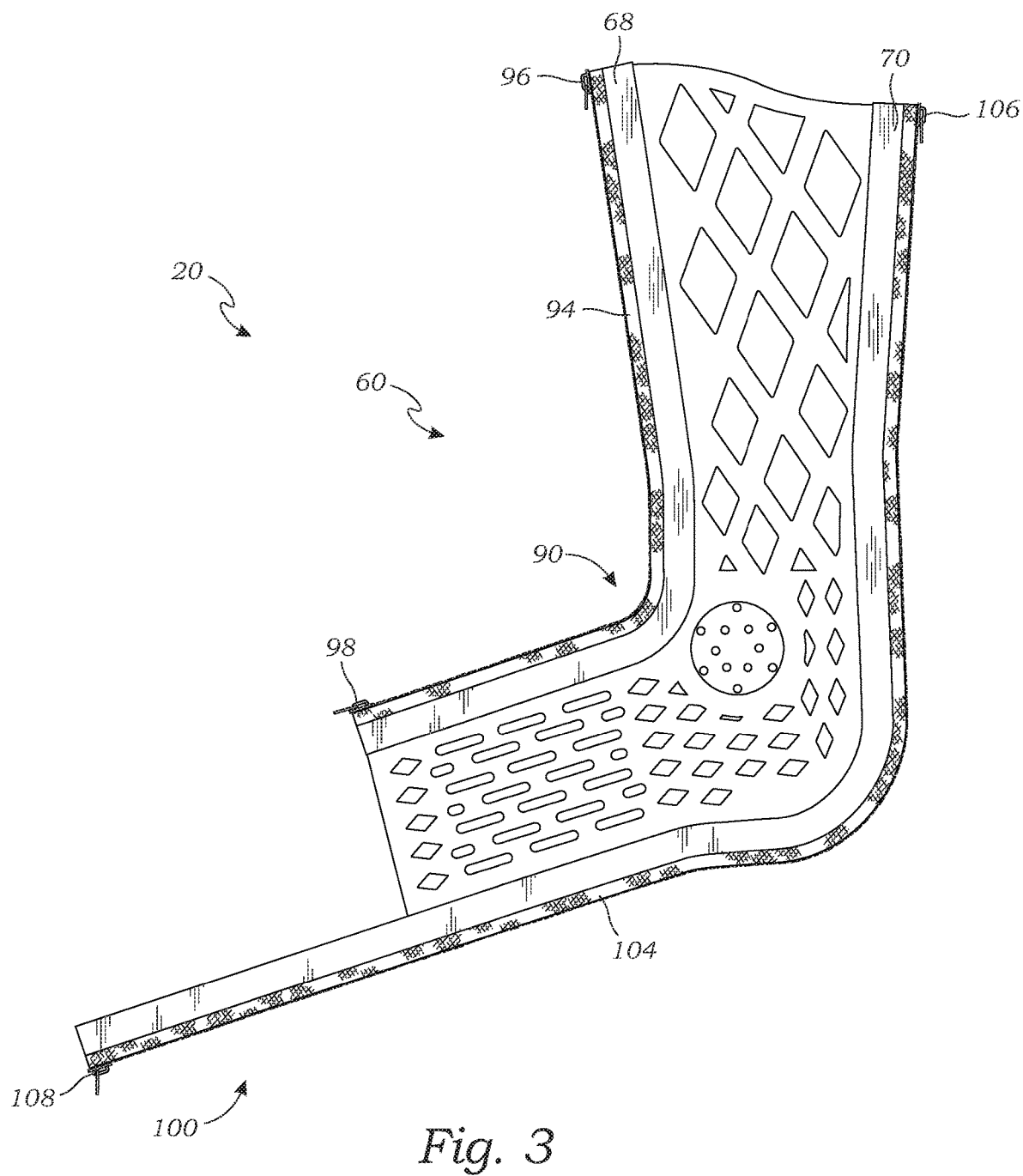
FIG. 3 is a side elevation view of opposed body members thereof in a pre-formed, assembled state, in accordance with at least one embodiment.
Figure 21A:
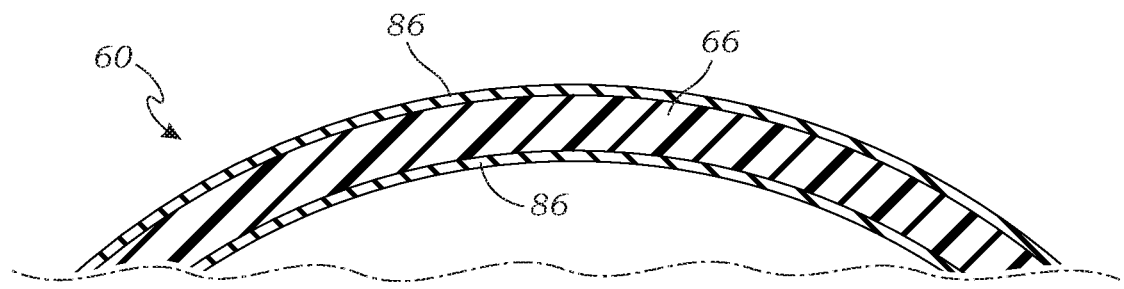
FIG. 21A is an enlarged sectional view taken from line 21A-21A in FIG. 10, in accordance with at least one embodiment.
Figure 21B:
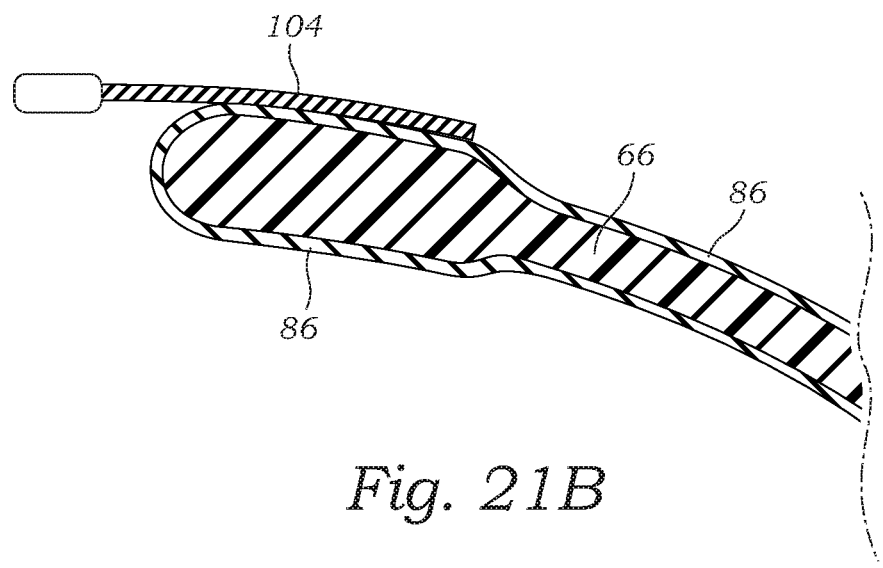
FIG. 21B is an enlarged sectional view taken from line 21B-21B in FIG. 10, in accordance with at least one embodiment.
Figure 21C:
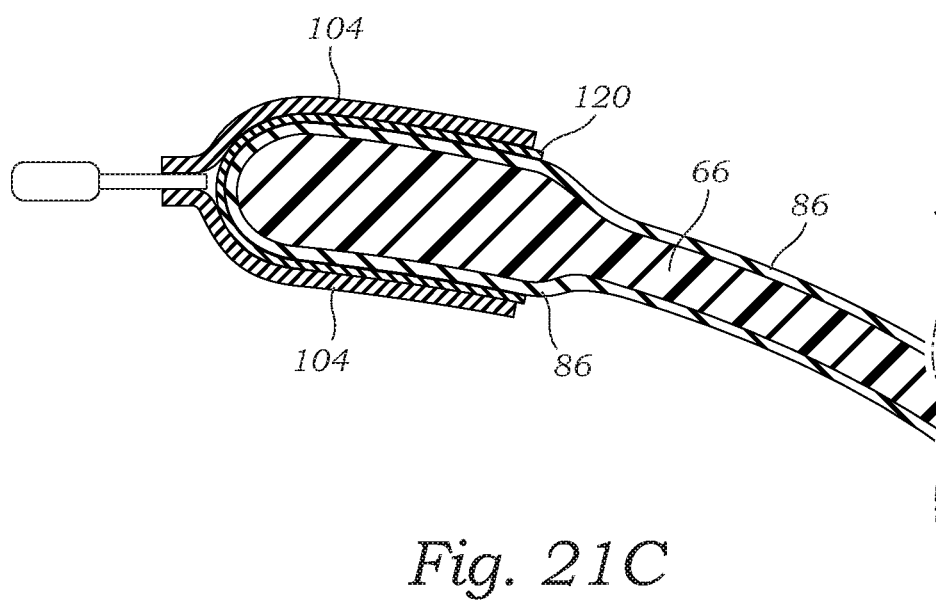
FIG. 21C is a further enlarged sectional view taken from line 21B-21B in FIG. 10, in accordance with at least one embodiment.

Referring still to FIGS. 1 and 2, and now with further reference to FIG. 3, an exemplary orthosis apparatus 20 according to aspects of the present invention is shown still in its flat or pre-formed state, with the respective first and second shell members 30, 60 now assembled as through the opposed front and back zipper assemblies 90, 100, thus here only the second shell member 60 being visible as being laid over on the first shell 30 from the orientation of FIG. 2, with the symmetrical second shell member 30 lying directly therebeneath in this view. Once again, one of the enablers of the improved functionality possible according to aspects of the present invention is the deployment of two zipper assemblies 90, 100 in the AFO apparatus 20, which solves a multitude of issues. The zipper assemblies 90, 100 are attached to the opposed shells 30, 60, whether the substrates 36, 66 themselves or any coating 56, 86 applied thereto (FIGS. 21A-21C). As a threshold matter, those skilled in the art will appreciate that while zippers are indicated as the means for fastening or selectively or temporarily assembling the two shells 30, 60 along the respective adjacent edges 38, 68, 40, 70, the invention is not so limited but may instead involve or employ, in any manner or combination, any fastener device now known or later developed, including but not limited to Velcro® hook-and-loop fasteners. Staying with the exemplary zipper fasteners, to enable selective opening and closing of the two shells 30, 60, the two zipper assemblies 90, 100 are attached to the shells 30, 60 to enable closure when applying on a patient and for opening of the apparatus 20 to provide access to or to remove or inspect the limb, which is very useful for diabetic foot conditions, for example. In more detail, each zipper assembly 90, 100 is generally formed as is known in the art with engageable, opposed and alternating zipper teeth carried on opposite strips 92, 94, 102, 104 that are then affixed typically along an edge of whatever substrate the zipper is to be installed and operate on. Here, with reference also to FIG. 1, the front zipper assembly 90 is positioned at the front of the apparatus 20 or across the top of the foot and up the front of the leg or shin and so has its first zipper strip 92 attached along the first front edge 38 of the first shell member 30 and has its second zipper strip 94 attached along the opposite second front edge 68 of the second shell member 60. Likewise, the back zipper assembly 100 is positioned at the back of the apparatus 20 or across the bottom of the foot, around the heel, and up the back of the leg or calf and so has its first zipper strip 102 attached along the first back edge 40 of the first shell member 30 and has its second zipper strip 104 attached along the opposite second back edge 70 of the second shell member 60. While zippers or other fasteners are shown as being under the foot and at the back of the leg and across the top of the foot and at the front of the leg, substantially opposite one another or roughly 180° apart, which has anatomical and use-related benefits as herein described, it will be appreciated that other locations and arrangements of such two or more zippers or the like may be employed according to aspects of the present invention without departing from its spirit and scope, noting that other offset arrangements of such closures would still provide the desired hinging and sufficient opening and access. As shown, each zipper assembly 90, 100 will have a zipper pull 96, 98, 106, 108 at each end for sizing adjustment; thus, in the exemplary embodiment, the orthosis apparatus 20 has two zipper assemblies 90, 100 and four zip openers or zipper pulls 96, 98, 106, 108, more about which is said below in connection with the apparatus 20 in use. A variety of methods now known or later developed may be employed in attaching the zipper assemblies 90, 100 to the respective shells 30, 60 as set forth herein, in part depending on the materials of construction thereof. In that regard, the zipper strips 92, 94, 102, 104 may be formed from any suitable somewhat flexible and inelastic or non-stretchable material now known or later developed, including but not limited to fabric or woven materials such as polyester or nylon or blends thereof, polyurethane ("PU"), or a silicone-coated textile, with the material optionally coated with a PU, silicone, or other elastomeric coating or the like to water-proof and improve wear of the zipper assemblies 90, 100. Furthermore, the zipper pulls 96, 98, 106, 108, one or more of which would be grasped during initial forming and fitment as when the product is heated and activated to be rendered malleable, and perhaps even the zipper teeth as well, which may also be contacted, can be coated or insulated to prevent burns or uncomfortable hot sensations when being deployed, as again by silicone or PU or other insulation material now known or later developed and suitable to such an application, particularly when such zipper components are made of metal or the like; to facilitate microwave heating of the apparatus 20, the zipper assemblies 90, 100 may contain no metal, but instead only plastics of various kinds. In one exemplary embodiment, the zipper assemblies 90, 100 are installed as by effectively bonding or embedding the respective zipper strips 92, 94, 102, 104 to or within any coating material 56, 86 applied to the shell substrates 36, 66 (FIGS. 21A-21C) when uncured. In a further exemplary embodiment, a two-sided pressure-sensitive adhesive ("PSA") tape 120 (FIG. 21C) may be employed between the respective zipper strips 92, 94, 102, 104 and the underlying shell edges 38, 40, 68, 70, whether such shells 30, 60 or the substrates 36, 66 thereof are coated or not. When a silicone coating is applied to the shells 30, 60, such PSA tape 120 may be formed having an acrylic or rubber-based side facing the zipper strips 92, 94, 102, 104 and a silicone side facing the silicone-coated shells 30, 60. If a PU elastomer coated shell 30, 60 is used, a rubber-based or PU-based side of the PSA tape 120 is affixed to the PU coated shell 30, 60 while the acrylic or rubber-based adhesive side is again facing the zipper strips 92, 94, 102, 104. Or alternatively, in a still further alternative exemplary embodiment, if a PU elastomer coated shell 30, 60 is used, a PU PSA tape 120 can be bonded to both the PU coated shell 30, 60 and the zipper strips 92, 94, 102, 104, as the PU PSA generally would stick to both such surfaces. In still further embodiments, velour tape with an adhesive backing may be applied at both edges 38, 40, 68, 70 of the respective shells 30, 60, with the zipper strips 92, 94, 102, 104 attached via a mushroom hook to the velour. Again, those skilled in the art will appreciate that any and all such attachment means now known or later developed may be employed according to aspects of the present invention without departing from its spirit and scope. By way of further illustration and not limitation, double-sided tape in a variety of forms, stitching, in-tool over-molding, hot melt, hot laminating, solvent or other bonding, ultrasonic welding, and/or Velcro® hook-and-loop fasteners may be employed in operably securing the zipper assemblies 90, 100 on the shells 30, 60.

Dimensionally, once more, for purposes of illustration, the orthosis apparatus 20 shown and described is nominally a "medium" sized AFO, but those skilled in the art will of appreciate that the apparatus 20 can simply be scaled up or down in the AFO context or otherwise to suit other nominal size requirements or contexts without departing from the spirit and scope of the invention, such as will be appreciated from the below information relating to both "small" and "large" sized AFO devices as well. But first, and staying with the AFO context for illustration, there are a number of anatomical factors relating to foot, ankle, and calf size across the adult population that bear on the geometry of the exemplary AFO apparatus 20 according to aspects of the present invention. The biggest areas that vary in sizing are the calf circumference relative to the circumference above the malleoli. (e.g., skinny ankle and large calf). The circumference at the ball of the foot is the next big variance, followed by the circumference over the malleoli heads.

Representative, relevant anatomic dimensions are shown below in Table 2. As will be appreciated, there needs to be significant overlap with the three proposed sizes of the orthosis apparatus 20 to cover roughly 95% of the target population. In practice, across the various sizes, to address the variances at all circumference regions, the various apertures 42, 44, 46, 72, 74, 76 are stretchable or collapsible/compressible as the orthosis 20 is manipulated while malleable such that it effectively can grow or shrink in diameter or in overall circumferential size at different locations along the length of body of the orthosis 20, particularly in the calf region where the apertures 42, 72 in the opposing shells 30, 60 are largest. In one exemplary metric, the resulting circumferential stretch of the apparatus 20 is up to 60%. Another way of expressing this attribute of such an orthosis apparatus 20 is its "openness," or the effective surface area that is open, or has an opening or perforation, as a percentage of the overall surface area of the device. Such openness, which is of course scalable or proportional across various sizes, is generally in the range of 20% to 45%, with the openness obviously being higher in the exemplary embodiment in the upper or calf region associated with apertures 42, 72, lower in the lower or foot region associated with apertures 44, 74, and likely lowest in the intermediate malleoli region associated with apertures 46, 76, though of course all such aspects being illustrative, and in any case the 20-45% range also being exemplary as an average openness across the entire orthosis apparatus 20. It will be further appreciated that such openness can vary not only as the product is scaled up or down in sizing but in use depending on the amount of stretch; here, then, the openness range generally represents the variance in openness across related AFO designs as both pre-formed (prior to use) and formed (during use).

TABLE 2

Indicative ankle, foot and calf anatomic dimensions (mm)

| | Anatomic Dimensions | Small | Medium | Large |
|---|---|---|---|---|
| A | Calf Circ | 315 | 360 | 395 |
| B | Above Malleo Circ | 190 | 210 | 220 |
| C | Ball of Foot Circ | 220 | 240 | 255 |
| D | Calf Height | 393 | 441 | 512 |
| E | Ankle Height (Lat) | 60 | 60 | 65 |
| F | Foot Length | 210 | 238 | 240 |
| G | Heel Breadth | 50 | 55 | 60 |
| H | Above Malleo Height | 110 | 120 | 130 |

As for representative dimensions of the exemplary AFO apparatus 20 according to aspects of the present invention, reference is made to the below Table 3 showing nominal formed shell or substrate dimensions as correlating to the anatomic measurements of Table 2, which circumferential dimensions it is noted are for the overall orthosis 20, or both shells 30, 60 as coupled together and formed and hardened in use as shown, for example, in FIG. 1, rather than the dimensions for a single shell. Again, in use, the circumferential dimensions may be varied by up to 60% for extreme cases in accommodating variety across the population. To address variance in leg length, it being observed herein that, while relatively significant circumferential stretch is achieved in the device by design (material and/or geometry), axial or lengthwise stretch of the orthosis apparatus 20 is limited particularly in connection with the reinforced lengthwise edges 38, 40, 68, 70 of the respective shells 30, 60 where the zippers 90, 100 are attached, the three sizes of the exemplary AFO device 20 were designed to the middle to high end of sizes across the population, which length can be adjusted down as needed by trimming or folding back excess material at one or both ends 32, 34, 62, 64 of the shells 30, 60, particularly the upper ends 32, 34. At the lower ends 62, 64, where the anatomic dimension in question is foot length, the variance of which is to be accommodated by configuring the AFO device 20 in each size range to the average or median foot length for the target population, then providing the apparatus 20 with the optional toe box 130, more about which is said below in connection with FIGS. 5 and 6 relating to the orthosis apparatus 20 in use. Where any trimming of the length of the apparatus 20—of either or both of the shells 30, 60 is involved, it will be appreciated that such cannot interfere with or adversely affect the operation of the closure system such as the opposing zipper assemblies 90, 100, which though not shown may be affixed and configured in such a way as to not extend to the marginal top and bottom shell edges to allow for such trimming and folding. Or, product length can be adjusted at top and bottom by adjusting the zippers 90, 100 back (i.e., slightly unzipping the zippers 90, 100 at one or both ends through the operation of the respective pulls 96, 98, 106, 108, with the material folded over the ends of the product on to itself; in such case an optional "band" or "comfort cuff" may be used to provide a smoother edge. In the context of the "medium" sized orthosis apparatus 20 according to aspects of the present invention, and by way of further illustration and not limitation, flat measurements such as of the shell 30, 60 in its pre-formed state as shown in FIG. 2 are an overall height of approximately 480 mm, an overall width of approximately 280 mm, a width at the upper end 22 of approximately 170 mm, and a width at the lower end 24 of approximately 110 mm. Staying with the exemplary "medium" sized orthosis, the effective inseam length along the selectively adjoining front edges 38, 68, which is essentially also the length of the upper zipper assembly 90, is approximately 490 mm, and the effective inseam length along the selectively adjoining back edges 40, 70, which is also the length of that portion of the back zipper assembly 100 attached to the shells 30, 60 at the back edges 40, 70, is approximately 635 mm, with the overall length of the back zipper assembly being 790 mm long, thus including a free portion of the back zipper assembly 100 that extends beyond the lower ends 34, 64 of the shells 30, 60 to accommodate selective installation of the toe box 130 as herein described. Where an exemplary toe box 130 as shown in FIG. 1 is employed, in its flat condition it may be approximately 100 mm wide by 140 mm long with its edges chamfered or rounded, for example. Once again, those skilled in the art will appreciate that all such dimensions are merely illustrative of features and aspects of the present invention and non-limiting.

TABLE 3

AFO combined substrate dimensions (mm)

| | Orthosis Dimensions | Small | Medium | Large |
|---|---|---|---|---|
| A | Calf Circ | 298 | 343 | 378 |
| B | Above Malleo Circ | 210 | 230 | 240 |
| C | Ball of Foot Circ | 203 | 223 | 238 |
| D | Calf Height | 393 | 441 | 512 |
| E | Ankle Height (Lat) | 65 | 65 | 70 |
| F | Foot Length | 230 | 258 | 260 |
| G | Heel Breadth | 60 | 65 | 70 |
| H | Above Malleo Height | 115 | 125 | 135 |

Figure 4:
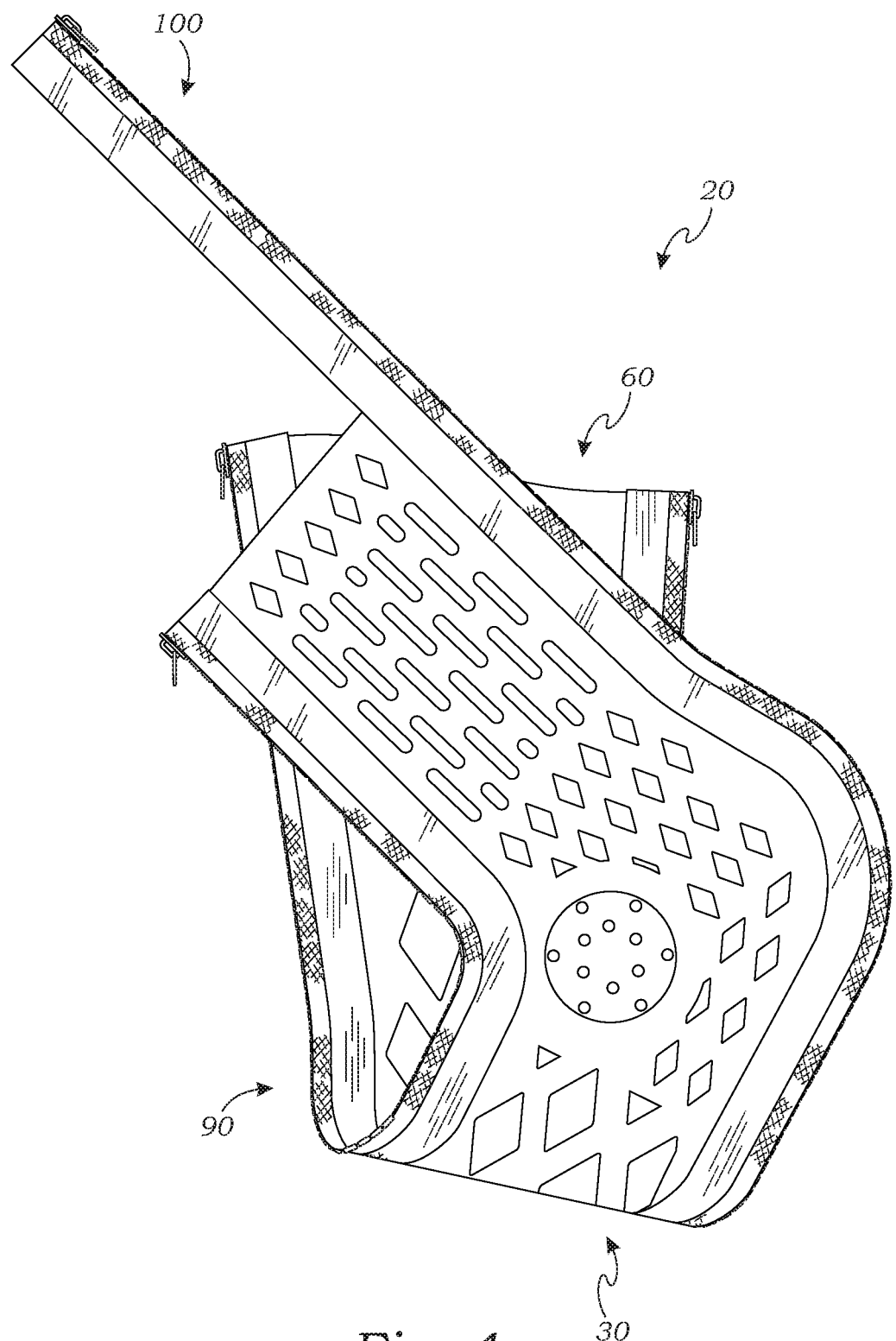
FIG. 4 is a side elevation view of opposed body members thereof in a pre-formed, assembled, folded state, in accordance with at least one embodiment.

Briefly referring to FIG. 4, once the exemplary orthosis apparatus 20 according to aspects of the present invention is assembled as shown and described in connection with FIG. 3, with the apparatus 20 thus still in its flat or pre-formed state, as part of the manufacturing process, the apparatus 20 may be flash or locally heated at an intermediate location so as to render such intermediate section formable, then bent at the formable section to effectively fold the product in half as shown, thereby reducing effectively by half the area or footprint required for the product 20 in packaging/shipment/ storage and for any microwave, dry heat oven, hot water bath or the like in which product 20 is heated in the field to render it formable (i.e., to activate the product for use). One objective in particular exemplary embodiments is to render the orthosis apparatus 20 relatively small, or even as small as possible, while remaining fit for its function, thus enabling a smaller heating system to be deployed (i.e. smaller foot-print, less energy consumption, faster heating time, etc.).

Figure 5:
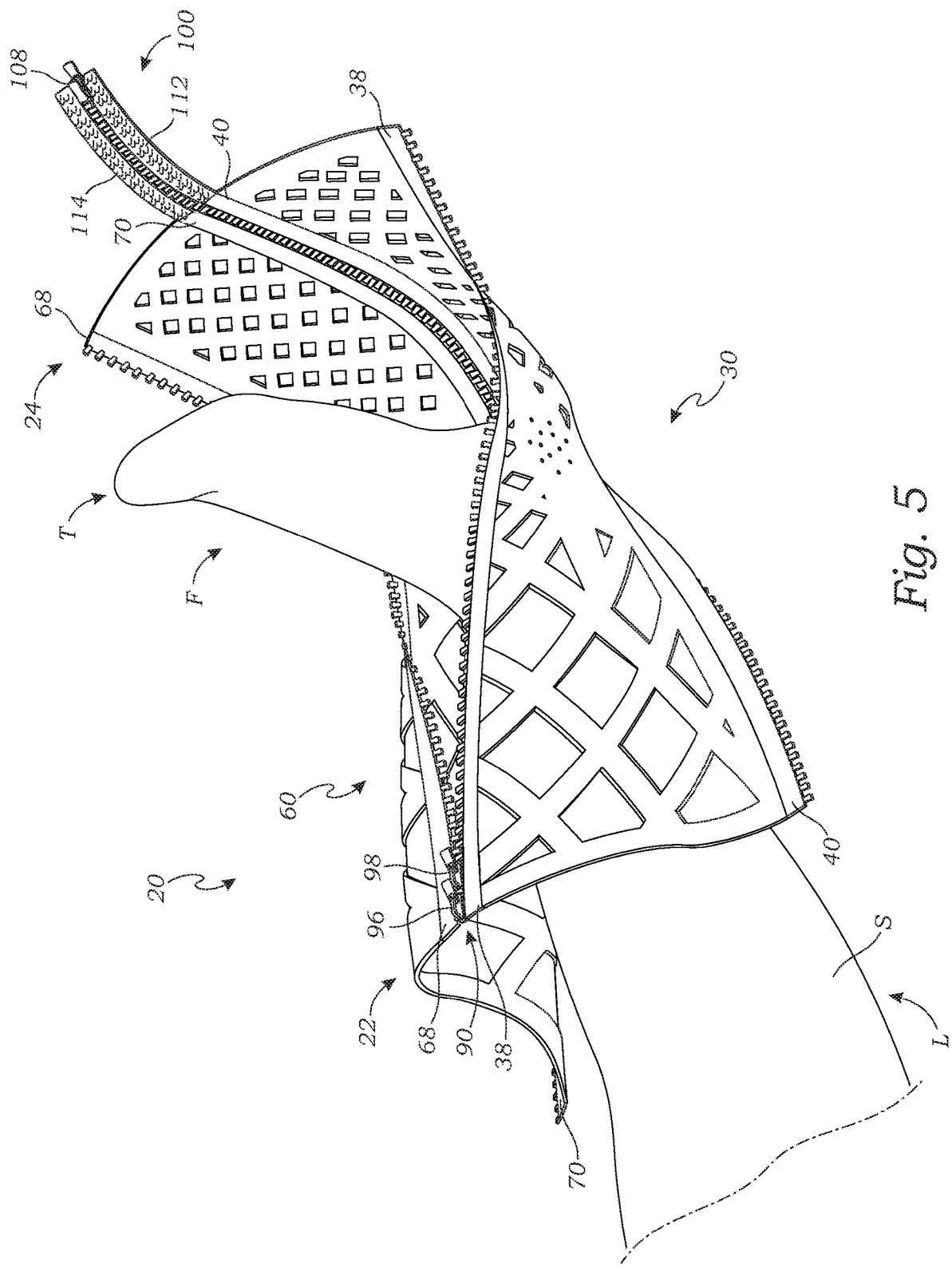
FIG. 5 is a perspective view thereof in an activated first operational mode, in accordance with at least one embodiment.
Figure 6:
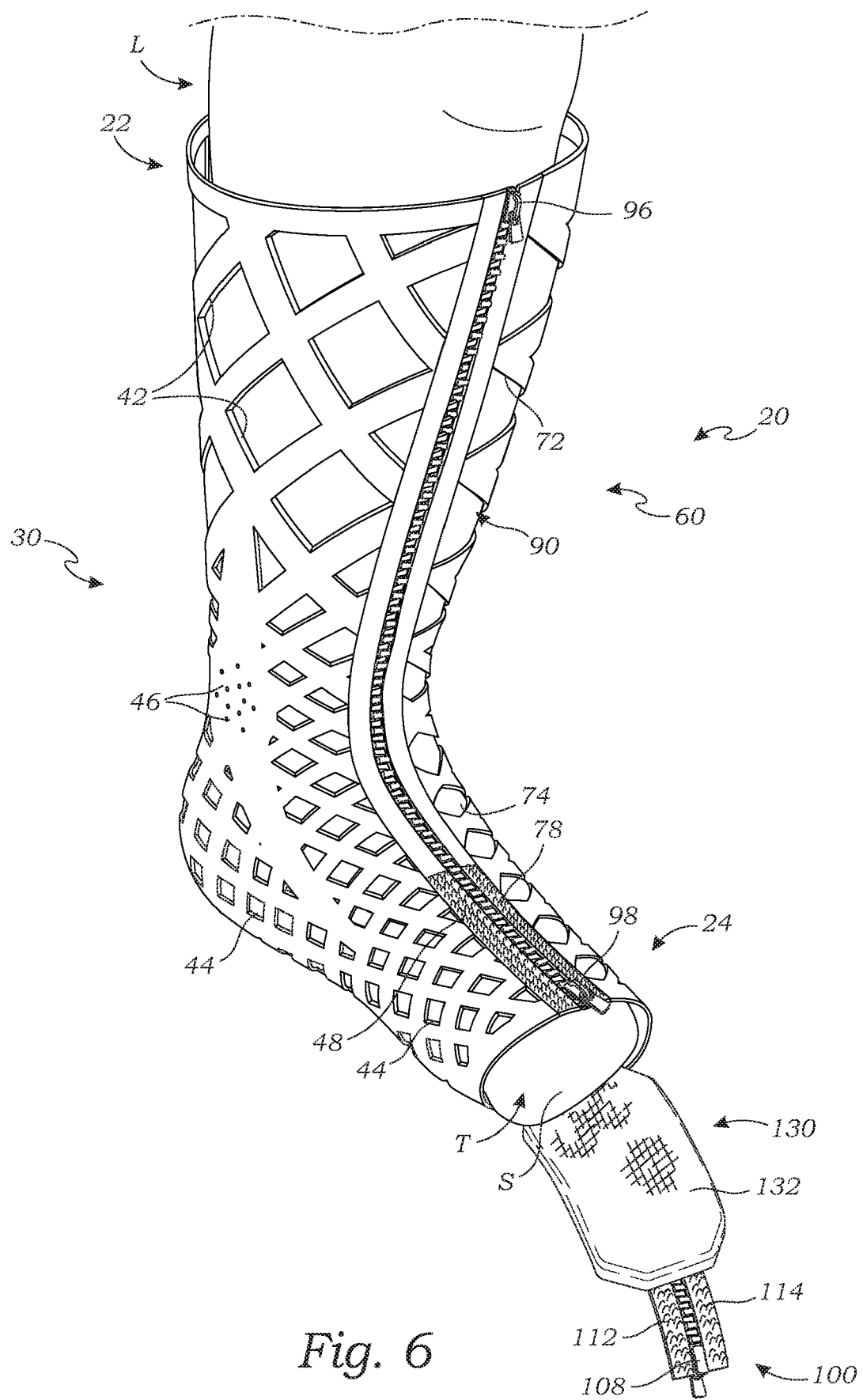
FIG. 6 is a perspective view thereof in an activated second operational mode, in accordance with at least one embodiment.
Figure 10:
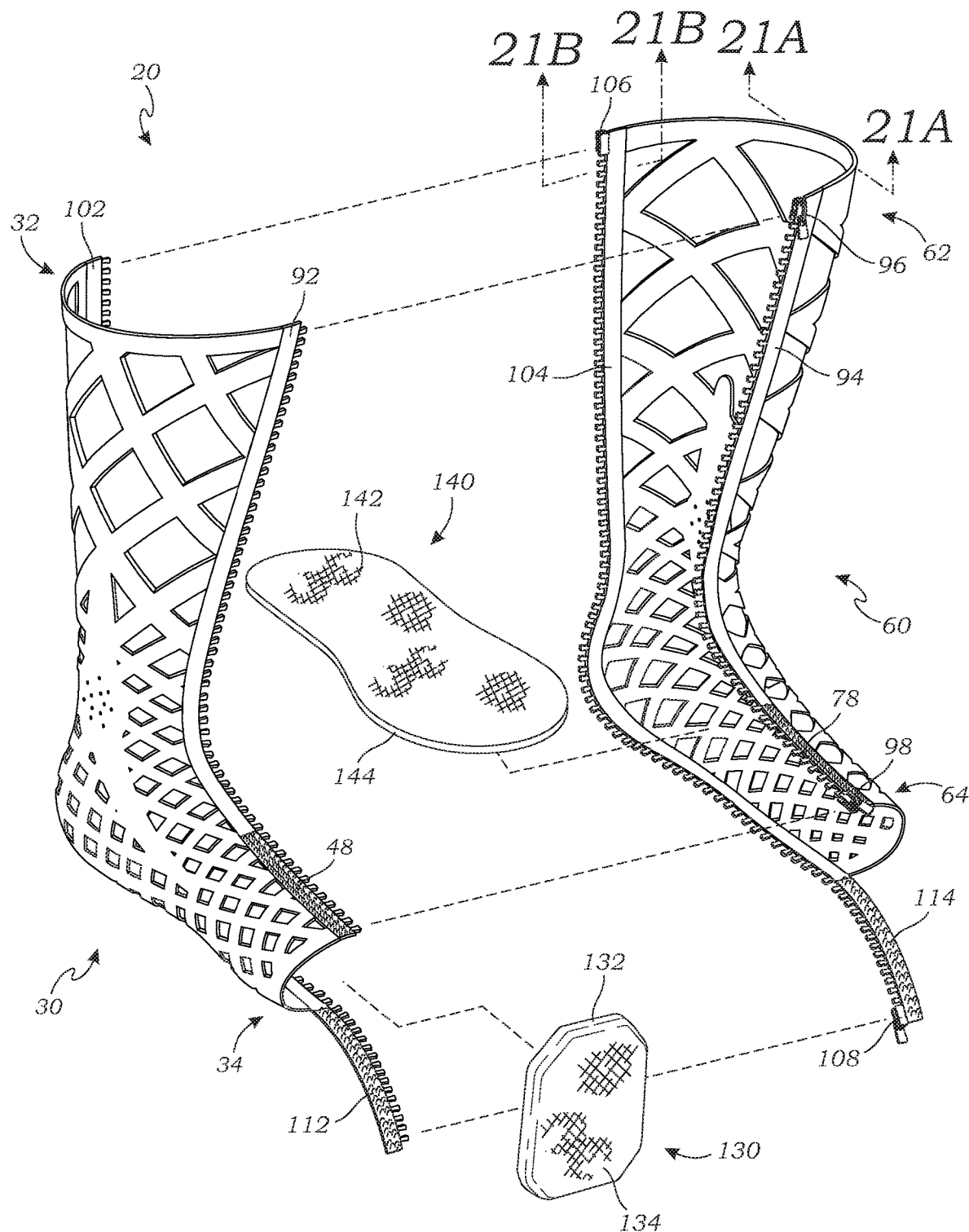
FIG. 10 is an exploded perspective view thereof, in accordance with at least one embodiment.

Turning next to FIGS. 5 and 6, there are shown perspective views of the exemplary AFO-type orthosis apparatus 20 according to aspects of the present invention in use. First, as seen in FIG. 5, with the apparatus 20 heated to a forming temperature such as in the range of 50-80° C., with further reference by way of illustration and not limitation again to U.S. Pat. Nos. 7,985,192 and 8,853,603, it is malleable and able to be draped over the limb to begin the fitment process. As an overview, the limb or area to be treated, here a lower leg L (ankle and foot area), is prepped as by applying a sock S thereover as shown or any other stocking, wrap, padding or the like as may be prescribed by the clinician. An optional inflation bladder 160 or cold therapy pad 170 may also be applied to the treatment site, more about which is said below in connection with FIGS. 11 and 12. The orthosis apparatus 20 is then heated employing any appropriate means, with the opposed flat shells 30, 60 zipped or attached together as shown in FIG. 3 or even as provided folded in half as shown in FIG. 4. Once activated, or heated and malleable, the back zipper assembly 100 is opened typically at least halfway down, such as to the region of the heel to facilitate easy application onto the limb (typically while the patient is sitting or lying down facing the clinician), it being appreciated that leaving the lower portion of the back zipper assembly 100 zipped forms a nest or bottom area of the orthosis 20 against which the foot F and any optional insole 140 (FIG. 10) may be seated as the upper end 22 is pulled proximally to position the orthosis 20 as shown in FIG. 6 (as such, the back top zipper pull 106 is not visible in the FIG. 5 view. The front zipper assembly 90 is shown as being substantially unzipped such that the front of the orthosis is effectively completely open, making it relatively easy to slip the foot F in effectively from the back, or to slip the orthosis 20 onto the foot F and leg L from the front or top (or above, once more, when the patient is seated facing the clinician with the leg L elevated), thus both the top and bottom front zipper pulls 96, 98 are shown as being positioned toward the upper end 22 of the apparatus 20, leaving just that end of the apparatus 20 connected in this operational mode, with the two flexible or malleable shells 30, 60 thus draped about the patient's leg L and foot F. An optional "double sided hook" or other such device now known or later developed may be employed to help maintain the AFO apparatus 20 upwards at this stage if needed. Again, with further reference to FIG. 10, if an optional insole 140 is employed, it is placed between the bottom of the patient's foot F and the bottom of the orthosis, more about which is said below but which it will be appreciated serves at the very least to provide additional padding between the bottom of the foot F and the bottom portion of the back zipper assembly 100. Alternatively, any such insole 140 may be affixed to the patient's sock S or other stocking or wrap in a manner known in the art. As shown, the insole 140 is substantially flat and foot-shaped having an upwardly-facing surface 142 that is to be oriented toward the foot F of the patient and an opposite downwardly-facing surface 144 that in use would be oriented toward the bottom of the orthosis 20 or against a portion or lower end section of the back zipper assembly 100 for comfort; as such, it will be appreciated that the insole 140 may be monolithic or formed from a single material throughout or may formed in layers or otherwise from two or more materials, such that the opposed upwardly-facing and downwardly-facing surfaces 142, 144 may not be the same material or construction, as will be further appreciated from the alternative exemplary insoles 140 shown and described below in connection with particularly FIGS. 24 and 25. Furthermore, though the insole 140 is shown as being flat and of a particular thickness, it will be appreciated that it may be thicker or thinner as desired and may be pre-formed with a prescribed shape, such as having an arch support area or heel well, or such topographical surface features may be formed in the insole 140 in use as herein described, such that the substantially flat configuration of the insole 140 as shown in FIG. 10 is to be understood as merely illustrative and non-limiting. If the insole 140 or the optional toe box 130 are made of a thermoformable material also, such would be heated along with the orthosis apparatus 20 to render them malleable as well prior to placement for optimum anatomical conformity. With the apparatus 20 and any optional accessories so positioned, the back zipper assembly 100 is substantially closed as by pulling the back top zipper pull 106 (FIG. 1) upwardly toward the upper end 22 of the orthosis 20. This causes stretch zones as formed by the apertures, particularly the upper apertures 42, 72, to stretch to allow the zipper 100 to fully close. Again, both zipper pulls 106, 108 at both ends can be adjusted back, or unzipped slightly, to allow folding of the ends 22, 24 to provide a comfort edge around the toes T and leg L as by setting the correct length below the knee. A wet wrap is then applied to cool and conform the AFO apparatus 20 as the apparatus 20 continues to be shaped by the clinician along and about the patient's leg L and foot F. To further aid in fitment, the patient may stand, applying slight pressure so as to ensure that the foot angle and position of the orthosis apparatus 20 is in the most comfortable position for the patient before it hardens and sets. Once hardened, the wet wrap is removed. Where a flexible toe box 130 is to be employed for selectively covering and protecting the toes T, such may be attached using Velcro® or any other removable engagement means now known or later developed to both the free end of the back zipper assembly 100 and to the top of the lower end 24 of the orthosis 20—in the exemplary embodiment as shown, first and second zipper strip fastener members 112, 114 are formed on the inside or upwardly facing surface of the free end of the back zipper 100 and similarly first and second shell fastener members 48, 78 may be formed or applied on the upwardly-facing lower end portion of the orthosis 20, one on each of the first and second shells 30, 60. It will be appreciated that the toe box 130 may itself be a hook-and-loop material, or have such swatches formed, on its inner and outer surfaces 132, 134 capable of selectively engaging both the zipper swatches 112, 114 and the orthosis swatches 48, 78 so that the toe box 130 may be selectively folded up and over the otherwise open lower end 24 of the orthosis 20 and held in position as shown in FIG.

1. It will be appreciated that in use such toe box 130 not only protects the toe region T but selectively provides access thereto by simply disengaging or detaching the toe box 130 and/or zipper 100 from the top of the orthosis 20, with any sock S or stocking perhaps not being present at all or at least also being open-toed so as to allow the clinician to inspect the toes for good circulation or other indicia of health without removal of the orthosis 20, which is particularly handy in cases where a security strap is employed. Optional straps may be applied for additional strength and security, as by wrapping about the orthosis 20 to prevent tampering or unauthorized removal. As to such security, a compliance strap such as disclosed in applicant's U.S. Pat. No. 8,821, 423, incorporated herein by reference, may be employed, which is a textile and Velcro® based strap. Alternatively, such a compliance strap may also be formed of a thermoformable material, heated to be rendered malleable along with the orthosis 20 and any other thermoformable components, placed around the cast and attached to itself, and then cooled to lock or form an integral ring about the orthosis 20 that can only be removed by destruction (e.g., cutting it off)—due to any silicone or other such coating on the shells 30, 60, the thermoformable compliance strap does not stick to the orthosis 20. If an inflation bladder 160 was fitted, it may be inflated/deflated to provide comfort and adjustment for swelling, more about which is again said below with reference to FIG. 11. To remove the exemplary AFO apparatus 20 as to evaluate the treated area or limb or administer therapy, for example, a clinician would simply unzip both zippers 90, 100 and remove the shells 30, 60, and to then refit or install the AFO 20, the shells 30, 60 are placed back in position and zipped back up. More specifically, to remove the device 20, the front zipper assembly 90 is fully opened and the back zipper 100 is opened downwards to the heel such that the two opposed shells 30, 60 may now hinge open to allow for easy insertion and removal of the limb while remaining connected as a single device 20 for easy refitting later.

Figure 7:
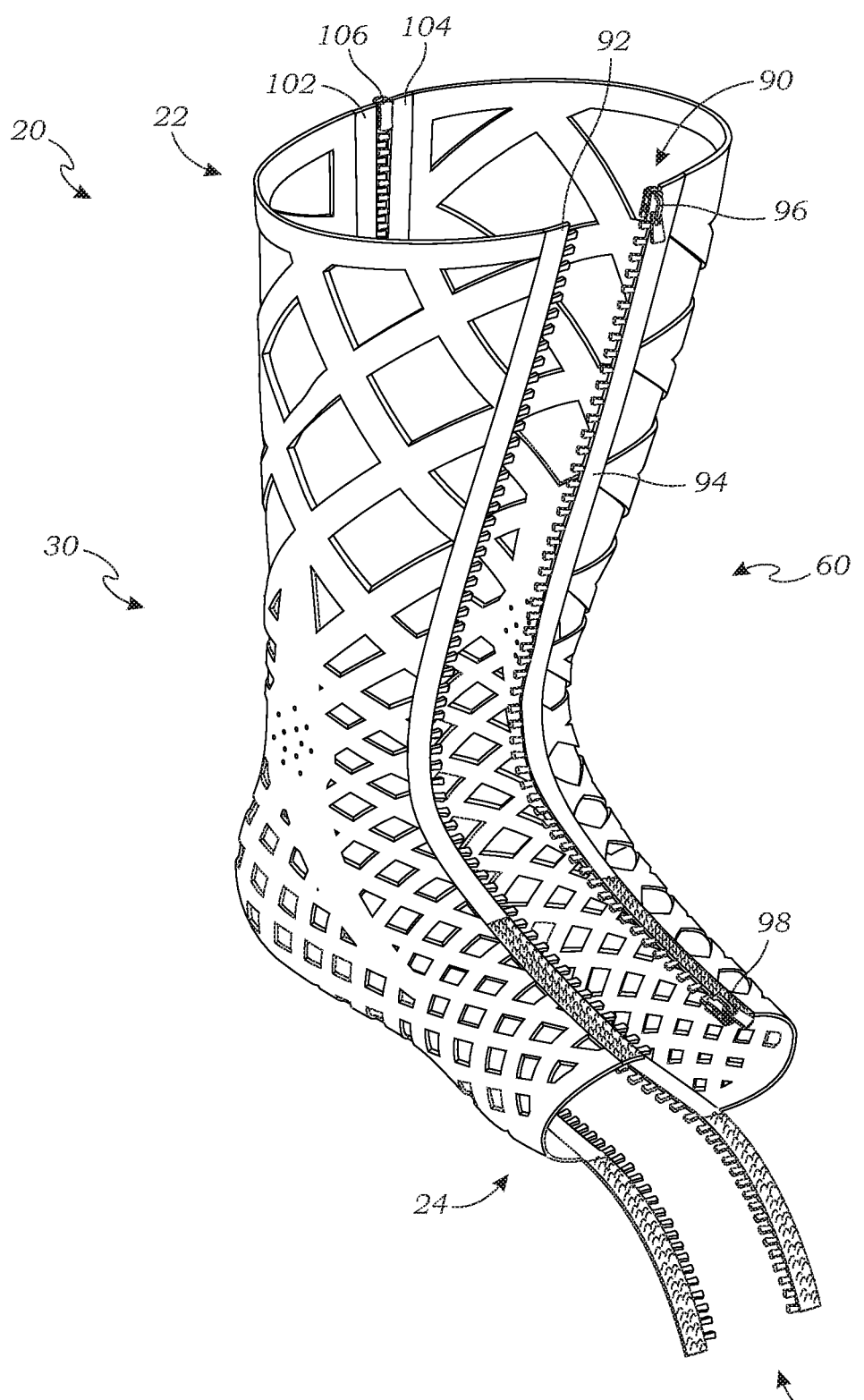
FIG. 7 is a perspective view thereof in a hardened third operational mode, in accordance with at least one embodiment.
Figure 8:
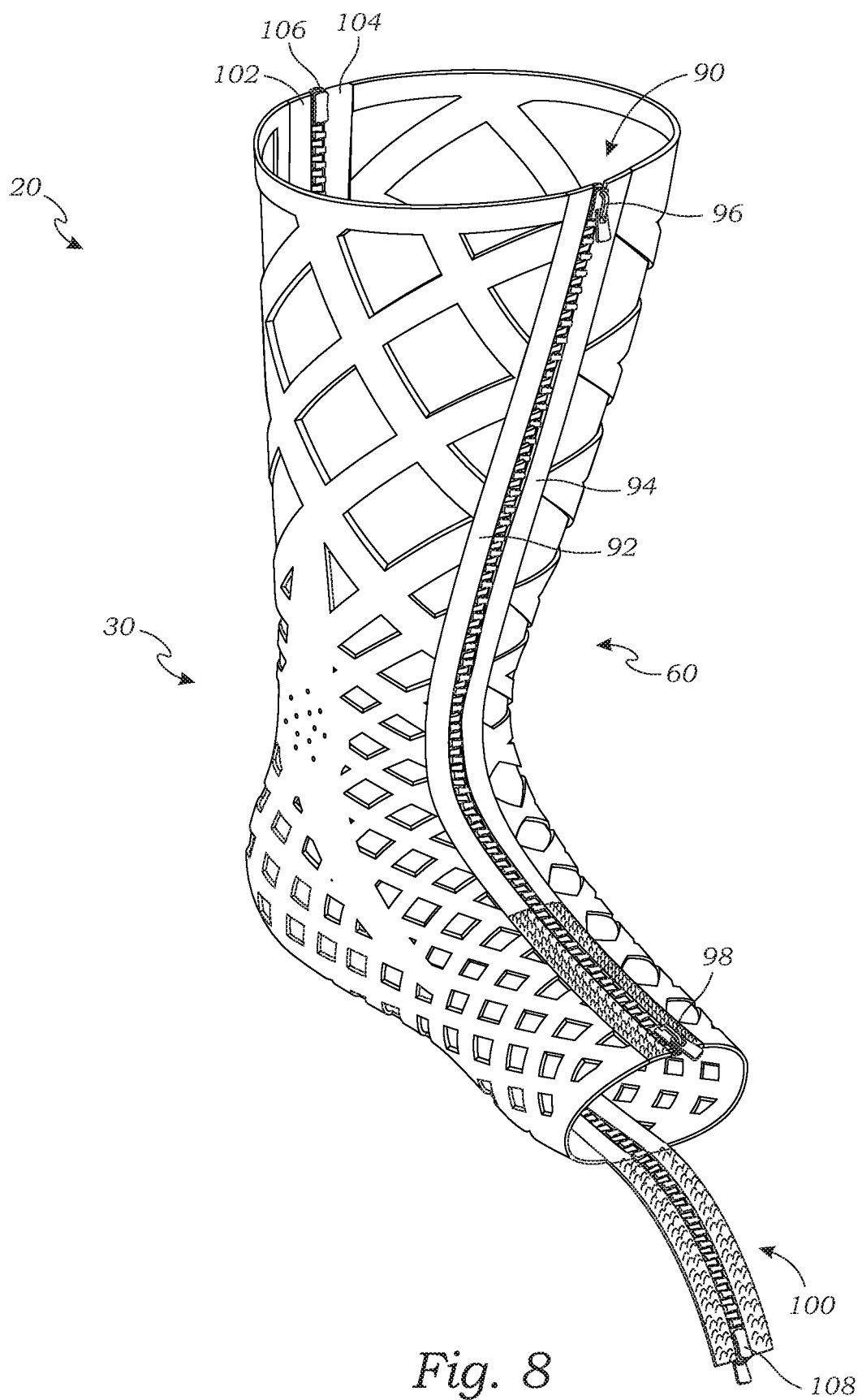
FIG. 8 is a perspective view thereof in a hardened fourth operational mode, in accordance with at least one embodiment.
Figure 9:
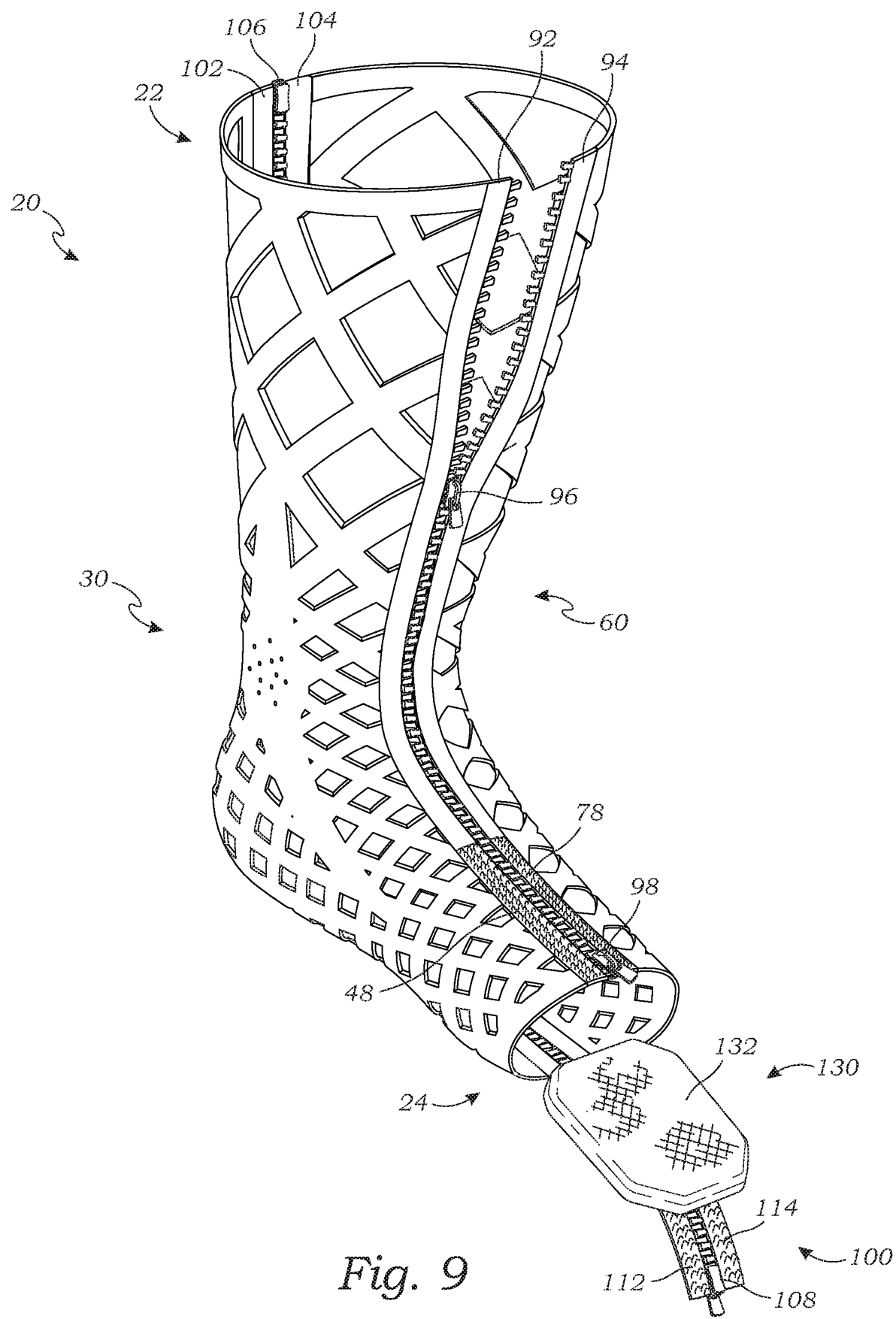
FIG. 9 is a perspective view thereof in a hardened fifth operational mode, in accordance with at least one embodiment.

Briefly, FIGS. 7-9 show the exemplary orthosis apparatus 20 according to aspects of the present invention in various other illustrative operational modes that are self-explanatory in light of the present specification.

In terms of the indications for use, once more, there is provided in the exemplary embodiment an ankle and foot device 20 generally for the post-operative & post-swelling treatment of ankle and foot fractures and other musculoskeletal injuries or conditions during the non-weight bearing and weight-bearing stages of healing. A standard cast shoe or a suitable walker boot can be fitted to the device 20 for weight bearing. The device 20 can be used to also treat fractures and other injuries or diabetic foot ulcers as a total contact cast as by employing the separate thermoformable insole 140 or the non-thermoformable insole 140 with attachable rocker 154 (though appreciating that in some embodiments the rocker 154 may be employed with an insole 140 that is thermoformable, in whole or in part). In one or more aspects, an orthosis apparatus 20 according to the invention is custom moldable, breathable, and removable/replaceable while having anatomical conformity at least equivalent to or better than below-the-knee fiberglass casts and able to meet or exceed the average strength of a weight-bearing fiberglass cast and/or walker boot. Comfort being an important factor for foot and ankle treatment because partial load is often exerted and complications can easily arise due to uncomfortable fitting casts, once again particularly in the context of diabetic foot ulcers. Furthermore, an orthosis apparatus 20 according to aspects of the present invention is relatively easy to use, requiring few steps to activate and apply in minimal time (including heating/activation time) and to remove and reapply as needed, with no cast saw needed at any stage. There is also the attendant benefit of reduced cost, both in initial fabrication by removing excess material, as by selectively placed stretch voids and having non-overlapping edges, and in that the device 20 is reusable, or able to be removed and reinstalled without being destroyed. It should also be noted, though not shown, that the orthosis 20 once formed may have a stretchable and breathable fabric cover attached or otherwise positioned on or over or within the orthosis 20. Such fabric may be Lycra™ elastic polyurethane fiber or fabric or any other such material now known or later developed. It will be appreciated that such a cover would help prevent dirt and debris from entering the orthosis 20 through any of the apertures therein, which may be particularly beneficial again in the DFU context where the patient may have lost some or all of the feeling in their feet and so may not feel such irritations caused by sand, gravel, and the like that could lead to a new ulcer site.

Such components and attributes of the exemplary orthosis apparatus 20 according to aspects of the present invention in construction and use as described herein are further shown in the exploded perspective view of FIG. 10. Generally shown once more are the two halves or shells 30, 60 of the apparatus 20 that are once more here configured to be substantially symmetrical. The front and back zipper assemblies 90, 100 are shown as separated for purposes of illustration, which may indeed be possible if the respective pulls 96, 98, 106, 108 could be zipped or slipped off at one end or the other. Though not shown, in another embodiment, and as is also known in the art, such zipper assemblies 90, 100 may be configured with zipper stops on one or both ends thereof to prevent the respective pulls 96, 98, 106, 108 from ever becoming disengaged from the zippers, which it will be appreciated would mean that at such a zipper end, the opposite edges of the respective shells 30, 60 could not be separated, as might be the case, for example for the upper end of the front zipper assembly 90 and the lower end of the back zipper assembly 100 as best shown in FIG. 5, versus the upper end of the back zipper assembly 100 and the lower end of the front zipper assembly 90 that are shown as being separated so as to temporarily allow a wider opening of the two shells 30, 60. Again, those skilled in the art will appreciate that other zipper configurations and other fastening means altogether, now known or later developed, may instead be employed in an orthosis apparatus 20 according to aspects of the present invention without departing from its spirit and scope. With continued reference to FIG. 10 and also to FIGS. 1 and 6, the exemplary toe box 130 is once more potentially formed as relatively heavy and wide hook material on both sides to have its lower or outer surface 134 attach to the hook fastener strips 112, 114 formed on the back side of the back zipper assembly 100 at is lower end and formed on the upper or inner surface 132 to attach to hook fasteners 48, 78 formed on the upper surface of the lower end 24 of the orthosis 20, or at the lower ends 34, 64 of the respective shells 30, 60. Alternatively, the toe box 130 could be a thermoformable material to which Velcro® swatches are affixed, such a thermoformable toe box being shaped as explained herein, and as further appreciated with respect to the alternative exemplary embodiment of FIGS. 13-22. Either way, it will be appreciated that in the exemplary embodiment, the extended zipper 100 on the lower end 24 of the AFO 20 facilitates attachment of the toe box 130 so that the zipper 100 is neatly anchored on the top side of the foot, which has several advantages in that the zipper would be uncomfortable if left on the sole of the foot, the zipper thereby assists in anchoring the toe box in position to protect the toes, and the zipper extension, alone or in combination with the toe box, facilitates the accommodation of different foot lengths and removes the need for trimming, which would make the zipper configuration relatively complex to allow for different foot lengths if trimmed also. For a total contact cast ("TOO") for diabetic foot ulcer treatment, the toe box 130 may again be made from a thermoformable substrate or other such material for increased durability, protection, and compliance, again, as will be further appreciated from the alternative exemplary embodiments disclosed herein.

Figure 11:
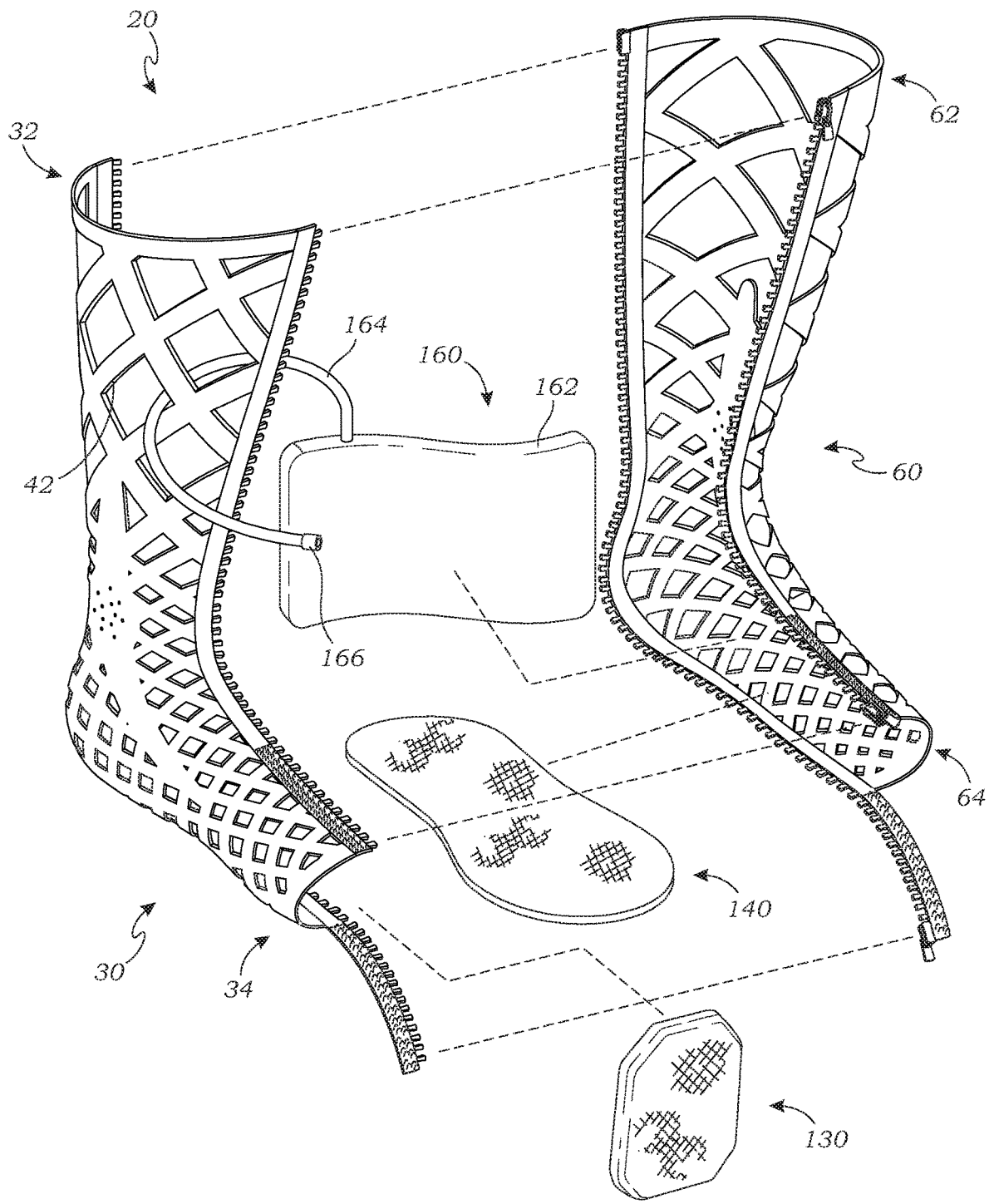
FIG. 11 is an exploded perspective view thereof in an alternative exemplary use, in accordance with at least one embodiment.

Referring next to FIG. 11, there is shown an exploded perspective view of a further exemplary orthosis apparatus 20 according to aspects of the present invention, again comprising opposite shells 30, 60 and here, as in FIG. 10, a toe box 130 and insole 140. Regarding the insole 140, such could be sized and configured to suit a range of standard adult feet (e.g., 95 percentile) and made of any appropriate padding material now known or later developed to space the patient's foot from the bottom of the orthosis 20, and particularly the lower zipper assembly 100. Alternatively, such an insole 140 as shown in FIGS. 10 and 11 may also be formed from a thermoformable material so as to allow molding and anatomic conformance with the foot, rendering the insole 140 and the base of the AFO apparatus 20 more generally a good fit and comfortable. By way of still further illustration and not limitation, the insole 140 could be made from a compressible material (e.g., foam or foam-like), an open cell foam or spacer fabric impregnated with a suitable thermoformable material, or any other such material that can be molded with the AFO apparatus 20 to take the shape of the foot and arches so that when cool it distributes the weight across the foot because the skin of the foot is in contact with the complete surface of the insole 140—pressure is distributed over the area of the foot—which is particularly useful for pressure distribution and pressure offloading of diabetic ulcers. In yet a further exemplary embodiment, the toe box 130 and the insole 140 may be formed Integrally as a single component inserted within the orthosis 20 and protruding out of the lower end 24 to wrap up and over the toes in use, again such unitary component being potentially formed of a thermoformable material or any other appropriate material now known or later developed. Relatedly, the toe box 130 may be formed so as to key or mate with the lower end 24 of the AFO apparatus 20, with it and the AFO 20 both being formed of moldable, thermoformable material to form an integrated and more rigid toe box 130. In such an embodiment, and by way of further example, there may be integrated a resistance wire into the toe box 130 perimeter so that the toe box 130 may be removed by connecting the wire to a 24 V DC or other such supply, which heats the wire and cuts through or softens the thermoformable or other material to allow removal of the toe box 130 in the alternative exemplary embodiment. With continued reference to FIG. 11, there is further shown an inflation bladder 160 positioned within or between the shells 30, 60. In practice, such bladder 160 shown as being substantially rectangular and flat, would be wrapped around the treated limb such as the leg L (FIG. 5) and positioned and secured where desired prior to placement of the orthosis 20 as herein described. The inflation line 164 leading from and in fluid communication with the body 162 of the bladder 160 would be of sufficient length and flexibility so as to be directed through one of the apertures in a shell of the orthosis 20, here illustrated as an upper aperture 42 in the first shell 30, and then fed or laid along the shell 30 when not in use and secured in any suitable manner now known or later developed. The free end of the inflation line 164 is shown as being configured with an inflation port 166 such as a one-way valve for selectively inflating or deflating the bladder 160 in use as by connecting the inflation line 164 to a vacuum or pressure source or regulated air supply, hand pump, or the like to selectively administer or allow the escape of air to set the desired pressure within the body 162 and thereby provide additional padding or increase or decrease the volume within the orthosis 20 for the affected limb such as to account for decreased or increased swelling without having to heat and in any way reform the orthosis apparatus 20. For the medium sized AFO 20 having dimensions as set forth herein, such a bladder 160, and specifically the body 162 thereof, may be approximately 300 mm wide by 150 mm high again with chamfered or radiused corners (e.g., radius of 20 mm). Once again, those skilled in the art will appreciate that such an orthosis apparatus 20 according to aspects of the present invention and related accessories can take a variety of other forms without departing from the spirit and scope of the invention, such that those shown and described are to be understood as merely illustrative and non-limiting.

Figure 12:
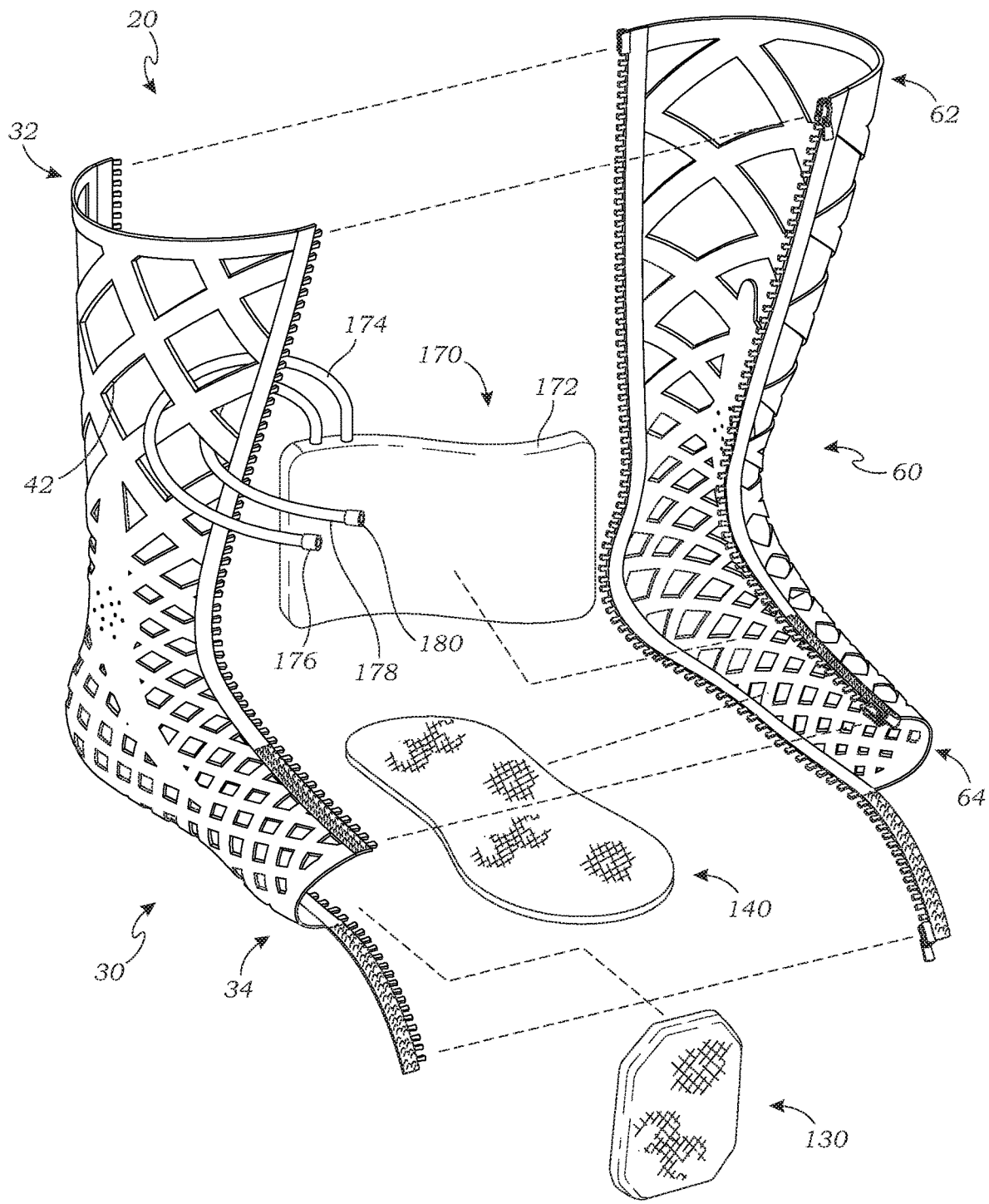
FIG. 12 is an exploded perspective view thereof in a further alternative exemplary use, in accordance with at least one embodiment.

Similarly, with reference to FIG. 12, there is shown an exploded perspective view of a further exemplary use of an orthosis apparatus 20 according to aspects of the present invention, such orthosis 20 again comprising opposite shells 30, 60 and here, as in FIGS. 10 and 11, a toe box 130 and insole 140. Here, rather than employing an inflation bladder 160 as shown in FIG. 11, a cold therapy pad 170 or other such treatment device may be selectively inserted and used in conjunction with the orthosis apparatus 20, here, to cool the underlying joint (skin) so as to reduce swelling and pain and promote recovery post-forming (once the apparatus is formed and hardened) in and around the treatment area, such as due to increased or decreased swelling and other physiological indications. The inlet and outlet lines 174, 178 of the cold therapy pad 170 as protruding from and in communication with the body 172 thereof are once again conveniently accommodated through the many apertures in device 20, here once more as extending through select one(s) of the upper aperture(s) 42 in the first shell 30, and then fed or laid along the shell 30 when not in use and secured in any suitable manner now known or later developed. The free ends of the inlet and outlet lines 174, 178 may be configured with any appropriate inlet and outlet connector 176, 180 for operable connection to any cold therapy device to circulate chilled coolant such as water through channels within the cold therapy pad body 172 to provide even cooling across the underlying joint/skin. Though only the inflation bladder 160 is shown in use in FIG. 11 and only the cold therapy pad 170 in use in FIG. 12, it will be appreciated that both may be used simultaneously depending on a number of factors, it being further appreciated that the openness of the device 20 can accommodate various numbers and kinds of devices and therapies, such that the exemplary uses are to be understood as illustrative and non-limiting. Furthermore, combining the features and functionality of such accessories, the cold therapy pad 170 may also be used (dual purpose) as an inflation bladder to accommodate anatomical variances post-forming as described above in connection with the stand-alone inflation bladder 160 of FIG. 11. When used as a cold therapy pad the pressure can be regulated to provide light pressure on the underlying joint/skin to ensure the AFO 20 fits snugly. And when the cold therapy pad 170 is disconnected from the cold therapy cooling device (not shown), valves on the inlet and outlet lines 174, 178 of the cold therapy pad 170 as incorporated into the respective connectors 176, 180 enable the cold therapy pad 170 to be inflated with air to provide light pressure on the underlying joint/skin to ensure continued anatomical conformity of the AFO apparatus 20. Once more, it will be appreciated that such an orthosis apparatus 20 according to aspects of the present invention and related accessories can take a variety of other forms without departing from the spirit and scope of the invention, such that those shown and described are to be understood as merely illustrative and non-limiting.

Figure 13:
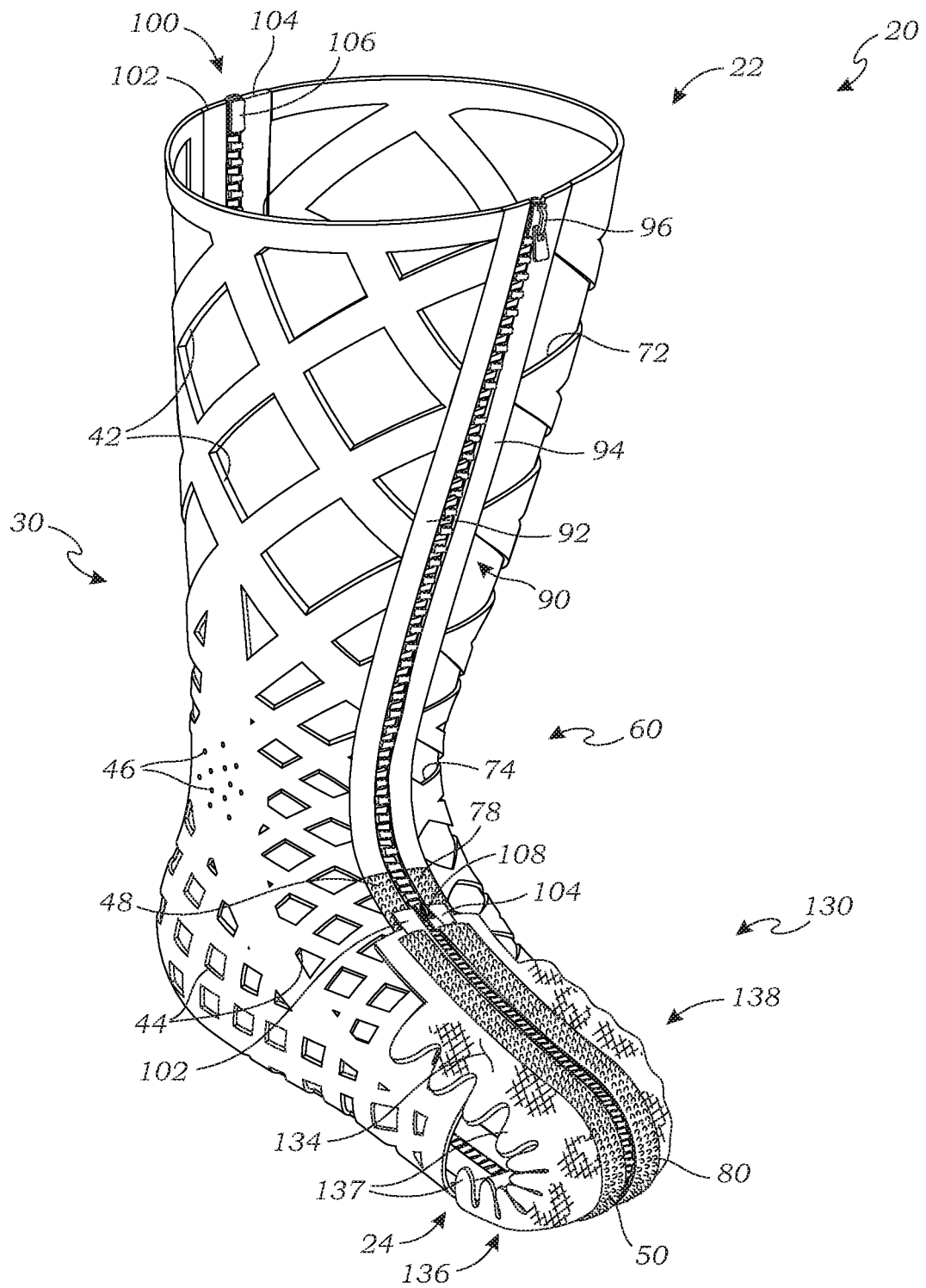
FIG. 13 is a perspective view of an alternative exemplary orthosis apparatus, in accordance with at least one embodiment.
Figure 15:
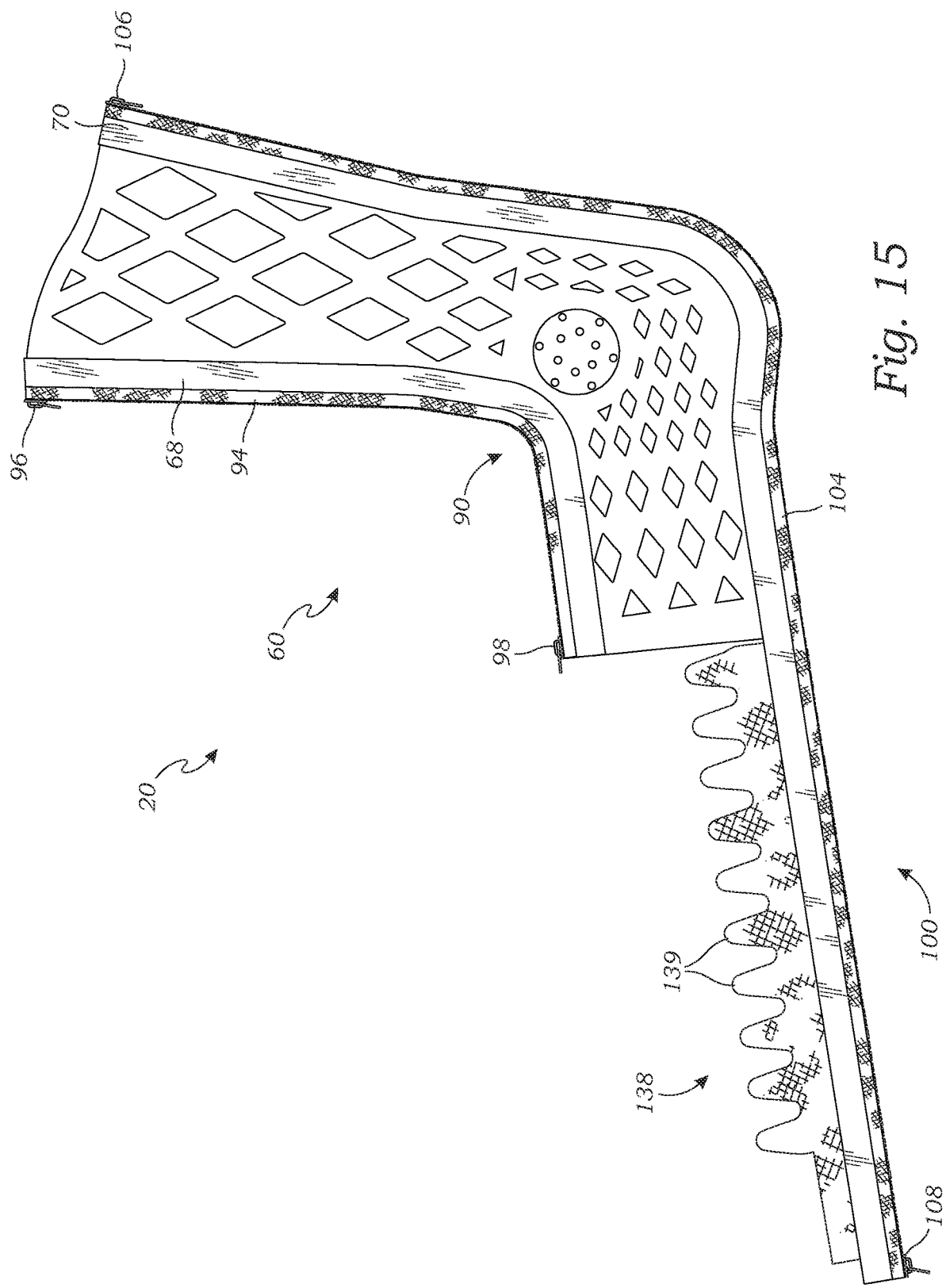
FIG. 15 is a side elevation view of opposed body members thereof in a pre-formed, assembled state, in accordance with at least one embodiment.
Figure 16:
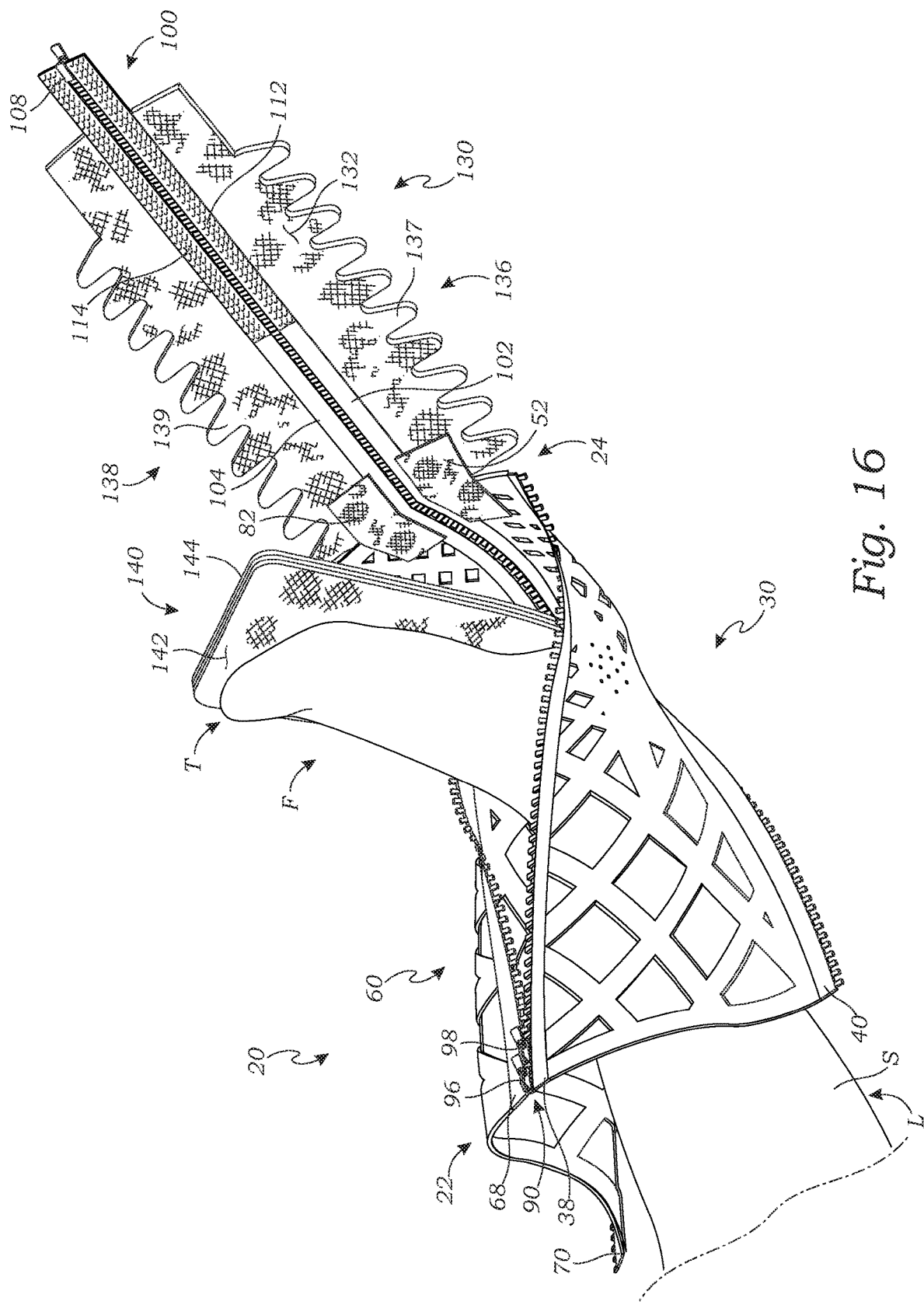
FIG. 16 is a perspective view thereof in an activated first operational mode, in accordance with at least one embodiment.

Turning now to FIG. 13, there is shown a perspective view analogous to that of FIG. 1, here of an alternative exemplary embodiment of an orthosis apparatus 20 according to aspects of the present invention. The apparatus 20 once again comprises opposed first and second shell members 30, 60 that are selectively joined along common or adjacent edges by opposed front and back zipper assemblies 90, 100, as described above, particularly in connection with FIGS. 3 and 5. Most notably, here, rather than the toe box 130 being a solid or single, somewhat rectangular piece of material that is removably engaged with the free or distally-extending lower end of the bottom or back zipper assembly 100, and specifically its opposite first and second Velcro®-type zipper strip fastener members 112, 114 affixed on the respective first and second zipper strips 102, 104 (FIG. 6), the toe box 130 is instead formed of two opposed sections or members 136, 138 that are affixed to or integrated on or with the respective first and second zipper strips 102, 104 to together form the toe box 130. In a bit more detail, the alternative exemplary toe box 130 is shown as comprising opposite first and second toe box members 136, 138 that extend somewhat laterally away from the back zipper assembly 100, again, as by being joined with the respective first and second zipper strips 102, 104, the means of which may include any joining or assembling technique now known or later developed in the art, including but not limited to double-sided tape in a variety of forms, stitching, in-tool over-molding, hot melt, hot laminating, solvent or other bonding, ultrasonic welding, and/or Velcro® hook-and-loop fasteners. As best seen in FIGS. 15 and 16, discussed below, the first and second toe box members 136, 138 may be initially fabricated as somewhat flat strips of material that are then formed into the desired shape subsequently. Indeed, the exemplary toe box 130, and specifically its first and second toe box members 136, 138, are here made of a thermoformable material as are the first and second shell members 30, 60 of the apparatus 20 itself, such that the toe box members 136, 138 would then be heated along with the orthosis apparatus 20 to render them malleable as well prior to placement for optimum shaping or molding and anatomical conformity, more about which is said below, particularly in connection with FIGS. 18A and 18B and the sizing capabilities of such an alternative exemplary toe box 130 and thus of the overall apparatus 20. Those skilled in the art will appreciate that by forming such a toe box 130 of thermoformable material that can not only be shaped for a proper anatomical fit but then once set or hardened will provide further structural integrity for the overall orthosis apparatus 20 and somewhat rigid protection of the patient's toes, another area of vulnerability particularly for diabetic patients that have lost some or all feeling in one or more toes that are thus susceptible to even unknown and untreated injury, there is thus provided an effective further alternative at the lower end 24 of the orthotic 20. With continued reference to FIG. 13, to facilitate forming the toe box 130 as by curving and bending the opposite first and second toe box members 136, 138 to the desired shape, the lateral edges of those members 136, 138, or the lengthwise edges opposite where each is joined or affixed on the respective first and second zipper strips 102, 104, may be formed with respective first and second protrusions 137, 139 (FIG. 15 as to second protrusions 139) extending substantially laterally away from the respective first and second zipper strips 102, 104. It will be appreciated that such "teeth" or protrusions 137, 139 and thus the space between them allows for the bending and curving of the toe box members 136, 138 while minimizing or eliminating bunching of excess material in the bends, as shown. While a particular size and shape and thus number of such protrusions 137, 139 are shown in the exemplary embodiment, those skilled in the art will appreciate that such may vary widely depending on a number of factors, such that once again it should be understood that the drawings are schematic in nature and not to be taken literally or to scale and, more generally, that all such exemplary embodiments are illustrative of features and aspects of the present invention but expressly non-limiting. By way of further illustration and not limitation, the protrusions 137, 139 may be lengthened or shortened, widened or narrowed, or positioned closer together or further apart as desired. It will be appreciated that in at least one exemplary embodiment the shape and spacing of the protrusions 137, 139 may be such that very little space is left between them when the first and second toe box members 136, 138 are formed into the desired shape, as a way of providing further protection of the toes while still having some breathability in the toe and ball of foot area as with the apertures 42, 44, 46, 72, 74, 76 formed in the first and second shell members 30, 60. Once again, a variety of such configurations of the toe box 130 and its first and second toe box members 136, 138 are possible according to aspects of the present invention without departing from its spirit and scope. With continued reference to FIG. 13, there is also shown on the outside of the bottom or back zipper assembly 100, along or overlapping a portion of both the first and second zipper strips 102, 104 and of the outer surfaces 134 of the toe box 130, or here of the opposite first and second toe box members 136, 138, opposite lengthwise strips of respective first and second attachment material 50, 80, which may run substantially the length of the back zipper assembly 100 at least from its distal end associated with the toe box 130 and along the entire underside of the apparatus shell members 30, 60 to and around the heel region. As will be appreciated with reference to FIGS. 18-22, a variety of non-slip or other such materials may then be selectively applied to the bottom of the orthosis 20 via such first and second attachment material 50, 80 from the toe to heel to facilitate walking about on the orthosis 20 even without a cast shoe, walker boot, or the like, again, more about which is said below.

Figure 14:
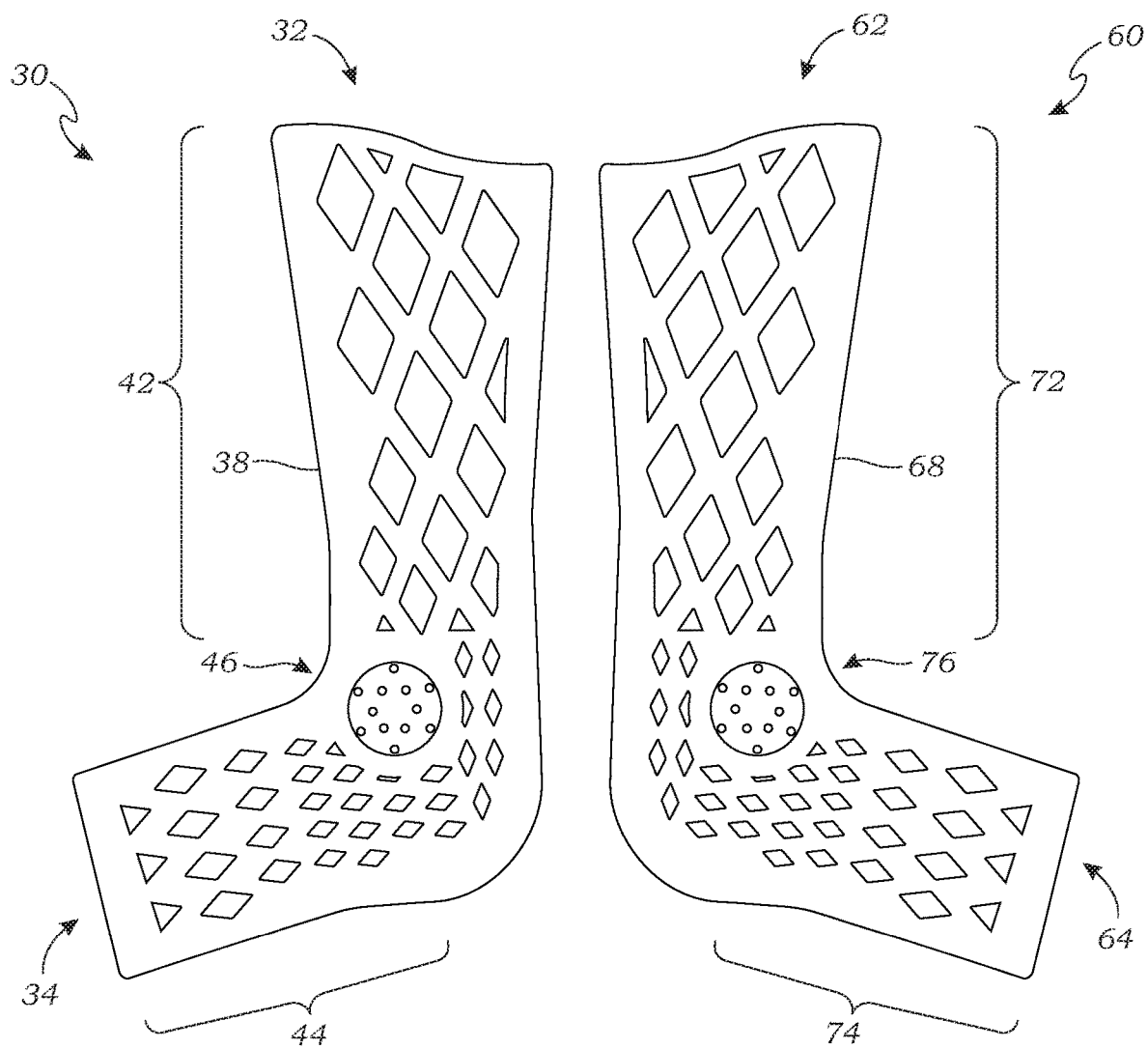
FIG. 14 is a side elevation view of opposed body members thereof in a pre-formed, unassembled state, in accordance with at least one embodiment.

Referring briefly to FIG. 14, analogous to FIG. 2, there are shown side elevation or flat views of the first and second shell members 30, 60 in their flat or pre-formed state, as after manufacture but prior to use or even completed assembly of the alternative exemplary orthosis apparatus 20 of FIG. 13. The shell members 30, 60 may again be molded or formed into any desired shape, here again being substantially symmetrical, though such is not necessary, particularly in other contexts, and employing any appropriate material now known or later developed, including but not limited to the illustrative thermoformable substrate 36, 66 that may be coated on one or both surfaces with a respective coating 56, 86 (FIGS. 21A-21C) such as silicone, polyurethane ("PU"), or any other such stretchable material now known or later developed. Here, it will be appreciated that while the area of the leg (calf and ankle) as relating to the first and second upper and intermediate aperture regions 42, 46, 72, 76 may be somewhat similar in size and configuration to that of the first exemplary embodiment of FIGS. 1 and 2, the area of the foot or the first and second lower aperture regions 44, 74 may be relatively shorter, allowing for more of the forefoot and toe region to be supported by the alternative exemplary toe box 130 (FIG. 13) and thereby allowing for relatively increased and/or easier size adjustment across the typical population, without the complication and inconvenience of trimming of any thermoformable material, which again presents particular challenges around the zipper assemblies 90, 100, more about which is again said below in connection with FIGS. 18A and 18B. Those skilled in the art will of course again appreciate that the relative sizes of the different regions 42, 44, 46, 72, 74, 76 in the exemplary AFO apparatus 20 may vary widely, as can the clinical applications beyond ankle-foot and thus the overall configuration of the apparatus 20 accordingly. As such, it will again be appreciated that the drawings are schematic in nature and are not to be taken literally or to scale in terms of material configurations, sizes, thicknesses, and other attributes of an apparatus 20 according to aspects of the present invention and its components or features unless specifically set forth herein. In the context of such molded or otherwise formed flat "blanks" of the first and second shell members 30, 60 and the exemplary "medium" sized orthosis apparatus 20 according to aspects of the present invention, and by way of further illustration and not limitation, flat measurements such as of the shell 30, 60 in its pre-formed state as shown in FIG. 14 are an overall height of approximately 480 mm, an overall width of approximately 280 mm, a width at the upper end 22 of approximately 180 mm, and a width at the lower end 24 of approximately 125 mm. Staying with the exemplary "medium" sized orthosis, the effective inseam length along the selectively adjoining front edges 38, 68, which is essentially also the length of the upper zipper assembly 90, is approximately 490 mm, and the effective inseam length along the selectively adjoining back edges 40, 70, which is also the length of that portion of the back zipper assembly 100 attached to the shells 30, 60 at the back edges 40, 70, is approximately 710 mm, with the overall length of the back zipper assembly 100 being approximately 910 mm long, thus including a free portion of the back zipper assembly 100 that extends beyond the lower ends 34, 64 of the shells 30, 60 to accommodate installation of the opposed first and second toe box members 136, 138 of the alternative toe box 130 as herein described, which toe box members 136, 138 would thus in the exemplary "medium-sized" embodiment have a flat or unformed length (as in the condition illustrated in FIG. 15) of approximately 200 mm, which is roughly the difference between the overall length of the back zipper assembly 100 of 910 mm and the effective inseam length along the selectively adjoining back edges 40, 70, which is also the length of that portion of the back zipper assembly 100 attached to the shells 30, 60 at the back edges 40, 70, of approximately 710 mm (i.e., 910 mm-710 mm). It will be appreciated that the two toe box members 136, 138 may be substantially coterminous with the distal end of the back zipper assembly 100 or may be short of that distal end to some extent, such that there is a portion of the back zipper assembly 100 that extends distally beyond the toe box 130, or the toe box members 136, 138 specifically, as shown elsewhere. Regarding the toe box members 136, 138, in one exemplary embodiment the overall lateral width of each is approximately 60 mm, roughly 15 mm of which may be the protrusions 137, 139. Once again, those skilled in the art will appreciate that all such arrangements and dimensions are merely illustrative of features and aspects of the present invention and non-limiting.

Turning next to FIG. 15, analogous to FIG. 3, the alternative exemplary orthosis apparatus 20 according to aspects of the present invention as shown in FIG. 13 is here shown still in its flat or pre-formed state, with the respective first and second shell members 30, 60 now assembled as through the opposed front and back zipper assemblies 90, 100, thus here only the second shell member 60 being visible as being laid over on the first shell 30 from the orientation of FIG. 14, with the symmetrical second shell member 30 lying directly therebeneath in this view. The zipper assemblies 90, 100 are attached to the opposed shells 30, 60, whether the substrates 36, 66 themselves or any coating 56, 86 applied thereto (FIGS. 21A-21C), though again other fastening devices and means for their attachment to the shells 30, 60, whether now known or later developed, may be employed. Here, with reference also to FIG. 13, the front zipper assembly 90 is again positioned at the front of the apparatus 20 or across the top of the foot and up the front of the leg or shin, and the back zipper assembly 100 is positioned at the back of the apparatus 20 or across the bottom of the foot, around the heel, and up the back of the leg or calf. Once more, while zippers or other fasteners are shown as being under the foot and at the back of the leg and across the top of the foot and at the front of the leg, substantially opposite one another, which has anatomical and use-related benefits as herein described, it will be appreciated that other locations and arrangements of such two or more zippers or the like may be employed according to aspects of the present invention without departing from its spirit and scope, noting that other offset arrangements of such closures would still provide the desired hinging and sufficient opening and access. Notably, in the alternative exemplary embodiment, each toe box member 136, 138 may be attached to its respective zipper strip 102, 104 employing any suitable means now known or later developed, again in much the same way that the zipper strips 102, 104 may be attached to or embedded in the respective shells 30, 60, particularly where the toe box members 136, 138 are formed of a thermoformable material, perhaps the same as or similar to that of the shells 30, 60. Accordingly, the back zipper assembly 100 may again be installed here on the opposed toe box members 136, 138 as by effectively bonding or embedding the respective zipper strips 102, 104 to or within any coating material applied to the toe box members 136, 138 when uncured. In a further exemplary embodiment, a two-sided pressure-sensitive adhesive ("PSA") tape may be employed between the respective zipper strips 102, 104 and the underlying edges of the toe box members 136, 138, whether such toe box members 136, 138 or the substrates thereof are coated or not. When a silicone coating is applied to the toe box members 136, 138, such PSA tape may be formed having an acrylic or rubber-based side facing the zipper strips 102, 104 and a silicone side facing the silicone-coated toe box members 136, 138. If a PU elastomer coated toe box member 136, 138 is used, a rubber-based or PU-based side of the PSA tape is affixed to the PU coated toe box member 136, 138 while the acrylic or rubber-based adhesive side is again facing the zipper strips 102, 104. Or alternatively, in a still further alternative exemplary embodiment, if a PU elastomer coated toe box member 136, 138 is used, a PU PSA tape can be bonded to both the PU coated toe box members 136, 138 and the zipper strips 102, 104, as the PU PSA generally would stick to both such surfaces. In still further embodiments, velour tape with an adhesive backing may be applied at the edges of the respective toe box members 136, 138, with the zipper strips 102, 104 attached via a mushroom hook to the velour. Again, those skilled in the art will appreciate that any and all such attachment means now known or later developed may be employed according to aspects of the present invention without departing from its spirit and scope. By way of further illustration and not limitation, double-sided tape in a variety of forms, stitching, in-tool over-molding, hot melt, hot laminating, solvent or other bonding, ultrasonic welding, and/or Velcro® hook-and-loop fasteners may be employed in operably securing the toe box members 136, 138 on the back zipper assembly 100 without departing from the spirit and scope of the invention. With continued reference to FIG. 15, those skilled in the art will once again appreciate that for the second toe box member 138 that is visible in this view, and thus the mirror-image first toe box member 136 (FIG. 13) that is positioned immediately and symmetrically beneath the second in the exemplary embodiment, each such toe box member 136, 138 is formed initially as a substantially flat and somewhat rectangular body having a straight edge along which the respective first and second zipper strips 102, 104 are joined and further having a plurality of laterally-extending, spaced-apart protrusions 137, 139 opposite of the respective first zipper strips 102, 104. As noted previously, the size and spacing and thus overall configuration of such protrusions 137, 139 may vary widely based on a number of factors, including the sizing of the overall orthotic 20 and its intended use, such that the exemplary protrusions 137, 139 are to be understood as illustrative and non-limiting. As also appreciated from the present side view of the unformed apparatus 20, there is shown a small gap between the proximal end of the toe box 130 and the body of the orthosis 20, here specifically the second toe box member 138 and the second shell member 60, which it will be appreciated facilitates the hinged movement of the toe box 130 relative to the body of the orthosis 20 as herein described as being at least about the back zipper assembly 100 as a "living hinge." In one exemplary embodiment, the gap between the toe box 130 and the body of the apparatus 20 is approximately 2 mm, though this is merely illustrative and non-limiting. While not shown, one or more additional breaks in the first and second toe box members 136, 138 to further facilitate flexing, hinging, or other articulation of even the formed toe box 130 are possible according to aspects of the present invention without departing from its spirit and scope.

Figure 17:
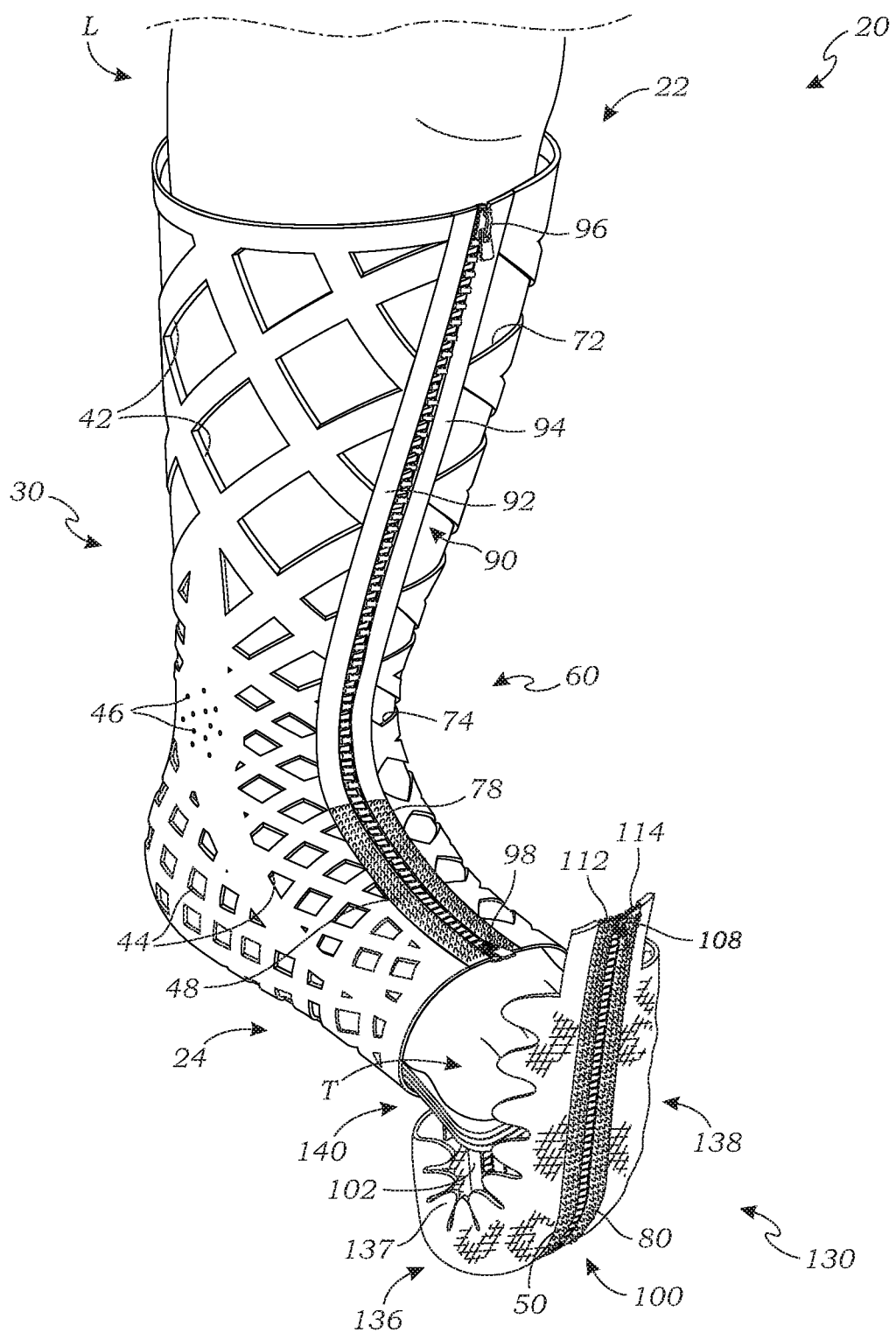
FIG. 17 is a perspective view thereof in an activated second operational mode, in accordance with at least one embodiment.

Shifting now to FIGS. 16 and 17 and the alternative exemplary orthosis apparatus 20 according to aspects of the present invention in use, analogous to the perspective views of the first exemplary embodiment of FIGS. 5 and 6, first, as seen in FIG. 16, with the apparatus 20 heated to a forming temperature such as in the range of 50–80° C., with further reference by way of illustration and not limitation again to U.S. Pat. Nos. 7,985,192 and 8,853,603, it is malleable and able to be draped over the limb to begin the fitment process, generally as described previously herein. The limb or area to be treated such as a lower leg L (ankle and foot area) is prepped as by applying a sock S thereover as shown or any other stocking, wrap, padding or the like as may be prescribed by the clinician. An optional inflation bladder 160 or cold therapy pad 170 may also be applied to the treatment site, more about which is said above in connection with FIGS. 11 and 12. Here, an insole 140 is also placed within the orthosis apparatus 20 beneath the patient's foot F as shown, generally in its unformed state. Where the insole 140 is also formed in whole or in part of a thermoformable material, more about which is said below in connection with FIGS. 23-26, the orthosis apparatus 20 together with the insole 140 may be heated employing any appropriate means, with the opposed flat shells 30, 60 zipped or attached together as shown in FIG. 15, or even as provided folded in half as shown an described in connection with the first exemplary embodiment of the apparatus 20 in FIG. 4. Once activated, or heated and malleable, the back zipper assembly 100 is opened typically at least halfway down, such as to the region of the heel to facilitate easy application onto the limb (typically while the patient is sitting down facing the clinician), it being appreciated that leaving the lower portion of the back zipper assembly 100 zipped forms a nest or bottom area of the orthosis 20 against which the foot F and the insole 140 may be seated as the upper end 22 is pulled proximally to position the orthosis 20 as shown in FIG. 17. Again, if an insole 140 is employed, it is placed between the bottom of the patient's foot F and the bottom of the orthosis 20, which it will be appreciated serves at the very least to provide additional padding between the bottom of the foot F and the bottom portion of the back zipper assembly 100. As shown, the insole 140 is initially substantially flat and somewhat foot-shaped having an upwardly-facing surface 142 that is to be oriented toward the foot F of the patient and an opposite downwardly-facing surface 144 that in use is oriented toward the bottom of the orthosis 20 or against a portion or lower end section of the back zipper assembly 100 for comfort; as such, it will be appreciated that the insole 140 may be monolithic or formed from a single material throughout or may formed in layers or otherwise from two or more materials, such that the opposed upwardly-facing and downwardly-facing surfaces 142, 144 may not be the same material or construction, as will be further appreciated from the alternative exemplary insoles 140 shown and described below in connection with particularly FIGS. 24 and 25. Furthermore, though the insole 140 is shown as being flat and of a particular thickness, it will be appreciated that it may be thicker or thinner as desired and may be pre-formed with a prescribed shape, such as having an arch support area or heel well. Alternatively, such topographical surface features may be formed in the insole 140 during use, or specifically during forming, as in the case where the insole 140, as with the toe box 130 and the orthosis halves 30, 60 themselves, is made of or comprises, at least in part, a thermoformable material. Here, such a thermoformable insole 140 would again be heated along with the orthosis apparatus 20 to render it malleable as well prior to placement for optimum anatomical conformity. Once the apparatus 20 including the toe box 130 and any optional accessories such as the insole 140 are so activated and positioned, the back zipper assembly 100 is substantially closed as by pulling the back top zipper pull 106 (FIG. 13) upwardly toward the upper end 22 of the orthosis 20, which causes stretch zones as formed by the apertures, particularly the upper apertures 42, 72, to stretch to allow the zipper 100 to fully close. Again, both zipper pulls 106, 108 at both ends can be adjusted back, or unzipped slightly, to allow folding of the ends 22, 24 to provide a comfort edge around the toes T and leg L as by setting the correct length below the knee. It is also at this stage that the clinician would fold or bend the activated, malleable toe box 130 comfortably around the toes T and back onto the apparatus as shown and described in connection with FIG. 13 in an illustrated position of the apparatus 20 and so affixed or held in that position as by removably mating or engaging the back first and second zipper strip fastener members 112, 114 formed on the underside of the respective first and second toe box members 136, 138, or more particularly on the respective back first and second zipper strips 102, 104, with the respective first and second shell fastener members 48, 78 formed on the upper side of the respective shell members 30, 60 on opposite sides of the front zipper assembly 90, or more particularly along the respective front first and second zipper strips 92, 94. Those skilled in the art will also appreciate in this context that should any portion of the activated, formable toe box members 136, 138 be in contact with the activated, formable shell members 30, 60, in an exemplary embodiment, due to any silicone or other such coating on the shells 30, 60 and/or the toe box members 136, 138 such components would not stick to each other, allowing for the hardened components to still move relative to one another, such as in selectively hinging the toe box 130 open as shown in FIG. 17 as by disengaging the tox box Velcro® swatches 112, 114 from the shell Velcro® swatches 48, 78. Here and generally across all embodiments, it is again noted that while Velcro® type "hook-and-loop" fasteners are shown and described, other fastening means now known or later developed may be employed. Moreover, in the Velcro® context the locations of the "hook" portions and "loop" portions may vary without departing from the spirit and scope of the invention. In the formed position of the apparatus 20 essentially as again shown in FIG. 13, as it continues to cool and set, but while still malleable, the patient may then stand on the affected foot F and leg L so as to further shape and form not only the apparatus 20 including the toe box 130 as they are manipulated exteriorly by the clinician, but also the interior insole 140 as it is effectively shaped along with the bottom of the apparatus 20 by the patient's anatomy and weight, in which way it is also ensured that the foot angle and position of the orthosis apparatus 20 is in a comfortable somewhat "neutral" position for the patient before it fully sets and hardens, as further appreciated with reference to FIGS. 18A and 18B. Those skilled in the art will thus appreciate that the resulting formed and hardened apparatus 20, including the toe box 130 and insole 140, substantially conforms to the patient's anatomy, here the leg L and foot F. In terms of fitment of the integrated thermoformable toe box 130, specifically, as best seen in FIG. 17, such is again curved or bent along its length, or along the opposed first and second toe box members 136, 138 to make such "toe box," with such bend location being set based essentially on the length of the patient's foot F and thus the position of the patient's toes T relative to the open lower end 24 of the apparatus 20, as well as any insole 140 that may be employed. The toe box 130 so formed, both initially during forming and then once hardened during use as when the toe box 130 is hinged open or closed as shown in FIG. 17, may again be selectively held in place on or relative to the body of the orthosis apparatus 20 employing a variety of means now known or later developed. In the exemplary embodiment, once more, first and second zipper strip fastener members 112, 114 are formed on the inside or upwardly facing surface of the free end of the back zipper assembly 100, or along opposite first and second zipper strips 102, 104 at the distal end of the zipper assembly 100, and similarly first and second shell fastener members 48, 78 are formed or applied on the upwardly-facing lower end portion of the orthosis 20, one on each of the first and second shells 30, 60, or specifically along opposite front first and second zipper strips 92, 94. It will be appreciated that the toe box 130 may itself be a hook-and-loop material, or have such swatches formed, on the inner surfaces 132 of the opposite first and second toe box members 136, 138 capable of selectively engaging the orthosis swatches 48, 78 so that the toe box 130 may be selectively folded up and over the otherwise open lower end 24 of the orthosis 20 and held in position as shown in FIG. 13. Alternatively, the toe box 130 may be formed comprising opposite first and second toe box members 136, 138 made of a thermoformable material to which Velcro® swatches are affixed, such a thermoformable toe box being shaped as explained herein. Either way, it will be appreciated that in the exemplary embodiment, the extended zipper 100 on the lower end 24 of the AFO 20 facilitates attachment or integration of the toe box 130 so that the zipper 100 is neatly anchored on the top side of the foot F in use as shown in FIG. 13, which has several advantages in that the zipper would be uncomfortable or subject to damage, particularly as to its one or more pulls 106, 108, if left on the sole of the foot, the zipper 100 thereby assisting in anchoring the toe box 130 in position to protect the toes T, and the zipper extension 100 in combination with the toe box 130 facilitates the accommodation of different foot lengths and removes the need for trimming, which would make the zipper configuration relatively complex to allow for different foot lengths if trimmed also. For a total contact cast ("TCC") for diabetic foot ulcer treatment, the toe box 130 being made from a thermoformable substrate or other such material again provides increased durability, protection, and compliance. Relatedly, it will be appreciated that in use such toe box 130 not only protects the toe region T but selectively provides access thereto by simply disengaging or detaching the toe box 130 and/or zipper 100 from the top of the orthosis apparatus 20, the alternative toe box 130 otherwise remaining engaged with the apparatus 20 and effectively hinging about the back zipper assembly 100 and any optional strips or patches of first and second reinforcing material 52, 82 applied over or spanning the bottom joint between the shell members 30, 60 and the respective first and second toe box members 136, 138, which it will be appreciated not only provides further structural integrity at the hinge, particularly against any twisting between the toe box 130 and the first and second shells 30, 60 about the back zipper assembly 100, but also renders the joint between such shells 30, 60 and the toe box 130 relatively "seamless" and more comfortable, particularly in cases where no insole 140 is employed. Again, those skilled in the art will appreciate that selective opening and closing of the integrated toe box 130 as by hinging about the base of the orthosis 20 at its lower end 24 so as to selectively open such end 24 allows the clinician to inspect the toes T for good circulation or other indicia of health without removal of the orthosis 20, which is particularly handy in cases where a security strap 190 is employed, more about which is said below in connection with FIG. 22. If an inflation bladder 160 was fitted, it may be inflated/deflated to provide comfort and adjustment for swelling, more about which is again said above with reference to FIG. 11. To remove the exemplary AFO apparatus 20 as to evaluate the treated area or limb or administer therapy, for example, a clinician would simply unzip both zippers 90, 100 and remove the shells 30, 60, and to then refit or install the AFO 20, the shells 30, 60 are placed back in position and zipped back up. More specifically, to remove the device 20, the front zipper assembly 90 is fully opened and the back zipper 100 is opened downwards to the heel such that the two opposed shells 30, 60 may now hinge open to allow for easy insertion and removal of the limb while remaining connected as a single device 20 for easy refitting later, including with the hinged toe box 130 and any insole 140 nested in the closed zipper region at the base of the foot.

Figure 18A:
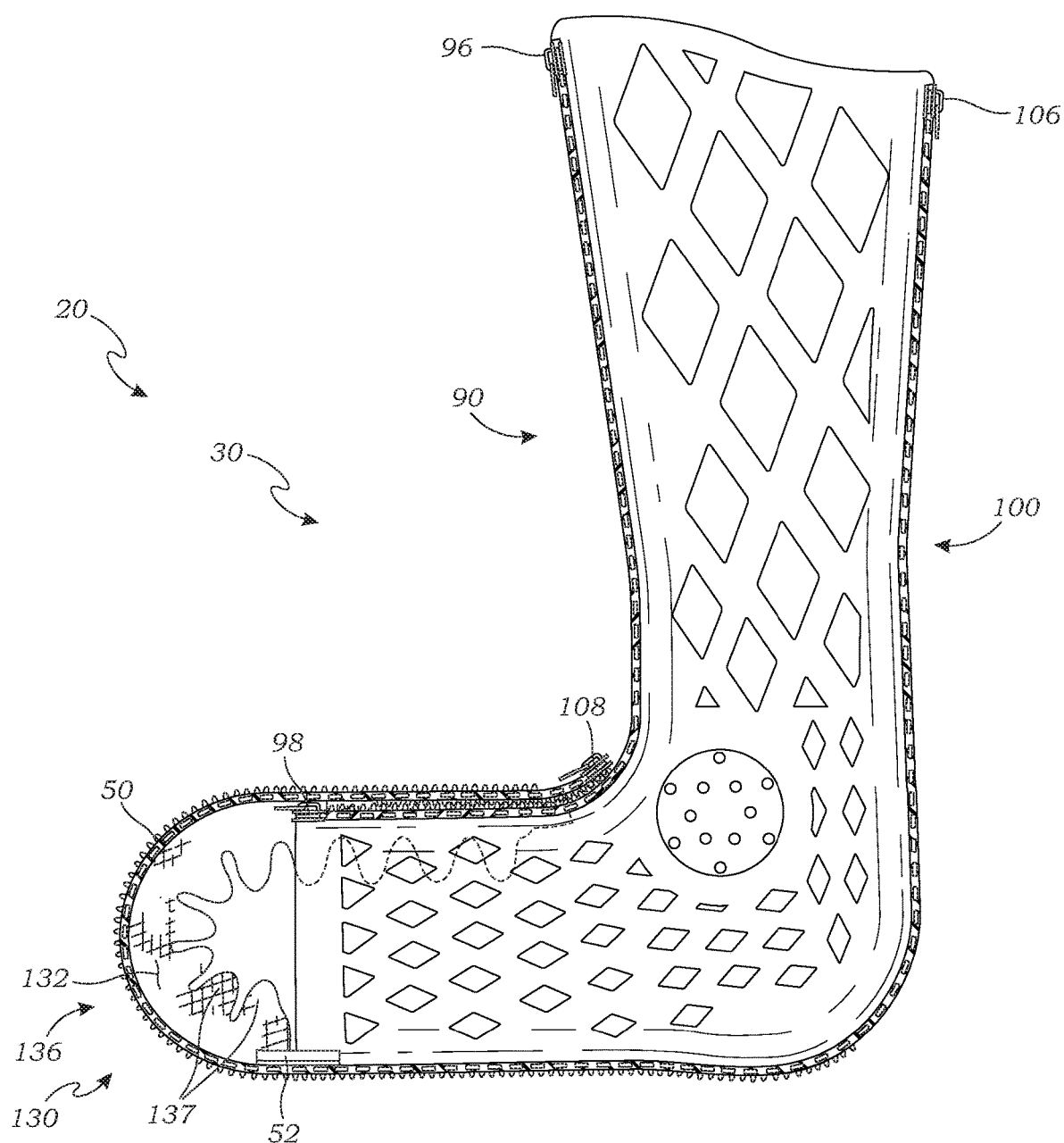
FIG. 18A is a side elevation view thereof in a first exemplary hardened third operational mode, in accordance with at least one embodiment.
Figure 18B:
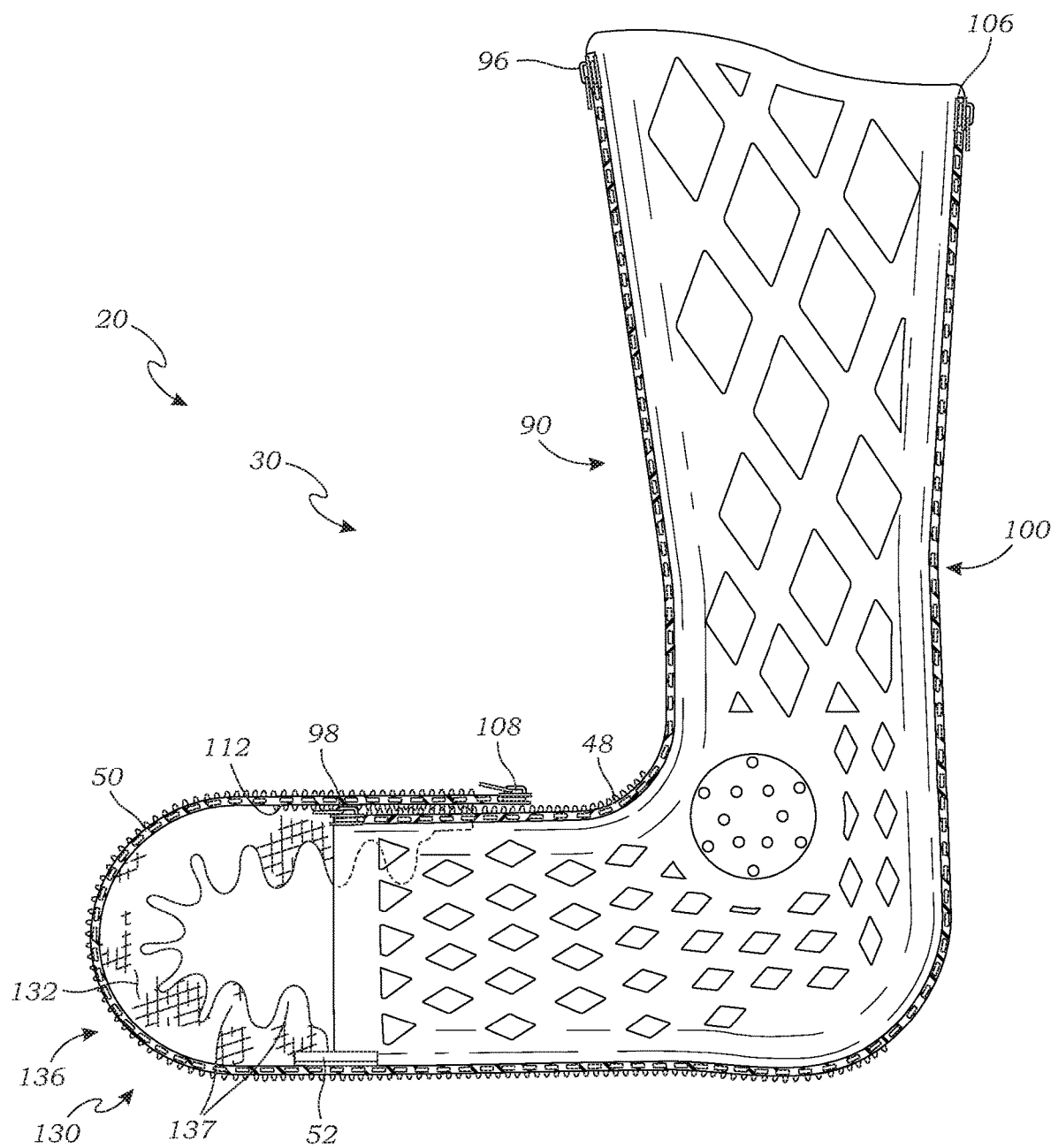
FIG. 18B is a side elevation view thereof in a second exemplary hardened third operational mode, in accordance with at least one embodiment.

Referring next to FIGS. 18A and 18B, there are shown side elevation schematic views of the alternative exemplary orthosis apparatus 20 according to aspects of the present invention in two illustrated operational modes, or essentially two different size configurations of the otherwise same orthosis 20. In both, the view is taken across the vertical mid-plane of the device at the front and back zipper assemblies 90, 100, with the second shell member 60 removed or cut away for ease of viewing into effectively the cross-section of the first shell member 30. As such, it will be appreciated that in each view there is shown the orthosis first shell member 30 with its front and back zipper assemblies 90, 100, the back zipper assembly 100 again terminating distally in the now-formed integral toe box 130, here there being seen the first toe box member 136 as herein described. The optional first attachment material 50 is also shown in these views as installed along the back zipper assembly 100 from its distal end at least roughly to the heel region of the apparatus 20, more about which is said below in connection with FIG. 19. As also shown again here in FIGS. 18A and 18B, a first reinforcing material 52 may be applied across the joint between the toe box 130 and the body of the apparatus 20, or here between the first toe box member 136 and the first shell member 30, so as to provide integrity and comfort at the transition from the body to the toe box 130, which again is effectively a "living hinge." In this regard, it will again be appreciated that the drawings are schematic in nature and no such components should be taken from the drawings as being dimensionally or proportionately accurate or literally to scale. Indeed, regarding the reinforcing materials 52, 82, such are likely relatively thin and provide a smooth transition across to the toe box 130, it being appreciated by those skilled in the art generally and even with reference to the schematic side views of FIGS. 18A and 18B that the bottom of each shell member 30, 60 is in the exemplary embodiment substantially coplanar with the bottom portion of the toe box members 136, 138 for a relatively continuous and somewhat flat bottom of the orthotic 20 from heel to toe, with no noticeable or significant steps or changes in elevation, particularly again at the transition to the toe box 130, it being further appreciated that any variations may also be accounted for through an employed insole 140 (FIGS. 16 and 17), or in some cases a bottom rocker feature 26 (FIG. 23) may be formed in the orthosis 20 via a corresponding rocker member 154 of an alternative insole 140 (FIGS. 23-25), more about which is said below. In regards to sizing, once more, it is expected that generally three nominal sizes—"small," "medium," and "large"—would be provided to cover a substantial portion of the target (e.g., adult) population (e.g., 95% conformity). Again, here, for purposes of illustration, the apparatus 20 shown and described is in connection with such a "medium" sized AFO. Taking typical U.S. foot or shoe sizes, such a "medium" orthosis 20 may accommodate the range of size 7 to size 10, as compared to a "small" covering sizes 3 to 6 or a "large" covering sizes 11 to 13, for example—again, all such sizing being illustrative and non-limiting. Continuing with the "medium" sized AFO example, and with reference to FIG. 14 as well and the related discussion above, the foot portions or first and second lower aperture regions 44, 74 of the apparatus 20 may roughly set a "heel to toe" length on the small end of the range, in this example a shoe size 7, further accounting for a bit of the toes T and any insole 140 (FIGS. 16 and 17) to be positioned just beyond the lower end 24 of the apparatus 20 and thus within the toe box 130. As such, with reference first to FIG. 18A, it will be appreciated that to adjust or customize the exemplary medium-sized AFO apparatus 20 to the small end of its range, during the formation and fitment process explained above, the clinician would fold or bend the then-malleable toe box 130 relatively tightly to the lower end 24 of the apparatus 20 and affix the free end of the toe box 130 and back zipper assembly 100 relatively higher up the forefoot area of the apparatus 20, here specifically as shown in connection with the first shell member 30 as by removably engaging the back first zipper strip fastener member 112 (FIG. 18B) formed on the inside surface 132 of the first toe box member 136 and/or on the back first zipper strip 102 (FIG. 16) of the back zipper assembly 100 with the first shell fastener member 48 (FIG. 18B) formed along the front first zipper strip 92 (FIG. 17) of the front zipper assembly 90 at the forefoot region of the first shell member 30. Those skilled in the art will appreciate that by forming a tighter curve in the toe box 130 during fitment and so attaching the toe box higher up the AFO body, the overall "heel-to-toe" length of the AFO apparatus 20 is thus rendered relatively smaller, again, something on the order of an adult size 7 in the "medium" sized AFO example. By comparison, with reference now to FIG. 18B, the exemplary medium-sized AFO apparatus 20 is here fitted to the large end of its range, wherein once again during the formation and fitment process explained above, the clinician would fold or bend the then-malleable toe box 130 relatively loosely beyond the lower end 24 of the apparatus 20 and affix the free end of the toe box 130 and back zipper assembly 100 relatively lower down the forefoot area of the apparatus 20, again here in connection with the first shell member 30 as by removably engaging the back first zipper strip fastener member 112 formed on the inside surface 132 of the first toe box member 136 and/or on the back first zipper strip 102 (FIG. 16) of the back zipper assembly 100 with the first shell fastener member 48 formed along the front first zipper strip 92 (FIG. 17) of the front zipper assembly 90 at the forefoot region of the first shell member 30. Here, it will be appreciated that by forming a looser or more distal curve in the toe box 130 during fitment and so attaching the toe box lower on the AFO body, the overall "heel-to-toe" length of the AFO apparatus 20 is thus rendered relatively larger, here something on the order of an adult size 10 in the "medium" sized AFO example. It will be appreciated by those skilled in the art that an AFO apparatus 20 according to aspects of the present invention is thus capable in only a few manufactured sizes or configurations of covering a large percentage of the target population, considering that the apparatus 20 is ambidextrous or works for right or left applications, as also may be true for the insole, with particular reference to FIG. 26 and the related discussion below, and that the custom formable hinged toe box 130 can be fitted as desired to cover a range of sizes or foot lengths, not to mention again the custom forming of the overall orthosis 20 as described herein to account for other anatomical variance across the population. As such, there is provided according to aspects of the present invention a highly adaptable and universal orthotic apparatus 20, which may be varied in configuration and sized or scaled up or down to accommodate a wide array of applications beyond the exemplary human lower leg context.

Figure 19:
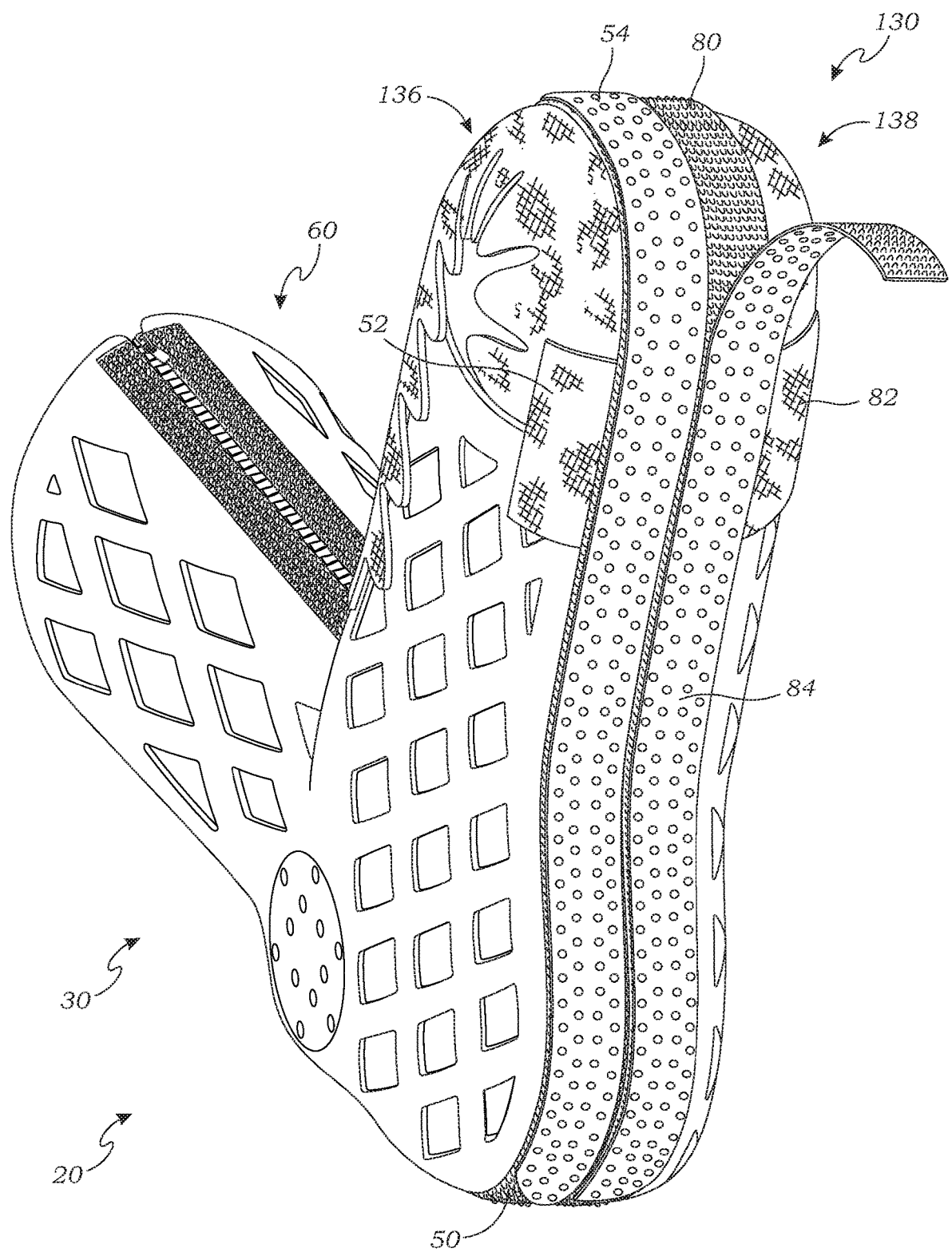
FIG. 19 is a bottom perspective view thereof, in accordance with at least one embodiment.
Figure 20A:
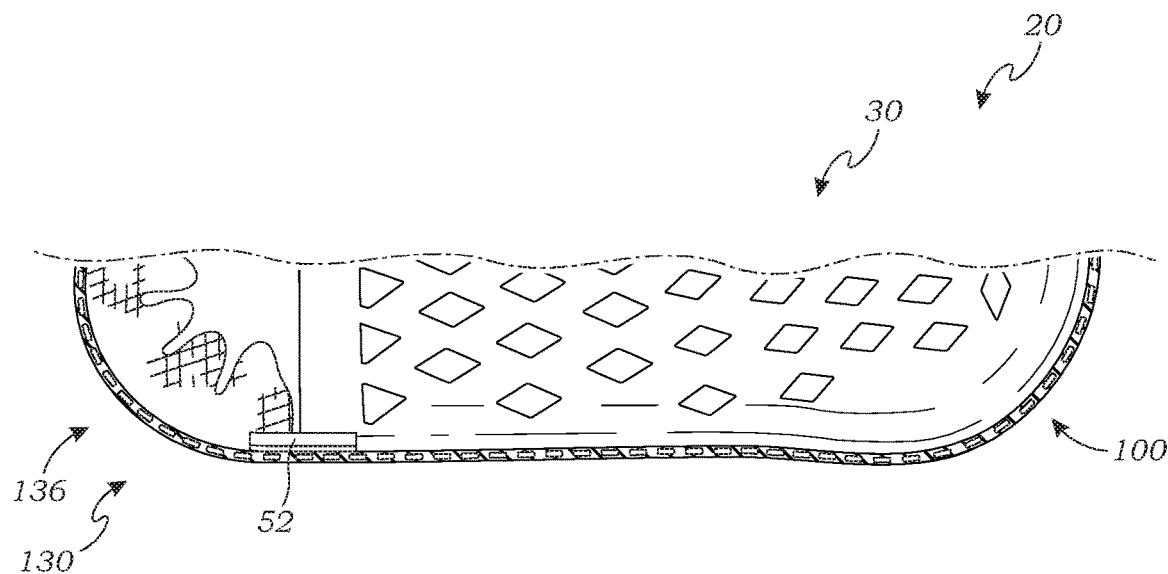
FIG. 20A is an enlarged, partial side elevation view thereof in the third operational mode, in accordance with at least one embodiment.
Figure 20B:
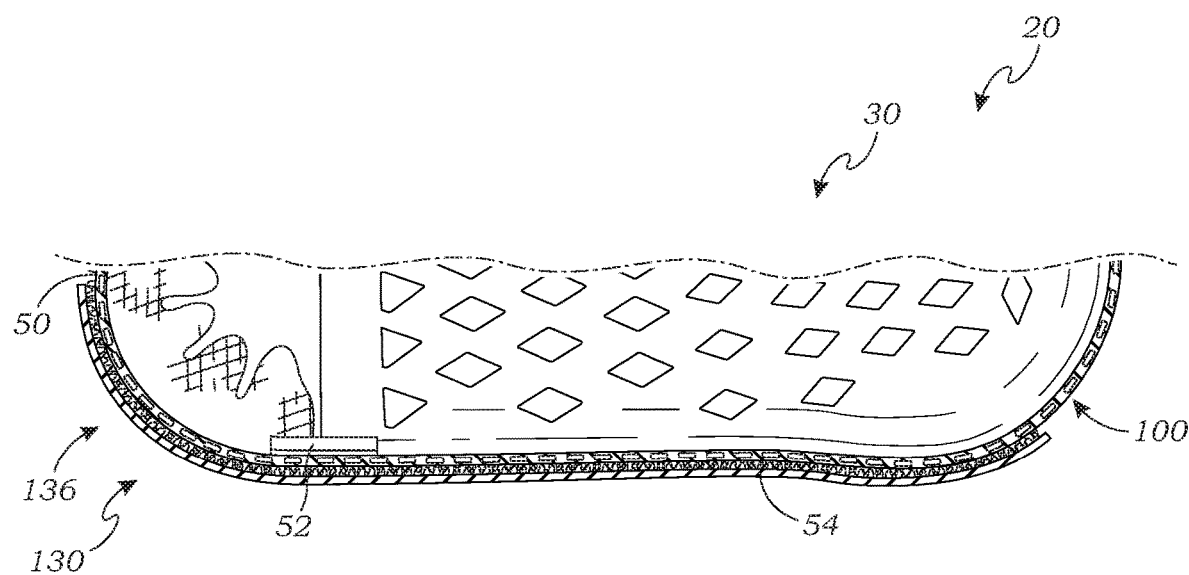
FIG. 20B is an enlarged, partial side elevation view thereof in a fourth operational mode, in accordance with at least one embodiment.

Briefly, turning to FIG. 19 there is shown a bottom perspective view of the alternative exemplary orthosis apparatus 20 according to aspects of the present invention here showing first and second strips of non-slip material 54, 84 selectively applied along the bottom of the orthosis 20 as by being removably engaged with the respective first and second strips of attachment material 50, 80 applied along the length of the back zipper assembly 100 (FIGS. 17 and 18) at least from its distal end associated with the toe box 130 and along the entire underside of the apparatus shell members 30, 60 to and around the heel region. Such non-slip materials 54, 84 may take a variety of types and forms, such that the parallel, lengthwise strips are to be understood as merely illustrative and non-limiting. By way of further illustration and not limitation, rather than two separate, spaced-apart strips 54, 84, a single wider strip spanning both shells 30, 60 and thereby covering the back zipper assembly 100 completely in the region beneath such non-slip material is also possible. And while any such non-slip materials 54, 84 are shown as themselves being formed on their opposite sides with Velcro® hook-and-loop material so as to removably engage the respective strips of attachment material 50, 80, other means of engagement of such non-slip material with the orthosis 20, whether temporary or permanent and whether now known or later developed, may be employed according to aspects of the present invention without departing from its spirit and scope. One exemplary material that may be employed as such non-slip material(s) 54, 84 is Vibram® manufactured by Vibram S.P.A. in Italy, though again, a wide variety of materials, now known or later developed, may be employed. In the exemplary embodiment, both the non-slip strips 54, 84 and the associated attachment strips 50, 80 are on the order of 80 mm wide, though it will be appreciated that such is merely illustrative and non-limiting. As also seen in FIG. 19, optionally, first and second reinforcing materials 52, 82 may be applied at the joint or hinge connection between the body of the AFO apparatus 20 and the toe box 130 on the outside of the shells 30, 60 and respective toe box members 136, 138 instead of or in addition to at the joint on the inside of the apparatus 20 as shown in FIG. 16. Relatedly, in the partial side schematic views of FIGS. 20A and 20B, somewhat analogous to that of FIG. 18A, there are shown an exemplary such orthosis apparatus 20 with either no separate non-slip material, instead the material of the shell 30 or any coating thereon supplying such properties as in FIG. 20A, or having a non-slip material 54 applied as by Velcro® to an underlying attachment material 50 as in FIG. 20B, there the non-slip material 54 going from heel to toe of the orthosis 20 as in FIG. 19.

Turning next to FIGS. 21A-21C, there are shown various enlarged cross-sectional views taken from the associated section lines in FIG. 10 demonstrating exemplary construction and layering of the orthosis 20, generally and in the region of any fastening or closure means such as a zipper. As a threshold matter, it is noted that the sections happen to have been taken substantially at the upper end 62 of the second shell member 60, it being appreciated that the shells 30, 60 again being symmetrical such that such structure is representative of the first shell member 30 as well, and of the various alternative embodiments of the AFO apparatus 20, though not necessarily so. First, in FIG. 21A, there is shown a partial end cross-sectional view illustrating a portion of the thermoformable substrate 66 having applied on its inner and outer surfaces a coating 86. As with the other figures, it is again noted that such are schematic in nature and not to be taken literally or to scale in terms of material configurations, sizes, thicknesses, and other attributes. By way of illustration and not limitation, the nominal substrate thickness may be in the range of 2 to 8 mm generally, or nominally 5 mm, versus closer to 2 mm such as at the indented malleoli rings, while the coating thickness may be in the range of 40 to 200 µm, or nominally or in some cases preferably 80 µm. As such, those skilled in the art will appreciate that the coating 86 is generally on the order of one hundred to one thousand times thinner than, or dimensionally is an order of magnitude of one hundred to one thousand different from, the substrate 66. As seen in FIGS. 21B and 21C, sectional views taken along an edge of the shell, here the second back edge 70 of the second shell 60, though again the shells 30, 60 being symmetrical such that similar sections would be formed in the other three shell edges 38, 40, 68, the edge region 70 may be thicker to increase stiffness or structural integrity or rigidity in that region, at least relative to the main body of the shell 60, so as to maintain the lengthwise edges of the shell 60 or render them substantially non-stretching so as to prevent detachment of the zipper assembly 100, or the back second zipper strip 104 in the exemplary sectional view, from the shell 60. Such exemplary reinforced (thicker) lengthwise edges 38, 40, 68, 70 of the two halves 30, 60 where the zipper assemblies 90, 100 are attached thus yield reduced stretch and increased stiffness and zipper retention—the device engineered to not stretch appreciably in those lengthwise regions even when heated. Alternatively, in a further exemplary embodiment, not shown, the edge regions taper down from the nominal 5 mm substrate thickness, such as to 3 mm, which thinner edge region may assist in zipper attachment and retention. As such, it will be appreciated that according to aspects of the present invention the rounded edge region may be thicker or thinner and/or wider or narrower as needed. As explained elsewhere herein, attaching the zipper assemblies 90, 100 to the shells 30, 60 or substrates 36, 66 may be achieved in a number of ways now known or later developed, including but not limited to a pressure sensitive adhesive ("PSA") 120 as shown in FIG. 21C, which may be single width strips on each side of the substrate 66 or, as shown, a double-wide strip that wraps the edge so as to simultaneously be applied to both the inner and outer surfaces of the substrate edge, as particularly advantageous where the zipper assembly 100 is attached on both the inner and outer surfaces as by positioning inner and outer zipper strips 104 therealong. The width of the cloth material or zipper strips 92, 94, 102, 104 is substantially non-stretchable in the exemplary embodiment, which alone or in conjunction with the edges 38, 40, 68, 70 again effectively creates a non-stretch area laterally on the edges of the shells 30, 60. By engineering the width of this area there is created a "non-stretch" area of the shells 30, 60 in the exemplary embodiment that provides a minimum strength and rigidity of the device 20 after molding on a patient. Once more, any other suitable or relatively non-stretch closure means now known or later developed may be employed in selectively joining the opposed edges 38, 40, 68, 70 of the respective first and second shell members 30, 60, such that the zippers 90, 100 are to be understood as illustrative and non-limiting. Furthermore, in alternative embodiments both the closure means and the lateral shell edges may also be stretchable when the shells are activated or heated for forming just as across the bodies of the shells, with such lateral areas still stiffening once the shells harden and set.

Figure 22:
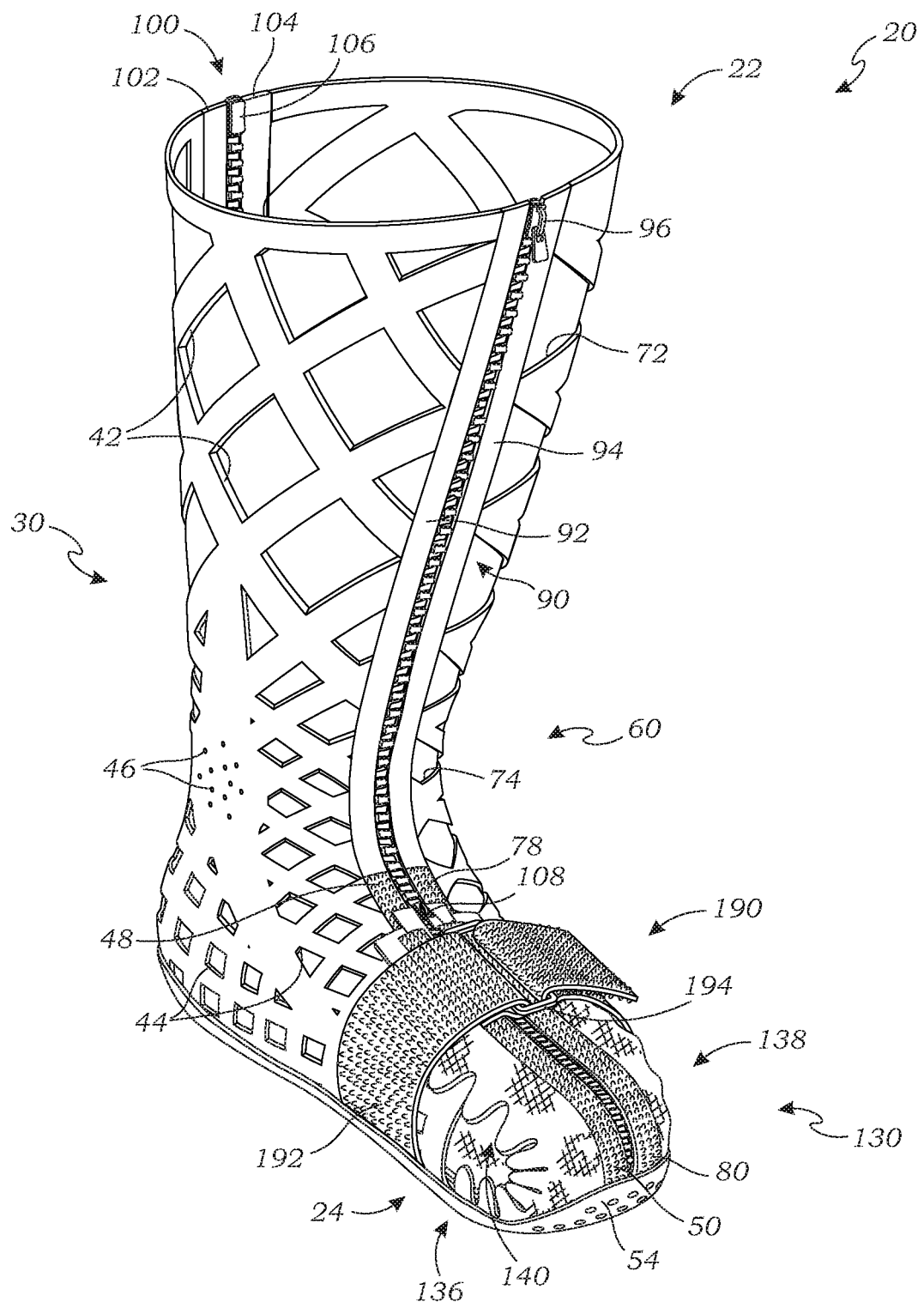
FIG. 22 is a perspective view of a further alternative exemplary orthosis apparatus, in accordance with at least one embodiment.

Referring briefly to FIG. 22, there is shown a perspective view of a still further alternative exemplary orthosis apparatus 20 according to aspects of the present invention, analogous to that of FIG. 13 with a few notable differences. First, it is simply observed that an insole 140 is shown as positioned within the apparatus 20 as is visible through openings in the closed toe box 130. Second, a single strip of non-slip material 54 is applied to the bottom of the apparatus 20 substantially from "heel-to-toe" and from "side-to-side," which material 54 may again be affixed as by Velcro® employing the first and second attachment materials 50, 80 incorporated into the apparatus 20 as herein described, and any other such attachment material portions (not shown), as appropriate, or by any other temporary or permanent means now known or later developed, including directly incorporating such material 54 into the shells 30, 60 themselves during production. And third and somewhat relatedly, an optional strap 190 is shown as being applied about the forefoot or over the top of the closed toe box 130 for additional strength and integrity. Such strap 190 may be integrally formed with the apparatus 20, or the respective shells 30, 60 thereof, regardless may be positioned above or below any non-slip material 54 applied to the bottom of the apparatus 20, or may simply be applied about the apparatus 20 in a secondary step but otherwise not directly affixed to the apparatus 20. In the exemplary embodiment, such strap 190 is shown as being above the non-slip material 54, or positioned between the non-slip material 54 and the bottoms of the opposite shells 30, 60, for further securement of the strap 190, though again such is not required. Such strap 190 may generally comprise a strap body 192 and a D-loop bracket 194 about which the strap body 192 is slidably engaged for tightening down and securing the strap 190 in a manner generally known, as may entail a textile and Velcro® based strap or any other suitable materials now known or later developed. In a particular exemplary embodiment, such strap 190 may be configured as a so-called "compliance strap" such as disclosed in applicant's U.S. Pat. No. 8,821,423, incorporated herein by reference, whereby the security strap 190 may be wrapped and secured about the orthosis 20 as shown to prevent tampering with or unauthorized removal of the orthosis 20, in which case such strap 190 may be secured to the orthosis 20 directly or may be retained on the orthosis 190 as by the optional non-slip material 54. Or, a separate compliance strap (not shown) as per the '423 patent may be employed in the ankle or smallest circumference region of the orthosis 20 above the ankle so as to further insure that the compliance strap cannot be removed without being destroyed, thereby again preventing tampering with or unauthorized removal of the orthosis 20. While the strap 190 may be configured in a variety of ways and sizes in terms of length and width, in an exemplary, non-limiting embodiment the strap body 192 is approximately 40 mm wide, which it will be appreciated would substantially cover the free end of the toe box 130, or the end folded over the forefoot of the body of orthosis apparatus 20, to render the overall apparatus 20 relatively rigid and sturdy.

Figure 23:
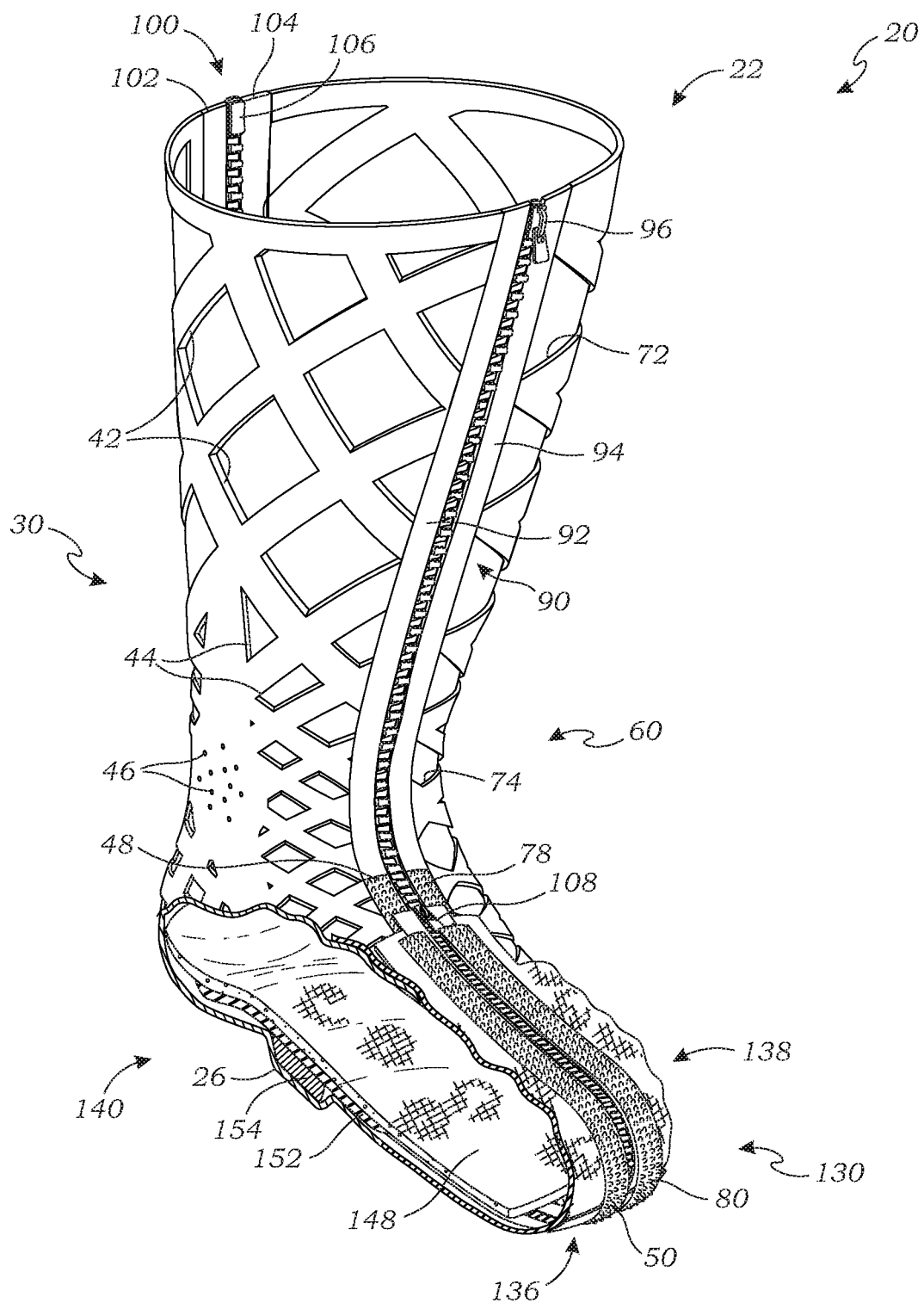
FIG. 23 is a perspective, partially cut-away view of a still further alternative exemplary orthosis apparatus, in accordance with at least one embodiment.
Figure 24:
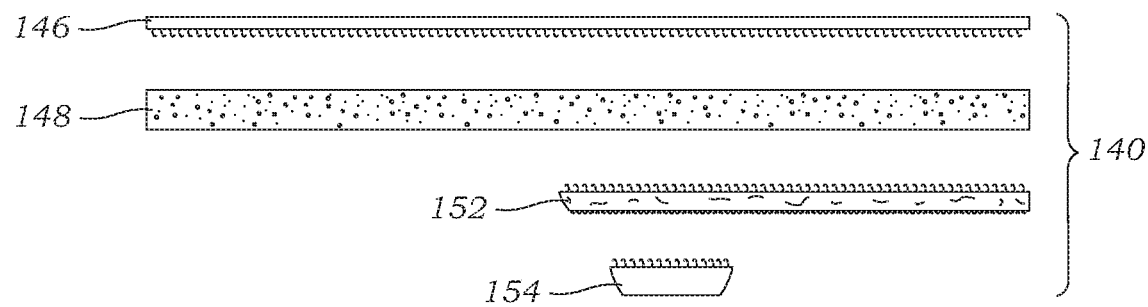
FIG. 24 is an exploded side elevation view of an alternative exemplary insole thereof in a pre-formed, unassembled state, in accordance with at least one embodiment.
Figure 25A:
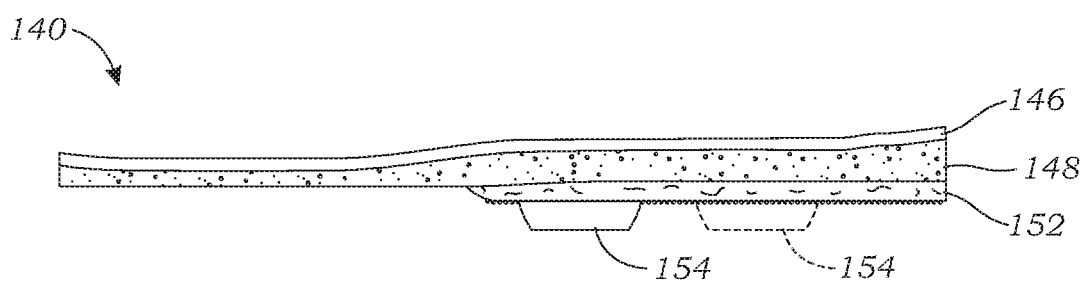
FIG. 25A is a side elevation view thereof in a formed, assembled state, in accordance with at least one embodiment.
Figure 25B:
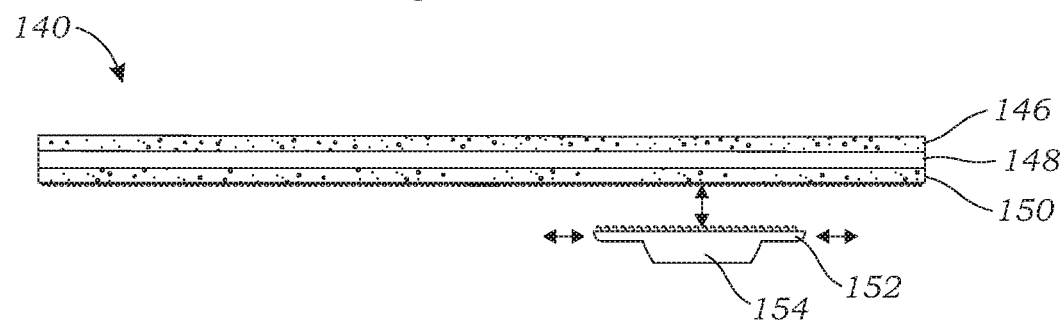
FIG. 25B is a side elevation view a further alternative exemplary insole thereof in a formed, assembled state, in accordance with at least one embodiment.

Turning next to FIG. 23, there is shown a partially cut-away perspective view of yet another alternative exemplary orthosis apparatus 20 according to aspects of the present invention, again generally analogous to that of FIG. 13, here with an alternative insole 140 configured to form a somewhat downwardly protruding bottom rocker feature 26 in the bottom of the apparatus 20, which it will be appreciated can serve to further offload a particular area of the apparatus 20 and thus the foot F therein as deemed appropriate by the clinician. For simplicity here in FIG. 23, the insole 140 is shown as comprising a single layer 148 of a compressible and/or moldable material that runs the "heel-to-toe" length of the orthosis 20 and has affixed or attached to its bottom surface, temporarily or permanently, a somewhat rigid rocker member 154 and associated rocker base 152. Those skilled in the art will appreciate that by placing such a rigid rocker member 154 beneath the insole 140, during forming of the orthosis 20 as above described, such rocker member 154 will thus form or cause to be formed, in cooperation with the clinician's manipulation and fitment of the orthosis 20 on the leg L of the patient, a similar protrusion or rocker feature 26 at the bottom of the orthosis 20, which once fully hardened and in use results in selective offloading of an affected area of the foot F. As such, the bottom rocker feature 26 is effectively formed in the orthosis 20 from the inside thereof, or interiorly, as again by the incorporation of the rocker member 154 within the insole 140, which has a number of advantages in practice. In a bit more detail, and now with reference to the exploded side elevation view of an alternative exemplary insole 140 in a pre-formed, unassembled state, the insole 140 comprises an upper layer 146 and an intermediate layer 148 that together form the full-length insole 140 and may be permanently integrated as by bonding, lamination, or the like, or may be removably engaged as by hook-and-loop fasteners, pressure-sensitive adhesives, or the like, as well as the rocker member 154 here again either permanently or removably engageable with a rigid rocker base 152. In the illustrated embodiment, the base 152 may be removably engageable or selectively positionable relative to the intermediate layer 148 and the rocker member 154 may be removably engageable or selectively positionable relative to the rocker base 152, in all such cases employing any appropriate engagement means now known or later developed. Those skilled in the art will thus appreciate that such an arrangement related to the positioning of the rocker member 154 relative to the overall insole 140 provides tremendous versatility to the clinician in placing the rocker member 154 and thus forming the bottom rocker feature 26 in the orthosis 20 in the desired anatomical location. As an aside, where such an AFO apparatus 20 formed with a bottom rocker feature 26 is to be worn inside a walker boot or cast shoe or the like (not shown), it will be appreciated that the insole of such boot or cast shoe may be modified with adjacent, spaced-apart pads configured to straddle the rocker feature 26 and thereby allow for proper and comfortable seating of the orthosis 20 within the walker boot or cast shoe. In the exemplary embodiment, each of the four layers or components comprising the insole 140 of FIG. 24 are temporarily joined to the adjacent layer or component employing Velcro® hook-and-loop fasteners and/or related velour swatches, though again such is merely illustrative and non-limiting. Continuing with the exemplary embodiment of FIG. 24, the intermediate layer 148 may be a custom moldable thermoplastic foam or the like, with the upper layer 146 formed of a closed cell foam such as Plastazote®. Accordingly, and with brief reference now to FIG. 25A showing the alternative exemplary insole 140 of FIG. 24 in its assembled and formed state, it will be appreciated that prior to formation of the insole 140 and thus of the overall orthosis 20, the rocker member 154 is again selectively positionable along the rocker base 152 as illustrated, which rigid region of the insole 140 would be less susceptible to deformation or to being trimmed to length as may be done at the free or opposite end of the insole 140, more about which is said below in connection with FIG. 26. By way of further illustration and not limitation, and with continued reference to FIGS. 24 and 25A, the main or intermediate layer 148 of the insole 140 may be on the order of 12 mm thick in its initial, unformed state, with the Plastazote® or other such upper layer 146 maybe being on the order of 4 mm thick. Similarly, the rigid rocker base 152 may be approximately 4 mm thick compared to a rocker member 154 thickness or stand-off height of roughly 15 mm, with the width and length of the rocker member 154 being approximately 50 mm, again, just for illustration. Such rocker base 152 and rocker member 154 may again be separate components as in FIGS. 24 and 25A or integral as shown in the alternative embodiment of FIG. 25B, with any such rocker arrangements being interchangeable or "mixed and matched" with any such insole assemblies as involving upper, intermediate, or lower layers 146, 148, 150, as appropriate. Of course, a variety of other arrangements and numbers and configurations of such layers and components in forming the finished insole 140 are possible according to aspects of the present invention without departing from its spirit and scope. By way of further illustration and not limitation, in forming the rocker member 154 and any related base 152 or other such feature, it will be appreciated that any appropriate materials and methods of construction now known or later developed may be employed, including but not limited to metals such as steel, aluminum, alloys, and the like and a variety of plastics such as polypropylene, polystyrene, polyvinyl chloride ("PVC"), acrylonitrile butadiene styrene ("ABS"), polyethylenes such as high density polyethylene ("HDPE") and low density polyethylene ("LDPE"), polycarbonate, polyurethane, and other such plastics, thermoplastics, thermosetting polymers, and the like, and even wood, any such components being fabricated or formed as through injection molding, casting, extrusion, machining, stamping, routing, forming, or any other such technique now known or later developed. Relatedly, such components may again be formed integrally or may be formed separately and then assembled in any appropriate secondary operation employing any assembly technique now known or later developed, including but not limited to fastening, bonding, welding, over-molding or coining, press-fitting, snapping, or any other such technique now known or later developed, or of course may be formed separately and then configured for being removably rather than permanently engaged as set forth herein. Similarly, while a particular first exemplary embodiment in FIGS. 24 and 25A is shown and described, it will again be appreciated that an insole 140 according to aspects of the present invention may be formed of a variety of layers in terms of the materials, order in which the materials are layered, and the means of engaging the layers of material. Generally, materials such as polypropylene, Korex® or other brand closed cell vinyl foam, and ethylene vinyl acetate ("EVA") may be employed in such insoles 140, any of which potentially coated with or having a top layer or cover of Plastazote® or other brand closed cell cross-linked polyethylene foam, Procell® or other brand open cell polyurethane foam, or Poron® or other brand microcellular polyurethane foam. Indeed, with reference now to the further alternative exemplary embodiment of FIG. 25B, the main portion of the insole 140 may instead be a three-layer construction, here comprising an upper layer 146 again of Plastazote® or other brand closed cell cross-linked polyethylene foam, an intermediate layer 148 of Poron® or other such microcellular polyurethane foam, and a lower layer 150 of ethylene vinyl acetate ("EVA"). Removably and repositionably affixed to the bottom surface of the lower layer 150 is an integral rocker base 152 and member 154 as indicated by the arrows in FIG. 25B. Once more, such removable engagement between such rocker assembly 152, 154 and the one or more layers 146, 148, 150 together defining the insole 140 may be via any appropriate means now known or later developed, including but not limited to double-sided tape and Velcro® hook-and-loop fasteners. By way of further illustration and not limitation, a two-sided tape (not shown) may be pre-installed, as during manufacturing, to the upwardly-facing surface of the rigid rocker base 152, with its backing paper (not shown) peeled off to effectively activate the two-sided tape and allow the rocker base 152 and integral rocker member 154 to then be located as desired on the bottom of the insole 140's lower layer 150 in this example. In the exemplary embodiment, such rocker base 152 extends approximately 25 mm on either side of the rocker member 154. Once again, those skilled in the art will appreciate that a variety of other configurations of an insole 140 and related components according to aspects of the present invention are possible, such that those shown and described herein are to be understood as merely illustrative and non-limiting. Back to the "offloading" characteristic of such insoles 140, with or without the rocker member 154, as employed within an orthosis 20 according to aspects of the present invention as compared to the offloading performance of regular walking shoes or to prior art total contact casts according to published data, the results of initial testing are quite compelling as to the advantages of features and aspects of the present invention. By way of background, testing was performed using a third-party Pedar™ Pressure Mapping System to capture peak plantar pressures at the forefoot, midfoot, and heel of an eighty-five kilogram (85 kg) subject wearing each orthotic in question, measured over at least thirty (30) steps. As a point of reference, when the subject wore a regular walking shoe, peak pressure measured at the forefoot was on the order of 310 to 360 kPa/cm$^2$, at the midfoot was on the order of 110 to 160 kPa/cm$^2$, and at the heel was on the order of 245 to 295 kPa/cm$^2$. Analogous published data for a typical "total contact cast" ("TCC") indicates peak pressure measured at the forefoot of approximately 175 kPa/cm$^2$, at the midfoot of approximately 85 kPa/cm$^2$, and at the heel of approximately 145 kPa/cm$^2$ (see, Polio, F. E., et al., "Plantar Pressures in Fiberglass Total Contact Casts vs. a New Diabetic Walking Boot," *Foot & Ankle International*, vol. 24, no. 1, 1 Jan. 2003, pp. 45-49; see also, Armstrong, David G., and Shea, Susan S., "Total Contact Casts and Removable Cast Walkers. Mitigation of Plantar Heel Pressure," *American Podiatric Medical Association*, vol. 89, no. 1, January 1999, indicating a TCC plantar heel pressure of approximately 180 kPa/cm$^2$). While the prior art "total contact cast" ("TCC") would certainly seem by all accounts to be an improvement over more typical footwear when it comes to pressure offloading, which is so important for patients suffering from diabetic foot ulcers (DFU's) and other such conditions of the plantar area of the foot, there is still room for much improvement, which need is met by an orthosis 20 according to aspects of the present invention. Indeed, by comparison, an AFO orthosis 20 such as shown in FIG. 13 having an insole 140 as in FIG. 25B was tested, with much improved plantar pressure offloading results—first, without the optional rocker member 154, peak pressure measured at the forefoot was on the order of 125 to 175 kPa/cm$^2$, at the midfoot was on the order of 70 to 120 kPa/cm$^2$, and at the heel was on the order of 160 to 210 kPa/cm$^2$, and then with the optional rocker member 154, peak pressure measured at the forefoot was on the order of 80 to 130 kPa/cm$^2$, at the midfoot was again on the order of 70 to 120 kPa/cm$^2$, and at the heel was on the order of 125 to 175 kPa/cm$^2$. While these are relatively small sample sizes and the test data performed with the Pedar™ Pressure Mapping System isn't necessarily the same in experimental design to that of the TCC studies carried out and reported by Polio and Armstrong, there is initial good evidence that features of an orthosis 20 according to aspects of the present invention can indeed reduce, even significantly, peak plantar pressures, providing clinical benefits in use, particularly when the optional rocker member 154 is employed, which it will be appreciated uniformly engages the midfoot of a patient, thereby transferring forefoot and heel pressures to the midfoot, on which basis the forefoot and hell regions are offloaded. Once more, those skilled in the art will appreciate that a variety of other configurations and combinations of an AFO orthosis 20 and any insole 140 and rocker member 154 are possible according to aspects of the present invention without departing from the spirit and scope of the invention, through which still further offloading and other advantages may be realized. By way of further illustration and not limitation, those skilled in the art will appreciate that in particular contexts the combination of an AFO orthosis 20 and an insole 140 with a rocker member 154 may reduce any height difference between the affected foot with the orthosis 20 and the unaffected foot with conventional footwear, which it will be appreciated even if small or subtle could make a noticeable difference over time in terms of mitigating against other complications including spine, back, and hip pains, etc. in patients wearing casts and walkers with relatively large height differences from one foot or leg to the other.

Figure 26:
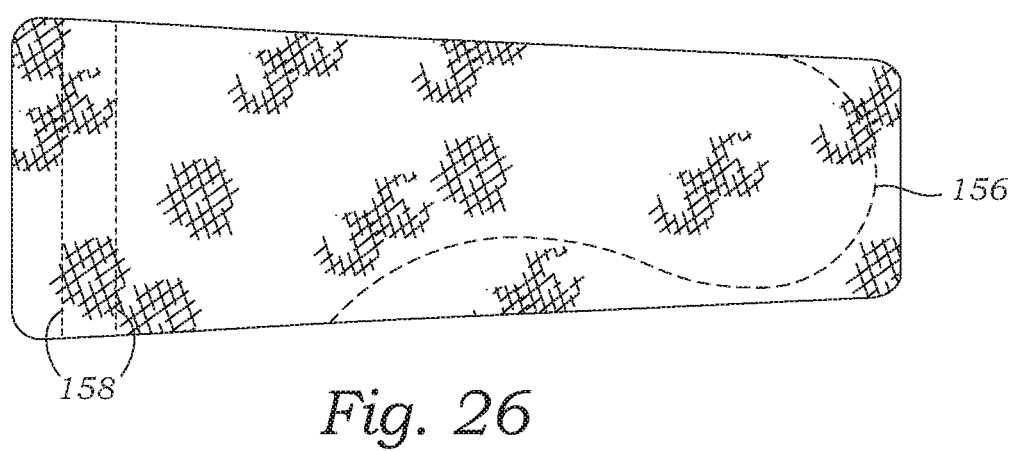
FIG. 26 is a top elevation view a still further alternative exemplary insole thereof, in accordance with at least one embodiment.

Briefly and finally, referring to FIG. 26, there is shown a top elevation view of a still further exemplary insole 140 according to aspects of the present invention for use in an orthosis apparatus 20 as herein disclosed or otherwise, such insole 140 "blank" is substantially universal in that by flipping it one way or another horizontally or about its lengthwise axis it can serve as or be used in both right foot and left foot applications. Particularly, as shown, the insole 140, of whatever material(s) and construction, may be formed having a contour area 156 such as having raised or pre-formed areas at the arch and/or heel cup. Also, such universal insole 140 may be further customizable as being trimmable to length and shape at its distal end, as indicated by and even having provided thereon one or more transverse trim lines 158 to aid in such fitment by the clinician prior to placement of any such insole 140 within the orthosis apparatus 20 (e.g., FIGS. 1 and 13).

It can be appreciated from the foregoing that an insole 140 according to aspects of the present invention in any of the material and layer configurations described herein or otherwise, and with or without the optional attachable rocker 154, could also be fitted inside a plaster or fiberglass cast (not shown) during forming to impart and achieve at least some of the same beneficial offloading and pressure distribution effects as achieved by the custom moldable AFO orthosis 20 described herein. More generally, those skilled in the art will again appreciate that various combinations of features of one or more components of an apparatus 20 according to aspects of the present invention may be combined in a number of other ways beyond those shown and described without departing from the spirit and scope of the invention.

Aspects of the present specification may also be described as follows:

1. An orthosis apparatus comprising: a first shell member and an opposed second shell member, the first shell member having a first front edge and an opposite first back edge, and the second shell member having a second front edge and an opposite second back edge; a front zipper assembly joined to and selectively closing the respective first and second front edges as by a front first zipper strip affixed at the first front edge and a front second zipper strip affixed at the second front edge; and a back zipper assembly joined to and selectively closing the respective first and second back edges as by a back first zipper strip affixed at the first back edge and a back second zipper strip affixed at the second back edge; whereby heat activation of the apparatus allows for conformable placement of the first and second shell members about a body part of a patient that is to be immobilized; whereby selective closure of the front and back zipper assemblies joins the first and second shell members along the respective first and second front and back edges to install the apparatus about the body part of the patient; whereby cooling of the apparatus causes the first and second shell members to take a set conforming to the body part of the patient; and whereby selective opening of one or both of the front and back zipper assemblies separates the first and second shell members along one or both of the respective first and second front and back edges to uninstall and allow removal of the apparatus from the body part of the patient, at least a portion of one of the front and back zipper assemblies allowing for selective hinging of the set first and second shell members for ease of removal and replacement of the apparatus in use.

2. The apparatus of embodiment 1 having an upper end and an opposite lower end and wherein at least one of the front and back zipper assemblies extends distally beyond the first and second shell members at the lower end of the apparatus.

3. The apparatus of embodiment 1 or embodiment 2 wherein a distal end of the back zipper assembly extends distally beyond the first and second shell members at the lower end of the apparatus.

4. The apparatus of embodiment 3 wherein the back zipper assembly comprises at least one zipper strip fastener member on an inner surface thereof for selective engagement with a corresponding at least one shell fastener member.

5. The apparatus of embodiment 4 wherein a first shell fastener member is formed on the front first zipper strip adjacent the first lower end of the first shell member and a second shell fastener member is formed on the front second zipper strip toward the second lower end of the second shell member, and wherein a back first zipper strip fastener member is formed on the back first zipper strip distal of a first lower end of the first shell member for selective engagement with the first shell fastener member and a back second zipper strip fastener member is formed on the back second zipper strip distal of a second lower end of the second shell member for selective engagement with the second shell fastener member.

6. The apparatus of embodiment 4 or embodiment 5 wherein a toe box is incorporated into the distal end of the back zipper assembly, the selective engagement of the at least one zipper strip fastener member with the corresponding at least one shell fastener member serving to selectively secure the toe box in a curved and closed position over the lower end of the apparatus, and the selective disengagement of the at least one zipper strip fastener member from the corresponding at least one shell fastener member serving to selectively shift the toe box to an open position pivoted away from the lower end of the apparatus, whereby during heat activation and forming the adjustability of the toe box enables a single apparatus to accommodate a range of foot sizes.

7. The apparatus of embodiment 6 wherein the toe box is removably engaged with the back zipper assembly.

8. The apparatus of embodiment 7 wherein an inner surface of the toe box selectively engages the at least one zipper strip fastener member.

9. The apparatus of embodiment 8 wherein the toe box is formed having an outer surface configured to removably engage the back first and second zipper strip fastener members to selectively secure the toe box on the distal end of the back zipper assembly.

10. The apparatus of embodiment 6 wherein the toe box is integral with the back zipper assembly.

11. The apparatus of embodiment 10 wherein the toe box comprises opposed first and second toe box members affixed to and extending laterally from the respective back first and second zipper strips.

12. The apparatus of embodiment 11 wherein a first reinforcing material spanning from the first shell member to the first toe box member and a second reinforcing material spanning from the second shell member to the second toe box member cooperate with the back zipper assembly to stabilize the toe box and enable the toe box to selectively pivot relative to the lower end of the apparatus.

13. The apparatus of embodiment 11 or embodiment 12 wherein the back zipper assembly comprises at least one attachment material on an outer surface thereof for selective engagement with a non-slip material.

14. The apparatus of any of embodiments 11-13 wherein a first attachment material is applied along the back first zipper strip spanning the first toe box member and a first bottom portion of the first shell member and a second attachment material is applied along the back second zipper strip spanning the second toe box member and a second bottom portion of the second shell member, and whereby the non-slip material is removably engaged to both the first and second attachment materials so as to cover at least part of the back zipper assembly at the first and second bottom portions of the respective first and second shell members.

15. The apparatus of embodiment 14 wherein a first non-slip material is removably engaged with the first attachment material and a second non-slip material is removably engaged with the second attachment material.

16. The apparatus of any of embodiments 6-15 wherein the toe box is formed with lateral protrusions to facilitate selective bending of the toe box without bunching.

17. The apparatus of embodiment 16 wherein first protrusions extend from the first toe box member laterally away from the back first zipper strip and second protrusions extend from the second toe box member laterally away from the back second zipper strip.

18. The apparatus of any of embodiments 6-17 wherein the toe box is a thermoformable material.

19. The apparatus of any of embodiments 1-18 further comprising aperture regions configured for providing increased stretchability during heat activation and forming of the apparatus and increased breathability during setting and use of the apparatus.

20. The apparatus of embodiment 19 further comprising a first lower aperture region and a second lower aperture region formed in the respective first and second shell members adjacent to the respective first and second lower ends.

21. The apparatus of embodiment 20 further comprising a first upper aperture region and a second upper aperture region formed in the respective first and second shell members adjacent to respective first and second upper ends opposite the first and second lower ends, apertures of the first and second upper aperture regions being relatively larger than apertures of the first and second lower aperture regions to accommodate larger size variation in forming the upper end of the apparatus.

22. The apparatus of embodiment 21 wherein the apertures of the first and second upper aperture regions are diamond-shaped.

23. The apparatus of any of embodiments 19-22 further comprising a first intermediate aperture region and a second intermediate aperture region formed in the respective first and second shell members between the upper end and the lower end of the apparatus.

24. The apparatus of embodiment 23 wherein apertures of the first and second intermediate aperture regions are relatively smaller than apertures of both the first and second upper aperture regions and the first and second lower aperture regions.

25. The apparatus of any of embodiments 1-24 wherein the front and back zipper assemblies contribute to lengthwise non-stretch zones in the apparatus even when heat activated and formable.

26. The apparatus of any of embodiments 1-25 wherein the first shell member comprises a first substrate having a first coating and the second shell member comprises a second substrate having a second coating.

27. The apparatus of embodiment 26 wherein the first and second substrates are a thermoformable material.

28. The apparatus of embodiment 26 or embodiment 27 wherein the first and second coatings are selected from the group consisting of silicone and polyurethane.

29. The apparatus of any of embodiments 1-28 wherein the front zipper assembly comprises front top and bottom zipper pulls and the back zipper assembly comprises back top and bottom zipper pulls.

30. The apparatus of any of embodiments 1-29 wherein the back zipper assembly is approximately 20% longer than the first and second back edges.

31. The apparatus of embodiment 30 wherein the back zipper assembly is in the range of 15% to 25% longer than the first and second back edges.

32. The apparatus of any of embodiments 1-31 wherein the first and second shell members are symmetrical.

33. The apparatus of any of embodiments 1-32 further comprising an insole having an upper surface and an opposite lower surface and selectively positionable within the apparatus between the first and second shell members such that the upper surface is facing toward the upper end of the apparatus.

34. The apparatus of embodiment 33 wherein the insole comprises multiple layers.

35. The apparatus of embodiment 34 wherein at least one layer is a thermoformable material.

36. The apparatus of embodiment 34 or embodiment 35 wherein at least one layer is a closed cell foam.

37. The apparatus of embodiment 36 wherein the closed cell foam is at the upper surface.

38. The apparatus of any of embodiments 34-37 comprising at least an upper layer, an intermediate layer adjacent to the upper layer, and a lower layer adjacent to the intermediate layer.

39. The apparatus of embodiment 38 wherein the upper layer is a closed cell cross-linked polyethylene foam, the intermediate layer is a microcellular polyurethane foam, and the lower layer is an ethylene vinyl acetate.

40. The apparatus of any of embodiments 33-39 wherein the insole is compressible.

41. The apparatus of any of embodiments 33-40 wherein the insole further comprises a rocker extending away from the lower surface.

42. The apparatus of embodiment 41 wherein the rocker is integral with the insole.

43. The apparatus of embodiment 41 wherein the rocker is removably engageable with the insole.

44. The apparatus of any of embodiments 41-43 wherein the rocker comprises a rocker base and a rocker member.

45. The apparatus of embodiment 44 wherein the rocker base and the rocker member are integral.

46. The apparatus of embodiment 44 or embodiment 45 wherein the rocker base is removably engageable with the lower surface of the insole such that the rocker base is selectively repositionable relative to the lower surface of the insole.

47. The apparatus of any of embodiments 44-46 wherein the rocker base and the rocker member are removably engageable such that the rocker member is selectively repositionable relative to the rocker base.

48. The apparatus of any of embodiments 41-47 wherein the rocker forms a corresponding bottom rocker feature in the first and second shell members of the apparatus when heat activated and formed with the insole and rocker therein.

49. The apparatus of any of embodiments 33-48 wherein the insole is trimmable.

50. The apparatus of embodiment 49 wherein trim lines are provided on at least one of the upper and lower surfaces of the insole.

51. The apparatus of any of embodiments 1-50 further comprising at least one of an inflation bladder and a cold therapy pad selectively positioned between the first and second shell members.

52. The apparatus of embodiment 51 wherein the inflation bladder comprises an inflation bladder body and an inflation line in fluid communication with the inflation bladder body, the inflation line passing through an aperture formed in the first or second shell members.

53. The apparatus of embodiment 51 wherein the cold therapy pad comprises a cold therapy pad body and an inlet line and an outlet line both in fluid communication with the cold therapy pad body, the inlet and outlet lines passing through one or more apertures formed in the first or second shell members.

54. The apparatus of any of embodiments 1-53 further comprising at least one strap about the first and second shell members to assist in securement and fitment of the apparatus.

55. The apparatus of embodiment 54 wherein the at least one strap comprises a compliance strap that must be destroyed to be removed.

56. A method of employing an orthosis apparatus as defined in any one of embodiments 1-55, the method comprising the steps of: heating the apparatus to activate the thermoformable first and second shell members; applying the activated apparatus to a body part of a patient to be immobilized as by positioning the malleable first and second shell members thereabout; closing the front and back zipper assemblies to secure the apparatus on the body part of the patient; and forming the first and second shell members about the body part as the apparatus cools to set.

57. The method of embodiment 56 wherein the body part includes a foot and the step of applying the activated apparatus further comprises positioning an insole between the foot and the first and second shell members.

58. The method of embodiment 57 comprising the further step of having the back zipper assembly zipped at least from the distal end to the heel of the foot to facilitate placement of the insole.

59. The method of embodiment 57 or embodiment 58 comprising the further step of selectively positioning a rocker on the lower surface of the insole so as to form a corresponding bottom rocker feature in the first and second shell members during the step of forming the first and second shell members, the bottom rocker feature providing plantar pressure offloading during use of the apparatus.

60. The method of any of embodiments 57-59 comprising the further step of trimming the insole to an appropriate length based on the foot of the patient.

61. The method of any of embodiments 57-60 comprising the further step of forming a thermoformable toe box installed on the distal free end of the back zipper assembly of the apparatus as by bending and curving the toe box comfortably about the toes of the foot of the patient.

62. The method of embodiment 61 comprising the further step of affixing a back zipper strip fastener member to a shell fastener member to removably secure the toe box in the desired position.

63. The method of embodiment 61 or embodiment 62, further comprising the step of hinging open the toe box to inspect the toes of the patient without removing the apparatus.

64. The method of any of embodiments 56-63, further comprising the step of applying one or more retention or compliance straps about the first and second shell members.

65. The method of any of embodiments 56-64, further comprising the step of applying a non-slip material on the sole of the apparatus.

66. The method of embodiment 65 wherein the step of applying a non-slip material comprises removably attaching the non-slip material to attachment material formed along at least a portion of the back zipper assembly.

67. The method of any of embodiments 56-66, further comprising the step of unzipping at least one of the front and back zipper assemblies in whole or in part to allow hinged movement between the first and second shell members and selective removal and replacement of the apparatus.

68. A kit comprising an orthosis apparatus as defined in any one of embodiments 1-55.

69. The kit of embodiment 68 comprising a first shell member, a second shell member, and a toe box.

70. The kit of embodiment 68 or embodiment 69, further comprising an insole.

71. The kit of embodiment 70 comprising a plurality of rockers.

72. The kit of any of embodiments 68-71, further comprising one or more of a stockinette and a liner.

73. The kit of any of embodiments 68-72, further comprising one or more non-slip strips.

74. The kit of any of embodiments 68-73, further comprising a plurality of straps.

75. The kit of any of embodiments 68-74, further comprising one or more of an inflation bladder and a cold therapy pad.

76. The kit of any of embodiments 68-75, further comprising instructional material.

77. The kit of embodiment 76, wherein the instructional material provides instructions on how to perform the method as defined in any one of embodiments 56-67.

78. Use of an orthosis apparatus as defined in any one of embodiments 1-55 to selectively immobilize a body part of a patient.

79. The use of embodiment 78, wherein the use comprises a method as defined in any one of embodiments 56-67.

In closing, regarding the exemplary embodiments of the present invention as shown and described herein, it will be appreciated that an improved orthosis apparatus is disclosed and configured for being selectively formed and applied and removed. Because the principles of the invention may be practiced in a number of configurations beyond those shown and described, it is to be understood that the invention is not in any way limited by the exemplary embodiments, but is generally able to take numerous forms without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

In some embodiments, the numbers expressing quantities of ingredients, properties such as concentration, reaction conditions, and so forth, used to describe and claim certain embodiments of the inventive subject matter are to be understood as being modified in some instances by the terms "about" or "approximately." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. The recitation of numerical ranges of values herein is merely intended to serve as a shorthand method of referring individually to each separate value falling within the range. Unless otherwise indicated herein, each individual value of a numerical range is incorporated into the specification as if it were individually recited herein. Similarly, all lists of values should be considered as inclusive of intermediate values unless the context indicates the contrary.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the application should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C and N, the text should be interpreted as requiring only one element from the group, not A plus N, or B plus N, etc.

While aspects of the invention have been described with reference to at least one exemplary embodiment, it is to be clearly understood by those skilled in the art that the invention is not limited thereto. Rather, the scope of the invention is to be interpreted only in conjunction with any appended claims here or in any patent application claiming the benefit hereof, and it is made clear that the inventor(s) believe that the claimed subject matter is the invention.

What is claimed is:

1. A thermoformable orthosis apparatus comprising:
a thermoformable first shell member and an opposed thermoformable second shell member, the first shell member having a first front edge and an opposite first back edge, and the second shell member having a second front edge and an opposite second back edge;

a front zipper assembly joined to and selectively closing the respective first and second front edges as by a front first zipper strip affixed at the first front edge and a front second zipper strip affixed at the second front edge; and a back zipper assembly joined to and selectively closing the respective first and second back edges as by a back first zipper strip affixed at the first back edge and a back second zipper strip affixed at the second back edge;

whereby heat activation of the apparatus allows for conformable placement of the first and second shell members about a body part of a patient that is to be immobilized;

whereby selective closure of the front and back zipper assemblies joins the first and second shell members along the respective first and second front and back edges to install the apparatus about the body part of the patient;

whereby cooling of the apparatus causes the first and second shell members to set conforming to the body part of the patient; and whereby selective opening of one or both of the front and back zipper assemblies separates the first and second shell members along one or both of the respective first and second front and back edges to uninstall and allow removal of the apparatus from the body part of the patient, at least a portion of one of the front and back zipper assemblies allowing for selective hinging of the set first and second shell members for ease of removal and replacement of the apparatus in use; and further wherein:

the back first and second zipper strips at a distal end of the back zipper assembly extend distally beyond the respective first and second shell members at a lower end of the apparatus;

the back zipper assembly comprises at least one zipper strip fastener member on an inner surface thereof for selective engagement with a corresponding at least one shell fastener member; and a toe box is incorporated into the distal end of the back zipper assembly, the selective engagement of the at least one zipper strip fastener member with the corresponding at least one shell fastener member serving to selectively secure the toe box in a curved and closed position over the lower end of the apparatus, and the selective disengagement of the at least one zipper strip fastener member from the corresponding at least one shell fastener member serving to selectively shift the toe box to an open position pivoted away from the lower end of the apparatus, whereby during heat activation and forming the adjustability of the toe box enables a single apparatus to accommodate a range of foot sizes.

2. The apparatus of claim 1 wherein the toe box is removably engaged with the back zipper assembly.

3. The apparatus of claim 1 wherein the toe box is integral with the back zipper assembly.

4. The apparatus of claim 3 wherein the toe box comprises opposed first and second toe box members affixed to and extending laterally from the respective back first and second zipper strips of the back zipper assembly.

5. The apparatus of claim 4 wherein a first reinforcing material spanning from the first shell member to the first toe box member and a second reinforcing material spanning from the second shell member to the second toe box member cooperate with the back zipper assembly to stabilize the toe box and enable the toe box to selectively pivot relative to the lower end of the apparatus.

6. The apparatus of claim 1 wherein the toe box is formed with lateral protrusions to facilitate selective bending of the toe box without bunching.

7. The apparatus of claim 1 wherein the toe box is a thermoformable material.

8. The apparatus of claim 1 wherein the front first and second zipper strips and the back first and second zipper strips are formed of a non-elastic material, whereby the respective first and second front edges and first and second back edges of the first and second shell members are reinforced and rendered non-elastic so as to form lengthwise non-stretch zones in the apparatus.

9. The apparatus of claim 1 wherein the back zipper assembly comprises at least one attachment material on an outer surface thereof for selective engagement with a non-slip material.

10. The apparatus of claim 1 further comprising aperture regions configured for providing increased stretchability during heat activation and forming of the apparatus and increased breathability during setting and use of the apparatus, wherein the front and back zipper assemblies contribute to lengthwise non-stretch zones in the apparatus even when heat activated and formable to maintain the overall integrity of the apparatus.

11. The apparatus of claim 10 further comprising a first upper aperture region and a second upper aperture region formed in the respective first and second shell members adjacent to respective first and second upper ends opposite respective first and second lower ends of the respective first and second shell members, apertures of the first and second upper aperture regions being relatively larger than apertures of the first and second lower aperture regions formed in the respective first and second shell members adjacent to the respective first and second lower ends to accommodate larger size variation in forming the first and second upper ends of the respective first and second shell members of the apparatus.

12. The apparatus of claim 1 further comprising an insole having an upper surface and an opposite lower surface and being selectively positionable within the apparatus between the first and second shell members such that the upper surface is facing toward an upper end of the apparatus, the insole comprising multiple layers.

13. The apparatus of claim 12 wherein at least one layer of the insole is a thermoformable material.

14. The apparatus of claim 12 wherein the insole comprises at least an upper layer, an intermediate layer adjacent to the upper layer, and a lower layer adjacent to the intermediate layer, wherein the upper layer is a closed cell cross-linked polyethylene foam, the intermediate layer is a microcellular polyurethane foam, and the lower layer is ethylene vinyl acetate.

15. The apparatus of claim 12 wherein the insole further comprises a selectively repositionable rocker extending away from the lower surface, the rocker configured to form a corresponding bottom rocker feature in the first and second shells of the apparatus when heat activated and formable.

16. A thermoformable orthosis apparatus comprising:
a thermoformable first shell member and an opposed thermoformable second shell member, the first shell member having a first front edge and an opposite first back edge, and the second shell member having a second front edge and an opposite second back edge;

a front zipper assembly joined to and selectively closing the respective first and second front edges as by a front first zipper strip affixed at the first front edge and a front second zipper strip affixed at the second front edge;

a back zipper assembly joined to and selectively closing the respective first and second back edges as by a back first zipper strip affixed at the first back edge and a back second zipper strip affixed at the second back edge, a distal end of the back zipper assembly extending distally beyond the first and second shell members at a lower end of the apparatus; and a thermoformable toe box formed integrally with the distal end of the back zipper assembly, the toe box comprising opposed first and second toe box members affixed to and extending laterally from the respective back first and second zipper strips of the back zipper assembly and terminating laterally in spaced-apart protrusions;

whereby heat activation of the apparatus allows for conformable placement of the first and second shell members and the toe box about a body part of a patient that is to be immobilized;

whereby selective closure of the front and back zipper assemblies joins the first and second shell members along the respective first and second front and back edges to install the apparatus about the body part of the patient and selective pivoting of the toe box about the lower end of the apparatus positions the toe box in a curved configuration over the lower end, during heat activation and forming the adjustability of the toe box enabling a single apparatus to accommodate a range of foot sizes;

whereby cooling of the apparatus causes the first and second shell members and the toe box to set conforming to the body part of the patient;

whereby selective pivoting of the toe box opens the lower end of the apparatus; and whereby selective opening of one or both of the front and back zipper assemblies separates the first and second shell members along one or both of the respective first and second front and back edges to uninstall and allow removal of the apparatus from the body part of the patient, at least a portion of one of the front and back zipper assemblies allowing for selective hinging of the set first and second shell members for ease of removal and replacement of the apparatus in use.

* * * * *